US005770544A

United States Patent [19]
Yokota et al.

[11] Patent Number: 5,770,544
[45] Date of Patent: Jun. 23, 1998

[54] CONDENSED HETEROCYCLIC DERIVATIVES AND HERBICIDES

[75] Inventors: Sumio Yokota; Masafumi Matsuzawa; Nobuyuki Ohba; Toshihiro Nagata; Shigehiko Tachikawa; Takeshige Miyazawa; Katsutada Yanagisawa, all of Shizuoka, Japan

[73] Assignees: Kumiai Chemical Industry Co., Ltd.; Ihara Chemical Industry Co., Ltd., both of Tokyo, Japan

[21] Appl. No.: 728,531

[22] Filed: Oct. 9, 1996

Related U.S. Application Data

[62] Division of Ser. No. 204,199, filed as PCT/JP93/00909, Jul. 2, 1993, Pat. No. 5,616,537.

[30] Foreign Application Priority Data

| | | | |
|---|---|---|---|
| Jul. 3, 1992 | [JP] | Japan | 4-199054 |
| May 14, 1993 | [JP] | Japan | 5-136808 |

[51] Int. Cl.[6] .................. C07D 403/10; C07D 405/10; C07D 409/10; A01N 43/66

[52] U.S. Cl. .................. 504/230; 544/198; 544/207; 544/212; 544/209; 544/219; 544/180; 544/217; 544/218; 544/216

[58] Field of Search .................. 544/198, 207, 544/212, 209, 219, 180, 217, 218, 216; 504/230

[56] References Cited

U.S. PATENT DOCUMENTS 5,616,537 4/1997 Pokota et al. .................. 544/320

*Primary Examiner*—John M. Ford
*Attorney, Agent, or Firm*—Oblon, Spivak, McClelland, Maier & Neustadt, P.C.

[57] ABSTRACT

A condensed heterocyclic derivative of the formula (I):

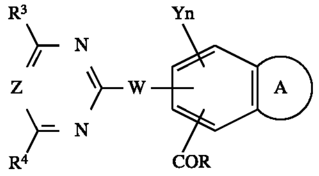

(wherein R is a hydroxyl group, $R^3$ or $R^4$is an alkoxy group, W is an oxygen atom, Yn is a hydrogen atom, Z is a methine group, and A is a 5- or 6-membered heterocyclic ring which may be substituted, and a herbicide, are presented. When used for paddy field treatment, upland soil treatment and foliage treatment, the condensed heterocyclic derivative of the present invention exhibits excellent herbicidal activities against gramineous and non-gramineous weeds without adversely affecting crop plants.

6 Claims, No Drawings

CONDENSED HETEROCYCLIC DERIVATIVES AND HERBICIDES

This is a Division of application Ser. No. 08/204,199 filed on Mar. 1, 1994, now U.S. Pat. No. 5,616,537, which was filed as International Application PCT/JP93/00909 on Jul. 2, 1993.

TECHNICAL FIELD

The present invention relates to condensed heterocyclic derivatives and their salts as well as herbicides containing them as active ingredients, which can be applied to paddy fields, upland fields and non-agricultural fields.

BACKGROUND ART

The present inventors found that quinoline and naphthalene derivatives have herbicidal activities and disclosed specific examples in Japanese Unexamined Patent Publication No. 56469/1990. Further, Japanese Unexamined Patent Publication No. 121973/1990 discloses that aromatic carboxylic acid derivatives containing quinoline, naphthalene, benzofuran, thiophene or pyridine ring have herbicidal activities.

However, the above-mentioned publications disclose nothing about specific compounds relating to the condensed heterocyclic derivatives of the present invention. Further, these compounds are not necessarily satisfactory from the viewpoint of the herbicidal effects. A number of other herbicides have been developed and contributed to the saving of energy for agricultural operations and to the improvement of the productivity. However, in their practical use, such herbicides also have various problems with respect to the herbicidal effects and the safety to crop plants.

The present inventors have conducted an extensive research on condensed heterocyclic derivatives with an object to develop a compound which is excellent in the herbicidal activities without bringing about phytotoxicity to crop plants. As a result, it has been found that the compounds of the present invention which are pyrimidine or triazine derivatives bonded to a condensed heterocyclic ring exhibit excellent herbicidal activities against not only annual weeds but also perennial gramineous weeds, cyperaceous weeds and broad leaf weeds in the paddy field treatment, upland soil treatment and foliage treatment, and they are highly safe to crop plants. The present invention has been accomplished on the basis of this discovery.

DISCLOSURE OF THE INVENTION

Namely, the present invention relates to a condensed heterocyclic derivative of the formula (I):

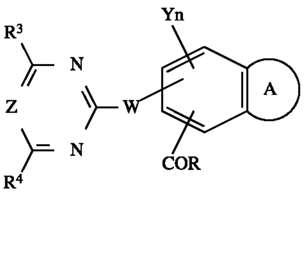

{wherein A is a heterocyclic ring of the formula

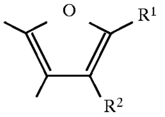

(A-1)

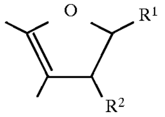

(A-2)

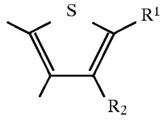

(A-3)

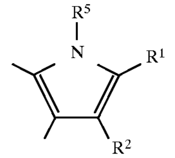

(A-4)

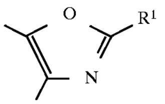

(A-5)

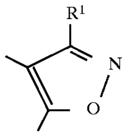

(A-6)

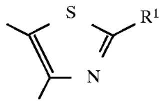

(A-7)

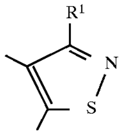

(A-8)

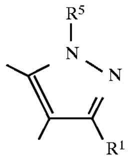

(A-9)

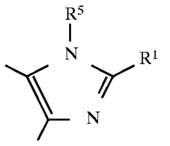

(A-10)

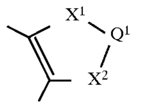

(A-11)

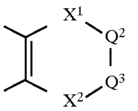

(A-12)

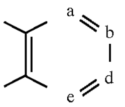

(A-13)

R is a hydrogen atom, a hydroxyl group, an alkoxy group which may be substituted, a benzyloxy group which may be substituted, an aryloxy group which may be substituted, an alkylthio group which may be substituted, a benzylthio group which may be substituted, an arylthio group which may be substituted, an alkenyloxy group which may be substituted, an alkynyloxy group which may be substituted, an alkenylthio group which may be substituted, an alkynylthio group which may be substituted, an alkylideneaminoxy group, or a group of the formula —$NR^6R^7$ (wherein each of $R^6$ and $R^7$ which may be the same or different, is a hydrogen atom, an alkyl group, an alkoxy group, a benzyl group, an aryl group which may be substituted, an alkylsulfonyl group, or an arylsulfonyl group which may be substituted, or $R^6$ and $R^7$ may, together with the nitrogen atom, form a ring which may contain a hetero atom), each of $R^1$ and $R^2$ which may be the same or different, is a hydrogen atom, a formyl group, an alkylcarbonyl group which may be substituted, a cycloalkylcarbonyl group, an arylcarbonyl group which may be substituted, a pyridylcarbonyl group which may be substituted, a carboxyl group, a group of the formula —$CONR^6R^7$ (wherein $R^6$ and $R^7$ are as defined above), an alkylthiocarbonyl group which may be substituted, a cycloalkylthiocarbonyl group, an aryloxycarbonyl group which may be substituted, an alkoxycarbonyl group which may be substituted, a cycloalkyl group, an alkyl group which may be substituted, an alkenyl group which may be substituted, an alkynyl group which may be substituted, an alkoxy group which may be substituted, an aryl group which may be substituted, a halogen atom, a benzyloxycarbonyl group which may be substituted, a benzylthiocarbonyl group which may be substituted, a cycloalkoxycarbonyl group, an arylthiocarbonyl group which may be substituted, an alkenyloxycarbonyl group which may be substituted, an alkynyloxycarbonyl group which may be substituted, an alkenylthiocarbonyl group which may be substituted, an alkynylthiocarbonyl group which may be substituted, an isopropylideneaminoxycarbonyl group, a nitro group, a cyano group, a halogenated carbonyl group, a group of the formula $CR^8{=}N{-}R^9$ (wherein $R^8$ is a hydrogen atom, an aryl group, or an alkyl group, and $R^9$ is a hydroxyl group, an alkyl group, an aryl group which may be substituted, a benzyl group which may be substituted, a benzyloxy group which may be substituted, an alkoxy group, an alkenyloxy group, an alkynyloxy group, a phenoxy group which may be substituted, an alkylamino group, a dialkylamino group, an arylamino group which may be substituted, or an arylsulfonylamino group which may be substituted), a group of the formula $NR^{10}R^{11}$ (wherein each of $R^{10}$ and $R^{11}$ which may be the same or different, is a hydrogen atom, an alkyl group, an aryl group which may be substituted, a benzyl group which may be substituted, a formyl group, an alkylcarbonyl group which may be substituted, a cycloalkylcarbonyl group, an arylcarbonyl group which may be substituted, a pyridylcarbonyl group which may be substituted, an alkoxycarbonyl group, an alkylsulfonyl group, an arylsulfonyl group which may be substituted, a carbamoyl group, an alkylthiocarbonyl group or an arylthiocarbonyl group which may be substituted, or $R^{10}$ and $R^{11}$ may, together with the nitrogen atom, form a ring which may contain a hetero atom), a group of the formula $N{=}CR^{12}R^{13}$ (wherein each of $R^{12}$ and $R^{13}$ which may be the same or different, is a hydrogen atom, an alkyl group, or an aryl group which may be substituted, or $R^{12}$ and $R^{13}$ may form a ring which may contain a hetero atom), each of $R^3$ and $R^4$ which may be the same or different, is a hydrogen atom, an alkoxy group which may be substituted, a halogen atom, an alkylamino group, a dialkylamino group, or an alkyl group which may be substituted, $R^5$ is a hydrogen atom, an alkyl group which may be substituted, a formyl group, an alkylcarbonyl group which may be substituted, a cycloalkylcarbonyl group, an arylcarbonyl group which may be substituted, a pyridylcarbonyl group which may be substituted, a carbamoyl group, an alkoxycarbonyl group, an aryloxycarbonyl group, a benzyloxycarbonyl group, an alkylthiocarbonyl group, an arylthiocarbonyl group, an alkylsulfonyl group, an arylsulfonyl group, a trialkylsilyl group, an alkenyl group, an alkynyl group, a 4,6-dimethoxypyridin-2-yl group, or trichloromethylthio group, each of $X^1$ and $X^2$ which may be the same or different, is an oxygen atom, a sulfur atom, a methylene group, a group of the formula $NR^{14}$ (wherein $R^{14}$ is a hydrogen atom or an alkyl group), a carbonyl group, a group of the formula $C{=}NOR^{15}$ (wherein $R^{15}$ is an alkyl group), or a hydroxymethylene group, $Q^1$ is a methylene group, a carbonyl group, or a group of the formula $C{=}C{<}R^{16}R^{17}$ (wherein each of $R^{16}$ and $R^{17}$ which may be the same or different, is a cyano group, a cycloalkylcarbonyl group, a benzoyl group, or an alkoxycarbonyl group), each of $Q^2$ and $Q^3$ which may be the same or different is a group of the formula $C{<}R^{18}R^{19}$ [wherein each of $R^{18}$ and $R^{19}$ which may be the same or different, is a hydrogen atom, an alkyl group, or an alkoxycarbonyl group, or $R^{18}$ and $R^{19}$ together form a carbonyl group or a group of the formula $C{=}CHR^{20}$ (wherein $R^{20}$ is a hydrogen atom or an alkyl group)], and each of a, b, d and e is a nitrogen atom or a methine group, provided that at least one of them is a nitrogen atom (provided that a case where each of a, b and d is a methine group and e is a nitrogen atom, and the formula (I) represents a 8-quinolinecarboxylic acid derivative, is excluded), Y is a halogen atom, an alkyl group which may be substituted, an alkoxy group, a phenyl group which may be substituted, a nitro group, an alkylamino group, or a dialkylamiono group, n is an integer of from 0 to 2, provided that when n is 2, it may represents a combination of different groups, W is an oxygen atom, a sulfur atom, an N-formyl group, a methylene group, a carbonyl group, a cyanomethylene group, and Z is a methine group or a nitrogen atom}, or its salt; and a herbicide containing it as an active ingredient.

As preferred compounds, among them, those of the formula (I) wherein R is a hydrogen atom, a hydroxyl group and a $C_1$–$C_6$ alkoxy group, may, for example, be mentioned. $R^3$ and $R^4$ may, for example, be a halogen atom, which may be a chlorine, bromine, fluorine or iodine atom, a $C_1$–$C_6$ alkyl group or an alkoxy group.

Further, $R^1$ and $R^2$ may, for example, be a $C_1$–$C_8$ alkyl group, a formyl group, a $C_1$–$C_8$ alkylcarbonyl group, a $C_1$–$C_8$ alkoxycarbonyl group, a $C_1$–$C_8$ alkylthiocarbonyl group, a $C_1$–$C_8$ cycloalkoxycarbonyl group, a $C_1$–$C_8$ cycloalkylthiocarbonyl group, a $C_3$–$C_6$ alkenyloxycarbonyl group which may be substituted, a $C_3$–$C_6$ alkenylthiocarbonyl group, a $C_3$–$C_6$ alkynyloxycarbonyl group which may be substituted, or a $C_3$–$C_6$ alkynylthiocarbonyl group, and $R^5$ may, for example, be a hydrogen atom, a formyl group, or a $C_1$–$C_8$ alkylcarbonyl group. Now, specific examples of the compound of the present invention will be shown in Tables 1 to 59. The compound numbers will be referred to in the subsequent description.

TABLE 1

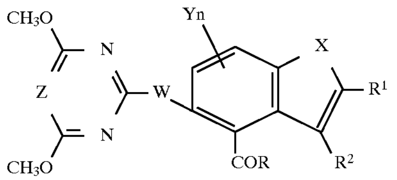

| Compound No. | $R^1$ | $R^2$ | R | W | X | Yn | Z | m.p. (°C.) or ($n_D^{20}$) |
|---|---|---|---|---|---|---|---|---|
| 1 | $CH_3$ | $COOC_2H_5$ | 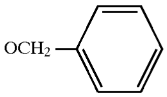 | O | O | H | CH | 127–131 |
| 2 | $CH_3$ | $COOC_2H_5$ | OH | O | O | H | CH | 160–163 |
| 3 | $CH_3$ | $COOC_2H_5$ | $OCH_3$ | O | O | H | CH | 132–133.5 |
| 4 | $CH_3$ | $COOC_2H_5$ | $OCH_2O\underset{\underset{O}{\|}}{C}C_4H_9$-t | O | O | H | CH | 92–93 |
| 5 | $CH_3$ | $COOC_2H_5$ | $NHSO_2CH_3$ | O | O | H | CH | |
| 6 | $CH_3$ | $COOC_2H_5$ | $OCH_2COOC_2H_5$ | O | O | H | CH | 92–94.5 |
| 7 | $CH_3$ | $COOC_2H_5$ | $OC_2H_5$ | O | O | H | CH | 130–131 |
| 8 | $CH_3$ | $COOC_2H_5$ | $OCH_2O\underset{\underset{O}{\|}}{C}C_4H_9$-s | O | O | H | CH | 106.5–109 |
| 9 | $CH_3$ | $COOC_2H_5$ | $O\overset{\overset{CH_3}{\|}}{C}HO\underset{\underset{O}{\|}}{C}C_3H_7$ | O | O | H | CH | 153–157 |
| 10 | $CH_3$ | $COOC_2H_5$ | $O\overset{\overset{CH_3}{\|}}{C}HO\underset{\underset{O}{\|}}{C}C_4H_9$ | O | O | H | CH | 130.5–132 |
| 11 | $CH_3$ | $COOC_2H_5$ | $O\overset{\overset{CH_3}{\|}}{C}HO\underset{\underset{O}{\|}}{C}C_5H_{11}$ | O | O | H | CH | 112.5–114 |
| 12 | $CH_3$ | $COOC_2H_5$ | $OCH_2OC_2H_5$ | O | O | H | CH | 113–116 |
| 13 | $CH_3$ | $COOC_2H_5$ | $OCH_2\underset{\underset{O}{\|}}{C}CH_2COOC_2H_5$ | O | O | H | CH | 1.5429 |
| 14 | $CH_3$ | $COOC_2H_5$ | $OC_3H_7$ | O | O | H | CH | 119–121 |
| 15 | $CH_3$ | $COOC_2H_5$ | $OC_3H_7$-i | O | O | H | CH | 88.5–90 |

TABLE 2

| Compound No. | $R^1$ | $R^2$ | R | W | X | Yn | Z | m.p. (°C.) or ($n_D^{20}$) |
|---|---|---|---|---|---|---|---|---|
| 16 | $CH_3$ | $COOC_2H_5$ | 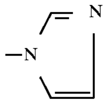 | O | O | H | CH | 146–148 |
| 17 | $CH_3$ | $COOC_2H_5$ | 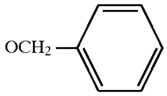 | S | O | H | CH | |
| 18 | $CH_3$ | $COOC_2H_5$ | OH | S | O | H | CH | |

TABLE 2-continued

| Compound No. | $R^1$ | $R^2$ | R | W | X | Yn | Z | m.p. (°C.) or ($n_D^{20}$) |
|---|---|---|---|---|---|---|---|---|
| 19 | $CH_3$ | $COOC_2H_5$ | 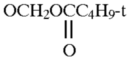 | S | O | H | CH | |
| 20 | $CH_3$ | $COOC_2H_4C_3H_7$-i | $OCH_2$ — 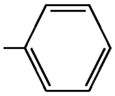 | O | O | H | CH | 141–144 |
| 21 | $CH_3$ | $COOC_2H_4C_3H_7$-i | OH | O | O | H | CH | 140.5–143 |
| 22 | $CH_3$ | $COOC_2H_4C_3H_7$-i | 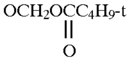 | O | O | H | CH | 1.5310 |
| 23 | $CH_3$ | $COOCH_3$ | $OCH_2$ — 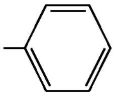 | O | O | H | CH | 1.5839 |
| 24 | $CH_3$ | $COOCH_3$ | OH | O | O | H | CH | 174–178 |
| 25 | $CH_3$ | $COOCH_3$ | $OCH_3$ | O | O | H | CH | |
| 26 | $CH_3$ | $COOCH_3$ | 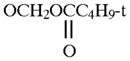 | O | O | H | CH | 126–130 |
| 27 | $CH_3$ | $COOCH_3$ | OH | S | O | H | CH | 219–223 6549 |
| 28 | $CH_3$ | $COOCH_3$ | 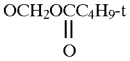 | S | O | H | CH | |
| 29 | $CH_3$ | $COOCH_3$ | $OCH_2$ — 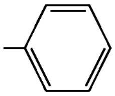 | S | O | H | CH | |
| 30 | $CH_3$ | $COOCH_3$ | OH | O | O | H | N | 182–185 |

TABLE 3

| Compound No. | $R^1$ | $R^2$ | R | W | X | Yn | Z | m.p. (°C.) or ($n_D^{20}$) |
|---|---|---|---|---|---|---|---|---|
| 31 | $CH_3$ | $COOCH_3$ | 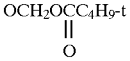 | O | O | H | N | 88–90 |
| 32 | $CH_3$ | $COOCH_3$ | $OCH_2$ — 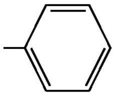 | O | O | H | N | 120–122 |
| 33 | $CH_3$ | $COOCH_3$ | OH | S | O | H | N | |
| 34 | $CH_3$ | $COOC_3H_7$ | OH | O | O | H | CH | 162–166 |
| 35 | $CH_3$ | $COOC_4H_9$-s | OH | O | O | H | CH | 144–147.5 |
| 36 | $CH_3$ | $COOC_4H_9$ | OH | O | O | H | CH | 160–164 |
| 37 | $CH_3$ | $CONH_2$ | OH | O | O | H | CH | |
| 38 | $CH_3$ | COOH | OH | O | O | H | CH | 186–188 |
| 39 | $CH_3$ | $COCH_3$ | $OCH_2$ — 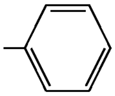 | O | O | H | CH | 62–65 |
| 40 | $CH_3$ | $COCH_3$ | OH | O | O | H | CH | 166–169 |
| 41 | $CH_3$ | $COCH_3$ | $OCH_3$ | O | O | H | CH | 178–181 |
| 42 | $CH_3$ | $COCH_3$ | 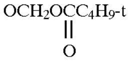 | O | O | H | CH | 122–125 |
| 43 | $CH_3$ | $COCH_3$ | $NHSO_2CH_3$ | O | O | H | CH | |

TABLE 3-continued
| Compound No. | $R^1$ | $R^2$ | R | W | X | Yn | Z | m.p. (°C.) or ($n_D^{20}$) |
|---|---|---|---|---|---|---|---|---|
| 44 | $CH_3$ | 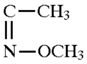 | $OCH_3$ | O | O | H | CH | 101–103 |
| 45 | $CH_3$ | 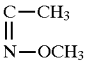 | 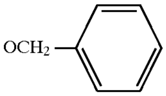 | O | O | H | CH | 1.5778 |
| 46 | $CH_3$ | 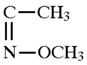 | OH | O | O | H | CH | |
| 47 | $CH_3$ | 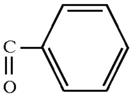 | 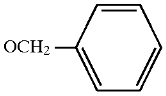 | O | O | H | CH | 120–123 |
| 48 | $CH_3$ | 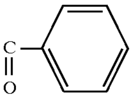 | OH | O | O | H | CH | 184–187 |
TABLE 4
| Compound No. | $R^1$ | $R^2$ | R | W | X | Yn | Z | m.p. (°C.) or ($n_D^{20}$) |
|---|---|---|---|---|---|---|---|---|
| 49 | $CH_3$ | 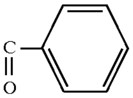 | $OCH_3$ | O | O | H | CH | 169–172 |
| 50 | $CH_3$ | 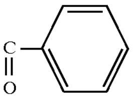 | 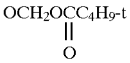 | O | O | H | CH | 115–117 |
| 51 | $CH_3$ | 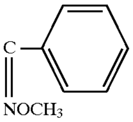 | $OCH_3$ | O | O | H | CH | 133–137 |
| 52 | $CH_3$ | 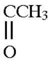 | $OCH_2OC_2H_5$ | O | O | H | CH | 127–130 |
| 53 | $CH_3$ | 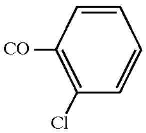 | $OCH_3$ | O | O | H | CH | 168–170.5 |
| 54 | $CH_3$ | 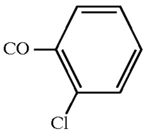 | OH | O | O | H | CH | |
| 55 | $CH_3$ | 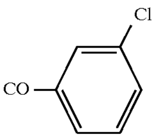 | $OCH_3$ | O | O | H | CH | 128–131 |

TABLE 4-continued

| Compound No. | $R^1$ | $R^2$ | R | W | X | Yn | Z | m.p. (°C.) or ($n_D^{20}$) |
|---|---|---|---|---|---|---|---|---|
| 56 | $CH_3$ | 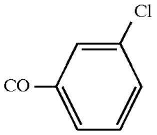 | OH | O | O | H | CH | |
| 57 | $CH_3$ | 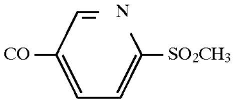 | $OCH_3$ | O | O | H | CH | 170–173.5 |
| 58 | $CH_3$ | 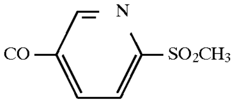 | OH | O | O | H | CH | |
| 59 | $CH_3$ | $COC_4H_9$-i | OH | O | O | H | CH | 168–171 |
| 60 | $CH_3$ | CN | OH | O | O | H | CH | 175–179 |

TABLE 5

| Compound No. | $R^1$ | $R^2$ | R | W | X | Yn | Z | m.p. (°C.) or ($n_D^{20}$) |
|---|---|---|---|---|---|---|---|---|
| 61 | H | $COOC_2H_5$ | OH | O | O | H | CH | 161–163 |
| 62 | H | $COOC_2H_5$ | 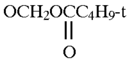 | O | O | H | CH | 1.5351 |
| 63 | H | $COOC_2H_5$ | 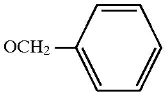 | O | O | H | CH | 91.5–93 |
| 64 | H | CN | OH | O | O | H | CH | |
| 65 | H | CN | 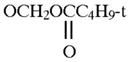 | O | O | H | CH | |
| 66 | H | CN | 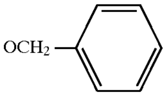 | O | O | H | CH | |
| 67 | $CF_3$ | $COOCH_3$ | OH | O | O | H | CH | |
| 68 | $CH_3$ | $COC_4H_9$-i | 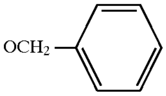 | O | O | H | CH | 1.5765 |
| 69 | $CF_3$ | 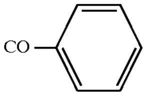 | $OCH_3$ | O | O | H | CH | 155–158 |
| 70 | $CF_3$ | 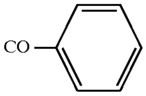 | OH | O | O | H | CH | 178–181 |
| 71 | $C_2H_5$ | $COOC_2H_5$ | OH | O | O | H | CH | 159.5–162 |
| 72 | $C_2H_5$ | $COOC_2H_5$ | 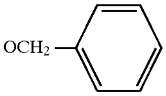 | O | O | H | CH | 116–120 |

TABLE 5-continued

| Compound No. | $R^1$ | $R^2$ | R | W | X | Yn | Z | m.p. (°C.) or ($n_D^{20}$) |
|---|---|---|---|---|---|---|---|---|
| 73 | $C_2H_5$ | $COOC_2H_5$ | $OCH_2OCC_4H_9$-t<br>‖<br>O | O | O | H | CH | 1.5339 |
| 74 | $C_2H_5$ | $COOC_3H_7$ | OH | O | O | H | CH | 119–122 |

TABLE 6

| Compound No. | $R^1$ | $R^2$ | R | W | X | Yn | Z | m.p. (°C.) or ($n_D^{20}$) |
|---|---|---|---|---|---|---|---|---|
| 75 | $C_2H_5$ | $COOC_3H_7$ | $OCH_2$ 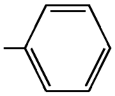 | O | O | H | CH | 108–109.5 |
| 76 | $C_2H_5$ | $COOC_3H_7$-i | OH | O | O | H | CH | 137–140 |
| 77 | $CF_3$ | CO 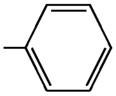 | $O^-$ $Na^+$ | O | O | H | CH | >300 |
| 78 | $CF_3$ | CO 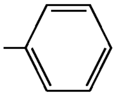 | $OCH_2OCC_4H_9$-t<br>‖<br>O | O | O | H | CH | 143–146 |
| 79 | $CH_2Cl$ | $COOC_2H_5$ | OH | O | O | H | CH | |
| 80 | $C_2H_5$ | $COOC_3H_7$-i | $OCH_2$ 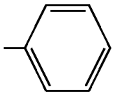 | O | O | H | CH | 94–96 |
| 81 | $CH_2Cl$ | $COOC_2H_5$ | $OCH_2OCC_4H_9$-t<br>‖<br>O | O | O | H | CH | |
| 82 | 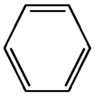 | $COCH_3$ | $OCH_3$ | O | O | H | CH | 151–154.5 |
| 83 | 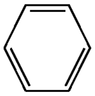 | $COCH_3$ | OH | O | O | H | CH | |
| 84 | 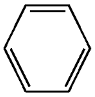 | CO 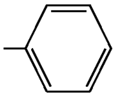 | $OCH_2$ 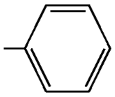 | O | O | H | CH | 176.5–180 |
| 85 | 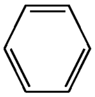 | CO 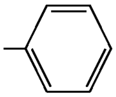 | OH | O | O | H | CH | 178.5–181 |
| 86 | 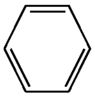 | CO 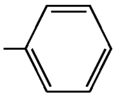 | $OCH_2OCC_4H_9$-t<br>‖<br>O | O | O | H | CH | Unmeasurable |

TABLE 7

| Compound No. | $R^1$ | $R^2$ | R | W | X | Yn | Z | m.p. (°C.) or ($n_D^{20}$) |
|---|---|---|---|---|---|---|---|---|
| 87 | 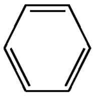 | $COOC_2H_5$ | $OCH_2$ 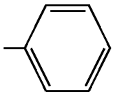 | O | O | H | CH | 85–90 |
| 88 | 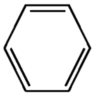 | $COOC_2H_5$ | OH | O | O | H | CH | 154–158 |
| 89 | 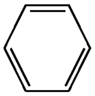 | $COOC_2H_5$ | $OCH_2OCC_4H_9$-t<br>‖<br>O | O | O | H | CH | 1.5730 |
| 90 | 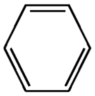 | CN | $OCH_2$ 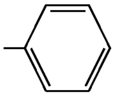 | O | O | H | CH | 152–156 |
| 91 | 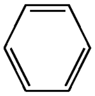 | CN | OH | O | O | H | CH | 165–169 |
| 92 | 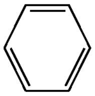 | CN | $OCH_3$ | O | O | H | CH | |
| 93 | 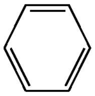 | CN | $OCH_2OCC_4H_9$-t<br>‖<br>O | O | O | H | CH | 143–146 |
| 94 | 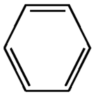 | $C-CH_3$<br>‖<br>$NOCH_3$ | $OCH_3$ | O | O | H | CH | 138–140 |
| 95 | 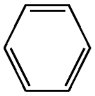 | $C-CH_3$<br>‖<br>$NOCH_3$ | OH | O | O | H | CH | |
| 96 | 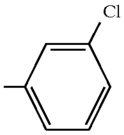 | $COCH_3$ | $OCH_3$ | O | O | H | CH | 137–141 |
| 97 | 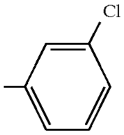 | $COCH_3$ | OH | O | O | H | CH | |

TABLE 8

| Compound No. | $R^1$ | $R^2$ | R | W | X | Yn | Z | m.p. (°C.) or ($n_D^{20}$) |
|---|---|---|---|---|---|---|---|---|
| 98 | $CH_3$ | $COOC_2H_5$ | OH | O | O | 7-Cl | CH | |
| 99 | $CH_3$ | $COOC_2H_5$ | OH | O | O | 7-$CH_3$ | CH | |
| 100 | $CH_3$ | $COOC_2H_5$ | OH | O | O | 6-Cl | CH | |
| 101 | $CH_3$ | $COOC_2H_5$ | OH | O | O | 6-$CH_3$ | CH | |
| 102 | $CH_3$ | $COOC_2H_5$ | OH | O | O | 7-$OCH_3$ | CH | |
| 103 | $CH_3$ | $COOC_2H_5$ | OH | O | O | 6-$N(CH_3)_2$ | CH | |
| 104 | H | $CH_3$ | H | O | S | H | CH | 158–161 |

TABLE 8-continued

| Compound No. | $R^1$ | $R^2$ | R | W | X | Yn | Z | m.p. (°C.) or ($n_D^{20}$) |
|---|---|---|---|---|---|---|---|---|
| 105 | H | $CH_3$ | OH | O | S | H | CH | 172–175 |
| 106 | H | $CH_3$ | $OCH_2OCC_4H_9$-t<br>‖<br>O | O | S | H | CH | |
| 107 | H | $CH_3$ | $OCH_3$ | O | S | H | CH | |
| 108 | $COOCH_3$ | $CH_3$ | H | O | S | H | CH | 201–206 |
| 109 | $COOCH_3$ | $CH_3$ | OH | O | S | H | CH | 154–158.5 |
| 110 | $COOCH_3$ | $CH_3$ | $OCH_2OCC_4H_9$-t<br>‖<br>O | O | S | H | CH | |
| 111 | $COOCH_3$ | $CH_3$ | $OCH_2$ 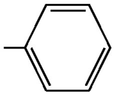 | O | S | H | CH | |
| 112 | $CH_3$ | $COOCH_3$ | OH | O | S | H | CH | 153–155 |
| 113 | $CH_3$ | $COOCH_3$ | $OCH_2$ 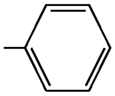 | O | S | H | CH | |
| 114 | $CH_3$ | $COOCH_3$ | $OCH_3$ | O | S | H | CH | |
| 115 | $CH_3$ | $COOCH_3$ | $OCH_2OCC_4H_9$-t<br>‖<br>O | O | S | H | CH | |
| 116 | $CH_3$ | $COOC_2H_5$ | OH | O | S | H | CH | 155–158 |
| 117 | H | H | OH | O | S | H | CH | |
| 118 | H | H | $OCH_2OCC_4H_9$-t<br>‖<br>O | O | S | H | CH | |

TABLE 9

| Compound No. | $R^1$ | $R^2$ | R | W | X | Yn | Z | m.p. (°C.) or ($n_D^{20}$) |
|---|---|---|---|---|---|---|---|---|
| 119 | H | H | $OCH_2$ 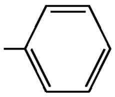 | O | S | H | CH | |
| 120 | H | H | $OCH_3$ | O | S | H | CH | |
| 121 | H | H | OH | O | S | H | N | |
| 122 | H | $CH_3$ | OH | O | S | H | N | |
| 123 | H | $CH_3$ | OH | S | S | H | CH | |
| 124 | H | $CH_3$ | OH | O | $NCH_3$ | H | CH | |
| 125 | H | $CH_3$ | OH | O | $NCH_3$ | H | N | |
| 126 | H | $CH_3$ | OH | S | $NCH_3$ | H | CH | |
| 127 | $COOCH_3$ | $CH_3$ | OH | O | $NCH_3$ | H | CH | |
| 128 | $CH_3$ | $COOCH_3$ | $NHSO_2$ 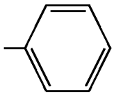 | O | O | H | CH | |
| 129 | $CH_3$ | $COOCH_3$ | $NHSO_2$ 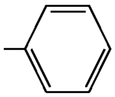 | O | O | H | N | |
| 130 | $CH_3$ | $COOCH_3$ | $O^-$ $Na^+$ | O | O | H | CH | >300 |

TABLE 9-continued

| Compound No. | $R^1$ | $R^2$ | R | W | X | Yn | Z | m.p. (°C.) or ($n_D^{20}$) |
|---|---|---|---|---|---|---|---|---|
| 131 | $CH_3$ | $COOC_2H_5$ | 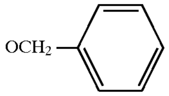 | O | NH | H | CH | 196–199 |
| 132 | $CH_3$ | $COOC_2H_5$ | OH | O | NH | H | CH | 202–204 |
| 133 | H | $COCH_3$ | OH | O | O | H | CH | |

TABLE 10

| Compound No. | $R^1$ | $R^2$ | R | W | X | Yn | Z | m.p. (°C.) or ($n_D^{20}$) |
|---|---|---|---|---|---|---|---|---|
| 134 | $CH_3$ | $COOC_2H_5$ | $SCH_3$ | O | O | H | CH | |
| 135 | $CH_3$ | $COOC_2H_5$ | $SC_2H_5$ | O | O | H | CH | |
| 136 | $CH_3$ | $COOC_2H_5$ | 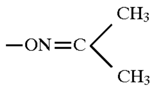 | O | O | H | CH | |
| 137 | $CH_3$ | $COOC_2H_5$ | OH | N(CHO) | O | H | CH | |
| 138 | $CH_3$ | $COOC_2H_5$ | OH | $CH_2$ | O | H | CH | |
| 139 | $CH_3$ | $COOC_2H_5$ | OH | CH(CN) | O | H | CH | |
| 140 | $CH_3$ | $COOCH_3$ | $NH_2$ | O | O | H | CH | |
| 141 | $CH_3$ | $COOCH_3$ | $NHCH_3$ | O | O | H | CH | |
| 142 | $CH_3$ | $COOC_2H_5$ | $N(CH_3)_2$ | O | O | H | CH | |
| 143 | $COCH_3$ | $CH_3$ | 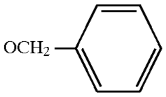 | O | O | H | CH | |
| 144 | $COCH_3$ | $CH_3$ | OH | O | O | H | CH | |
| 145 | $COCH_3$ | $CH_3$ | 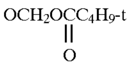 | O | O | H | CH | |
| 146 | $CH_3$ | 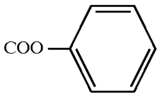 | 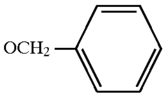 | O | O | H | CH | |
| 147 | $CH_3$ | 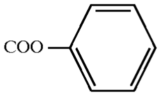 | OH | O | O | H | CH | 143–146 |
| 148 | $CH_3$ | 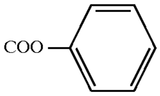 | 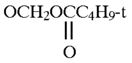 | O | O | H | CH | |
| 149 | $CH_3$ | $COSCH_3$ | $OCH_2CH{=}CH_2$ | O | O | H | CH | 134–136 |
| 150 | $CH_3$ | $COSCH_3$ | OH | O | O | H | CH | 163–165 |
| 151 | $CH_3$ | $COSCH_3$ | 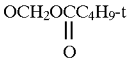 | O | O | H | CH | |
| 152 | $CH_3$ | $COSC_2H_5$ | $OCH_2CH{=}CH_2$ | O | O | H | CH | 102–105 |
| 153 | $CH_3$ | $COSC_2H_5$ | OH | O | O | H | CH | 149–152 |

TABLE 11

| Compound No. | $R^1$ | $R^2$ | R | W | X | Yn | Z | m.p. (°C.) or ($n_D^{20}$) |
|---|---|---|---|---|---|---|---|---|
| 154 | $CH_3$ | $COSC_2H_5$ | $OCH_2OCC_4H_9$-t<br>‖<br>O | O | O | H | CH | |
| 155 | $CH_3$ | $CONHCH_3$ | $OCH_2CH{=}CH_2$ | O | O | H | CH | |
| 156 | $CH_3$ | $CONHCH_3$ | OH | O | O | H | CH | |
| 157 | $CH_3$ | $CONHCH_3$ | $OCH_2OCC_4H_9$-t<br>‖<br>O | O | O | H | CH | |
| 158 | $CH_3$ | $CON(C_2H_5)_2$ | $OCH_2CH{=}CH_2$ | O | O | H | CH | 96–98 |
| 159 | $CH_3$ | $CON(C_2H_5)_2$ | OH | O | O | H | CH | 183–186 |
| 160 | $CH_3$ | $CON(C_2H_5)_2$ | $OCH_2OCC_4H_9$-t<br>‖<br>O | O | O | H | CH | |
| 161 | $CH_3$ | 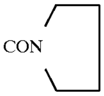 | $OCH_2CH{=}CH_2$ | O | O | H | CH | 85–88 |
| 162 | $CH_3$ | 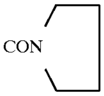 | OH | O | O | H | CH | 180–182.5 |
| 163 | $CH_3$ | 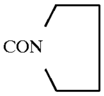 | $OCH_2OCC_4H_9$-t<br>‖<br>O | O | O | H | CH | |
| 164 | $CH_3$ | $COOC_3H_7$ | 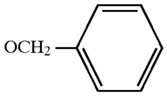 | O | O | H | CH | 132–136 |
| 165 | $CH_3$ | $COOC_3H_7$ | $OCH_2OCC_4H_9$-t<br>‖<br>O | O | O | H | CH | 108–109 |
| 166 | $CH_3$ | $COOC_4H_9$ | 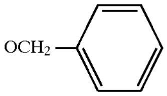 | O | O | H | CH | 135–136.5 |
| 167 | $CH_3$ | $COOC_4H_9$ | $OCH_2OCC_4H_9$-t<br>‖<br>O | O | O | H | CH | 1.5209 |

TABLE 12

| Compound No. | $R^1$ | $R^2$ | R | W | X | Yn | Z | m.p. (°C.) or ($n_D^{20}$) |
|---|---|---|---|---|---|---|---|---|
| 168 | $CH_3$ | $COOC_4H_9$-s | 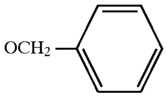 | O | O | H | CH | 149–150.5 |
| 169 | $CH_3$ | $COOC_4H_9$-s | $OCH_2OCC_4H_9$-t<br>‖<br>O | O | O | H | CH | 90–91.5 |
| 170 | $CH_3$ | $COOC_4H_9$-i | 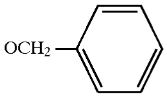 | O | O | H | CH | 152–156 |
| 171 | $CH_3$ | $COOC_4H_9$-i | OH | O | O | H | CH | 135–138 |

TABLE 12-continued

| Compound No. | $R^1$ | $R^2$ | R | W | X | Yn | Z | m.p. (°C.) or ($n_D^{20}$) |
|---|---|---|---|---|---|---|---|---|
| 172 | $CH_3$ | $COOC_4H_9$-i | $OCH_2OCC_4H_9$-t<br>‖<br>O | O | O | H | CH | 1.5276 |
| 173 | $CH_3$ | $COOC_4H_9$-t | 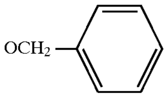 | O | O | H | CH | 170–172 |
| 174 | $CH_3$ | $COOC_4H_9$-t | OH | O | O | H | CH | 153–157 |
| 175 | $CH_3$ | $COOC_4H_9$-t | $OCH_2OCC_4H_9$-t<br>‖<br>O | O | O | H | CH | |
| 176 | $CH_3$ | $COOC_4H_9$-t | $OCH_2OC_2H_5$ | O | O | H | CH | |
| 177 | $CH_3$ | $COOC_5H_{11}$ | 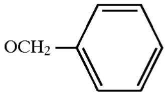 | O | O | H | CH | 115–116.5 |
| 178 | $CH_3$ | $COOC_5H_{11}$ | OH | O | O | H | CH | 140–144 |
| 179 | $CH_3$ | $COOC_5H_{11}$ | $OCH_2OCC_4H_9$-t<br>‖<br>O | O | O | H | CH | 1.5291 |
| 180 | $CH_3$ | $COOC_5H_{11}$ | $OCH_2OC_2H_5$ | O | O | H | CH | |
| 181 | $CH_3$ | $COOC_6H_{13}$ | 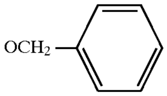 | O | O | H | CH | 99–101 |
| 182 | $CH_3$ | $COOC_6H_{13}$ | OH | O | O | H | CH | 153–159 |

TABLE 13

| Compound No. | $R^1$ | $R^2$ | R | W | X | Yn | Z | m.p. (°C.) or ($n_D^{20}$) |
|---|---|---|---|---|---|---|---|---|
| 183 | $CH_3$ | $COOC_6H_{13}$ | $OCH_2OCC_4H_9$-t<br>‖<br>O | O | O | H | CH | 1.5280 |
| 184 | $CH_3$ | $COOC_6H_{13}$ | $OCH_2OC_2H_5$ | O | O | H | CH | |
| 185 | $CH_3$ | $COOC_7H_{15}$ | 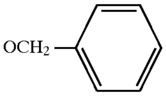 | O | O | H | CH | 78–80 |
| 186 | $CH_3$ | $COOC_7H_{15}$ | OH | O | O | H | CH | 145–149 |
| 187 | $CH_3$ | $COOC_7H_{15}$ | $OCH_2OCC_4H_9$-t<br>‖<br>O | O | O | H | CH | 1.5288 |
| 188 | $CH_3$ | $COOC_7H_{15}$ | $OCH_2OC_2H_5$ | O | O | H | CH | |
| 189 | $CH_3$ | $COOC_8H_{17}$ | 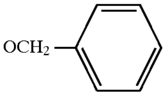 | O | O | H | CH | 105–108 |
| 190 | $CH_3$ | $COOC_8H_{17}$ | OH | O | O | H | CH | 148–151 |
| 191 | $CH_3$ | $COOC_8H_{17}$ | $OCH_2OCC_4H_9$-t<br>‖<br>O | O | O | H | CH | 1.5170 |

TABLE 13-continued

| Compound No. | $R^1$ | $R^2$ | R | W | X | Yn | Z | m.p. (°C.) or ($n_D^{20}$) |
|---|---|---|---|---|---|---|---|---|
| 192 | $CH_3$ | $COOCHC_3H_7$<br>\|<br>$CH_3$ | 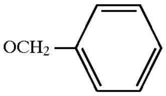 | O | O | H | CH | 99–101 |
| 193 | $CH_3$ | $COOCHC_3H_7$<br>\|<br>$CH_3$ | OH | O | O | H | CH | 130–132 |
| 194 | $CH_3$ | $COOCHC_3H_7$<br>\|<br>$CH_3$ | $OCH_2OCC_4H_9$-t<br>‖<br>O | O | O | H | CH | 1.5260 |
| 195 | $CH_3$ | $COOCHC_3H_7$<br>\|<br>$CH_3$ | $OCH_2OC_2H_5$ | O | O | H | CH | |
| 196 | $CH_3$ | $C_2H_5$<br>\|<br>COOCH<br>\|<br>$C_2H_5$ | 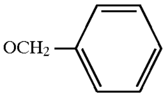 | O | O | H | CH | |
| 197 | $CH_3$ | $C_2H_5$<br>\|<br>COOCH<br>\|<br>$C_2H_5$ | OH | O | O | H | CH | 115–119 |

TABLE 14

| Compound No. | $R^1$ | $R^2$ | R | W | X | Yn | Z | m.p. (°C.) or ($n_D^{20}$) |
|---|---|---|---|---|---|---|---|---|
| 198 | $CH_3$ | $C_2H_5$<br>\|<br>COOCH<br>\|<br>$C_2H_5$ | $OCH_2OCC_4H_9$-t<br>‖<br>O | O | O | H | CH | |
| 199 | $CH_3$ | $C_2H_5$<br>\|<br>COOCH<br>\|<br>$C_2H_5$ | $OCH_2OC_2H_5$ | O | O | H | CH | |
| 200 | $CH_3$ | $CONHC_2H_5$ | 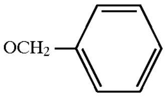 | O | O | H | CH | 147–149 |
| 201 | $CH_3$ | $CONHC_2H_5$ | OH | O | O | H | CH | 200–203 |
| 202 | $CH_3$ | $CONHC_2H_5$ | $OCH_2C{=}CH_2$ | O | O | H | CH | Unmeasurable |
| 203 | $CH_3$ | $COOC_3H_7$-i | 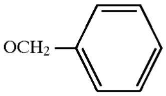 | O | O | H | CH | 140–143 |
| 204 | $CH_3$ | $COOC_3H_7$-i | OH | O | O | H | CH | 167–170 |
| 205 | $CH_3$ | $COOC_3H_7$-i | $OCH_2OCC_4H_9$-t<br>‖<br>O | O | O | H | CH | Unmeasurable |
| 206 | $CH_3$ | $COOC_3H_7$-i | $CH_3$<br>\|<br>$OCHOCC_4H_9$-t<br>‖<br>O | O | O | H | CH | |
| 207 | $CH_3$ | $COOC_3H_7$-i | $OCH_2OC_2H_5$ | O | O | H | CH | |
| 208 | $CH_3$ | $COOC_3H_7$-i | $O^- Na^+$ | O | O | H | CH | 208–210 |

TABLE 14-continued

| Compound No. | $R^1$ | $R^2$ | R | W | X | Yn | Z | m.p. (°C.) or ($n_D^{20}$) |
|---|---|---|---|---|---|---|---|---|
| 209 | $CH_3$ | $COOC_3H_7$-i | $OCH_2OC(=O)$— 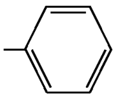 | O | O | H | CH | |
| 210 | $CH_3$ | COO— 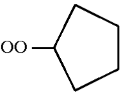 | $OCH_2$— 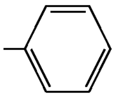 | O | O | H | CH | 183–184.5 |
| 211 | $CH_3$ | COO— 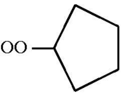 | OH | O | O | H | CH | 161–164.5 |

TABLE 15

| Compound No. | $R^1$ | $R^2$ | R | W | X | Yn | Z | m.p. (°C.) or ($n_D^{20}$) |
|---|---|---|---|---|---|---|---|---|
| 212 | $CH_3$ | COO— 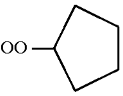 | $OCH_2OC(=O)C_4H_9$-t | O | O | H | CH | |
| 213 | $CH_3$ | COO— 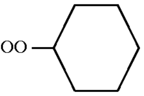 | $OCH_2$— 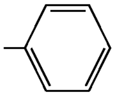 | O | O | H | CH | 194–196 |
| 214 | $CH_3$ | COO— 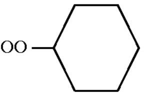 | OH | O | O | H | CH | 103–105 |
| 215 | $CH_3$ | $COOCH_2C(Cl)=CH_2$ | $OCH_2OC_2H_4Si(CH_3)_3$ | O | O | H | CH | 1.5334 |
| 216 | $CH_3$ | $COOCH_2C(Cl)=CH_2$ | OH | O | O | H | CH | 142–144 |
| 217 | $CH_3$ | $COOCH_2C(Cl)=CH_2$ | $OCH_2OC(=O)C_4H_9$-t | O | O | H | CH | |
| 218 | $CH_3$ | $COOCH_2CH=CH_2$ | $OCH_2$— 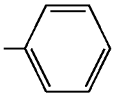 | O | O | H | CH | 101.5–104 |
| 219 | $CH_3$ | $COOCH_2CH=CH_2$ | OH | O | O | H | CH | 163–165 |
| 220 | $CH_3$ | $COOCH_2CH=CH_2$ | $OCH_2OC(=O)C_4H_9$-t | O | O | H | CH | |
| 221 | $CH_3$ | $COOCH_2CH=CH_2$ | $OCH_2OC_2H_4Si(CH_3)_3$ | O | O | H | CH | 1.5322 |
| 222 | $CH_3$ | $COOCH_2C\equiv CH$ | $OCH_2$— 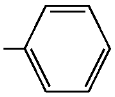 | O | O | H | CH | |

TABLE 15-continued

| Compound No. | $R^1$ | $R^2$ | R | W | X | Yn | Z | m.p. (°C.) or ($n_D^{20}$) |
|---|---|---|---|---|---|---|---|---|
| 223 | $CH_3$ | $COOCH_2C{\equiv}CH$ | OH | O | O | H | CH | 155–158 |
| 224 | $CH_3$ | $COOCH_2C{\equiv}CH$ | $OCH_2CH{=}CH_2$ | O | O | H | CH | 93–95 |

TABLE 16

| Compound No. | $R^1$ | $R^2$ | R | W | X | Yn | Z | m.p. (°C.) or ($n_D^{20}$) |
|---|---|---|---|---|---|---|---|---|
| 225 | $CH_3$ | $COOCH_2C{\equiv}CH$ | $CH_3$<br>\|<br>$OCH_2OC_2H_4SiCH_3$<br>\|<br>$CH_3$ | O | O | H | CH | 70–73 |
| 226 | $CH_3$ | $COSC_3H_7$ | $OCH_2CH{=}CH_2$ | O | O | H | CH | 77–79 |
| 227 | $CH_3$ | $COSC_3H_7$ | OH | O | O | H | CH | 130–133 |
| 228 | $CH_3$ | $COSC_3H_7$ | $OCH_2OCC_4H_9$-t<br>\|\|<br>O | O | O | H | CH | |
| 229 | $CH_3$ | $COSC_3H_7$ | $OCH_2OC_2H_5$ | O | O | H | CH | |
| 230 | $CH_3$ | $COSC_3H_7$-i | $OCH_2CH{=}CH_2$ | O | O | H | CH | 105–108 |
| 231 | $CH_3$ | $COSC_3H_7$-i | OH | O | O | H | CH | 160–163 |
| 232 | $CH_3$ | $COSC_5H_{11}$ | $OCH_2CH{=}CH_2$ | O | O | H | CH | 1.5621 |
| 233 | $CH_3$ | $COSC_5H_{11}$ | OH | O | O | H | CH | 132–134 |
| 234 | $CH_3$ | $COSC_4H_9$ | $OCH_2CH{=}CH_2$ | O | O | H | CH | 1.5665 |
| 235 | $CH_3$ | $COSC_4H_9$ | OH | O | O | H | CH | 127–130 |
| 236 | $CH_3$ | $COSC_4H_9$ | $OCH_2OCC_4H_9$-t<br>\|\|<br>O | O | O | H | CH | 104–106 |
| 237 | $CH_3$ | $COSC_4H_9$-i | $OCH_2CH{=}CH_2$ | O | O | H | CH | 75–77 |
| 238 | $CH_3$ | $COSC_4H_9$-i | OH | O | O | H | CH | |
| 239 | $CH_3$ | $COSC_4H_9$-i | $OCH_2OCC_4H_9$-t<br>\|\|<br>O | O | O | H | CH | |
| 240 | $CH_3$ | $COSC_4H_9$-t | $OCH_2CH{=}CH_2$ | O | O | H | CH | |
| 241 | $CH_3$ | $COSC_4H_9$-t | OH | O | O | H | CH | 126–128 |
| 242 | $CH_3$ | $COSC_4H_9$-t | $OCH_2OCC_4H_9$-t<br>\|\|<br>O | O | O | H | CH | |
| 243 | $CH_3$ | COS 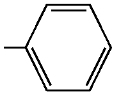 | $OCH_2CH{=}CH_2$ | O | O | H | CH | |
| 244 | $CH_3$ | COS 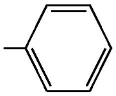 | OH | O | O | H | CH | |
| 245 | $CH_3$ | COS 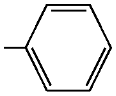 | $OCH_2OCC_4H_9$-t<br>\|\|<br>O | O | O | H | CH | |

TABLE 17

| Compound No. | $R^1$ | $R^2$ | R | W | X | Yn | Z | m.p. (°C.) or ($n_D^{20}$) |
|---|---|---|---|---|---|---|---|---|
| 246 | $CH_3$ | $CON(CH_3)_2$ | $OCH_2$ 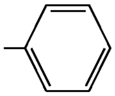 | O | O | H | CH | Unmeasurable |
| 247 | $CH_3$ | $CON(CH_3)_2$ | OH | O | O | H | CH | 185–187 |
| 248 | $CH_3$ | $CON(CH_3)_2$ | $OCH_2CH{=}CH_2$ | O | O | H | CH | Unmeasurable |
| 249 | $CH_3$ | CONH 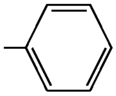 | $OCH_2$ 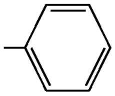 | O | O | H | CH | |
| 250 | $CH_3$ | CONH 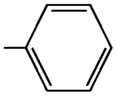 | OH | O | O | H | CH | 171–174 |
| 251 | $CH_3$ | CONH 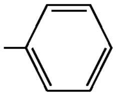 | $OCH_2O\overset{O}{\overset{\|}{C}}C_4H_9$-t | O | O | H | CH | |
| 252 | $CH_3$ | $COOC_2H_5$ | S 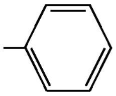 | O | O | H | CH | |
| 253 | $CH_3$ | $COOC_2H_5$ | O 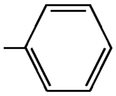 | O | O | H | CH | |
| 254 | $CH_3$ | COCl | $OCH_2CH{=}CH_2$ | O | O | H | CH | 75–78 |
| 255 | $CH_3$ | COCl | $OCH_2$ 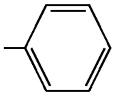 | O | O | H | CH | 136–140 |
| 256 | Cl | $COOC_2H_5$ | OH | O | O | H | CH | |
| 257 | $COOC_2H_5$ | Cl | OH | O | O | H | CH | |
| 258 | $CH_3$ | $COOCH_2$ 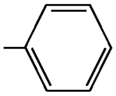 | $OCH_2CH{=}CH_2$ | O | O | H | CH | 95–97 |
| 259 | $CH_3$ | $COOCH_2$ 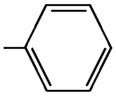 | OH | O | O | H | CH | 144.5–147 |
| 260 | $CH_3$ | $COOCH_2$ 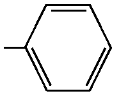 | $OCH_2OC_2H_4\overset{CH_3}{\underset{CH_3}{Si}}CH_3$ | O | O | H | CH | |

TABLE 18

| Compound No. | $R^1$ | $R^2$ | R | W | X | Yn | Z | m.p. (°C.) or ($n_D^{20}$) |
|---|---|---|---|---|---|---|---|---|
| 261 | $CH_3$ | $COSCH_2CH{=}CH_2$ | $OCH_2$ 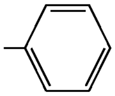 | O | O | H | CH | |
| 262 | $CH_3$ | $COSCH_2CH{=}CH_2$ | OH | O | O | H | CH | 1.5786 |

TABLE 18-continued

| Compound No. | $R^1$ | $R^2$ | R | W | X | Yn | Z | m.p. (°C.) or ($n_D^{20}$) |
|---|---|---|---|---|---|---|---|---|
| 263 | $CH_3$ | $COSCH_2CH=CH_2$ | $OCH_2OCC_4H_9$-t<br>‖<br>O | O | O | H | CH | |
| 264 | $CH_3$ | $COSCH_2C\equiv CH$ | $CH_3$<br>\|<br>$OCH_2OC_2H_4SiCH_3$<br>\|<br>$CH_3$ | O | O | H | CH | |
| 265 | $CH_3$ | $COSCH_2C\equiv CH$ | OH | O | O | H | CH | |
| 266 | $CH_3$ | $COSCH_2C\equiv CH$ | $OCH_2OCC_4H_9$-t<br>‖<br>O | O | O | H | CH | |
| 267 | $C_3H_7$ | $COOC_2H_5$ | $OCH_2$— 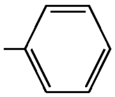 | O | O | H | CH | 102.5–105 |
| 268 | $C_3H_7$ | $COOC_2H_5$ | OH | O | O | H | CH | 140.5–144 |
| 269 | $C_3H_7$ | $COOC_2H_5$ | $OCH_2OCC_4H_9$-t<br>‖<br>O | O | O | H | CH | 1.5291 |
| 270 | $C_2H_5$ | $COOCH_3$ | $OCH_2$— 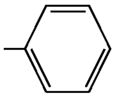 | O | O | H | CH | 115–117 |
| 271 | $C_2H_5$ | $COOCH_3$ | OH | O | O | H | CH | 164–167 |
| 272 | $C_2H_5$ | COOH | $OCH_2$— 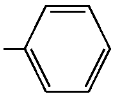 | O | O | H | CH | 185–188 |
| 273 | $C_3H_7$-i | $COOC_2H_5$ | $OC_2H_5$ | O | O | H | CH | 1.5459 |
| 274 | $C_3H_7$-i | $COOC_2H_5$ | OH | O | O | H | CH | 157–159 |
| 275 | $C_3H_7$-i | $COOC_2H_5$ | $OCH_2OCC_4H_9$-t<br>‖<br>O | O | O | H | CH | 1.5318 |
| 276 | $C_2H_5$ | $COOC_2H_5$ | $OC_2H_5$ | O | O | H | CH | 1.5490 |
| 277 | $C_3H_7$ | $COOC_2H_5$ | $OC_2H_5$ | O | O | H | CH | 1.5431 |

TABLE 19

| Compound No. | $R^1$ | $R^2$ | R | W | X | Yn | Z | m.p. (°C.) or ($n_D^{20}$) |
|---|---|---|---|---|---|---|---|---|
| 278 | $CH_3$ | $COOC_3H_6Cl$ | OH | O | O | H | CH | 161–165 |
| 279 | $CH_3$ | $COOC_3H_6Cl$ | $OCH_2$— 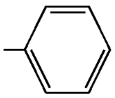 | O | O | H | CH | 124–125 |
| 280 | $CH_3$ | $COOC_2H_4F$ | OH | O | O | H | CH | 152–155 |
| 281 | $CH_3$ | $COOC_2H_4F$ | $OCH_2$— 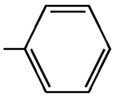 | O | O | H | CH | 114–117 |
| 282 | $CH_3$ | $COOC_3H_6Br$ | $OCH_2$— 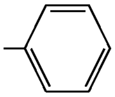 | O | O | H | CH | 124–127 |

TABLE 19-continued

| Compound No. | $R^1$ | $R^2$ | R | W | X | Yn | Z | m.p. (°C.) or ($n_D^{20}$) |
|---|---|---|---|---|---|---|---|---|
| 283 | $CH_3$ | $COOC_3H_6Br$ | OH | O | O | H | CH | |
| 284 | $CH_3$ | 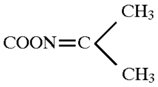 | $OCH_2C{=}CH_2$ | O | O | H | CH | 138–140 |
| 285 | H | $COOCH_3$ | 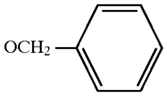 | O | O | H | CH | |
| 286 | H | $COOCH_3$ | OH | O | O | H | CH | 150–153 |
| 287 | H | $COOCH_3$ | 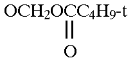 | O | O | H | CH | |
| 288 | H | $COOC_3H_7$ | 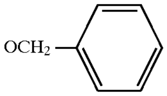 | O | O | H | CH | |
| 289 | H | $COOC_3H_7$ | OH | O | O | H | CH | 158–161 |
| 290 | H | $COOC_3H_7$ | 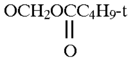 | O | O | H | CH | |
| 291 | H | $COOC_3H_7$-i | 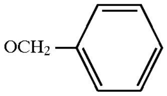 | O | O | H | CH | 80–82 |
| 292 | H | $COOC_3H_7$-i | OH | O | O | H | CH | 140–143.5 |
| 293 | H | $COOC_3H_7$-i | 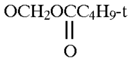 | O | O | H | CH | |

TABLE 20

| Compound No. | $R^1$ | $R^2$ | R | W | X | Yn | Z | m.p. (°C.) or ($n_D^{20}$) |
|---|---|---|---|---|---|---|---|---|
| 294 | H | $COOC_4H_9$ | 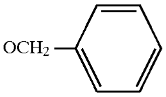 | O | O | H | CH | 82–84 |
| 295 | H | $COOC_4H_9$ | OH | O | O | H | CH | 134–137 |
| 296 | H | $COOC_4H_9$ | 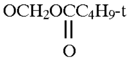 | O | O | H | CH | |
| 297 | H | $COOC_4H_9$-i | 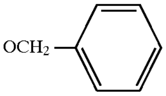 | O | O | H | CH | 95–98 |
| 298 | H | $COOC_4H_9$-i | OH | O | O | H | CH | 140–144 |
| 299 | H | $COOC_4H_9$-i | 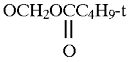 | O | O | H | CH | |
| 300 | H | $COOC_4H_9$-s | 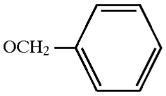 | O | O | H | CH | 91–93 |

TABLE 20-continued

| Compound No. | $R^1$ | $R^2$ | R | W | X | Yn | Z | m.p. (°C.) or ($n_D^{20}$) |
|---|---|---|---|---|---|---|---|---|
| 301 | H | $COOC_4H_9$-s | OH | O | O | H | CH | Unmeasurable |
| 302 | H | $COOC_4H_9$-s | $OCH_2OCC_4H_9$-t<br>‖<br>O | O | O | H | CH | |
| 303 | H | $COOC_4H_9$-t | 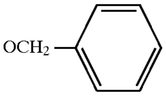 | O | O | H | CH | |
| 304 | H | $COOC_4H_9$-t | OH | O | O | H | CH | |
| 305 | H | $COOC_4H_9$-t | $OCH_2OCC_4H_9$-t<br>‖<br>O | O | O | H | CH | |
| 306 | H | $COOC_5H_{11}$ | 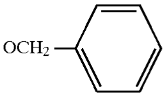 | O | O | H | CH | 88–90 |
| 307 | H | $COOC_5H_{11}$ | OH | O | O | H | CH | 117–119 |
| 308 | H | $COOC_5H_{11}$ | $OCH_2OCC_4H_9$-t<br>‖<br>O | O | O | H | CH | |

TABLE 21

| Compound No. | $R^1$ | $R^2$ | R | W | X | Yn | Z | m.p. (°C.) or ($n_D^{20}$) |
|---|---|---|---|---|---|---|---|---|
| 309 | H | $COOC_6H_{13}$ | 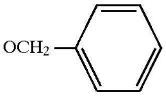 | O | O | H | CH | |
| 310 | H | $COOC_6H_{13}$ | OH | O | O | H | CH | |
| 311 | H | $COOC_6H_{13}$ | $OCH_2OCC_4H_9$-t<br>‖<br>O | O | O | H | CH | |
| 312 | H | 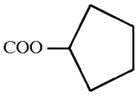 | 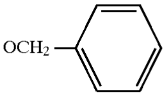 | O | O | H | CH | |
| 313 | H | 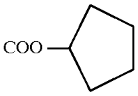 | OH | O | O | H | CH | |
| 314 | H | 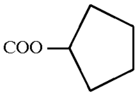 | $OCH_2OCC_4H_9$-t<br>‖<br>O | O | O | H | CH | |
| 315 | $CH_3$ | $CONHC_3H_7$-i | 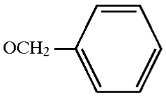 | O | O | H | CH | Unmeasurable |
| 316 | $CH_3$ | $CONHC_3H_7$-i | OH | O | O | H | CH | 173—176 |
| 317 | $CH_3$ | $CONHC_3H_7$-i | $OCH_2CH{=}CH_2$ | O | O | H | CH | 157–159.5 |
| 318 | $CH_3$ | 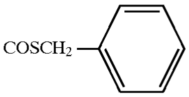 | $OCH_2CH{=}CH_2$ | O | O | H | CH | 137–139 |

TABLE 21-continued

| Compound No. | $R^1$ | $R^2$ | R | W | X | Yn | Z | m.p. (°C.) or ($n_D^{20}$) |
|---|---|---|---|---|---|---|---|---|
| 319 | $CH_3$ | 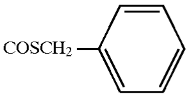 | OH | O | O | H | CH | 137–138 |
| 320 | $CH_3$ | 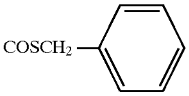 | $OCH_2O\underset{\underset{O}{\|}}{C}C_4H_9$-t | O | O | H | CH | |
| 321 | $CH_3$ | $COOCH_2C_4H_9$-t | 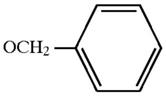 | O | O | H | CH | 162–165 |
| 322 | $CH_3$ | $COOCH_2C_4H_9$-t | OH | O | O | H | CH | 137–140 |
| 323 | $CH_3$ | $COOCH_2C_4H_9$-t | $OCH_2O\underset{\underset{O}{\|}}{C}C_4H_9$-t | O | O | H | CH | |

TABLE 22

| Compound No. | $R^1$ | $R^2$ | R | W | X | Yn | Z | m.p. (°C.) or ($n_D^{20}$) |
|---|---|---|---|---|---|---|---|---|
| 324 | $CH_3$ | $COOCH_2C_4H_9$-t | $OCH_2OC_2H_5$ | O | O | H | CH | |
| 325 | $CH_3$ | 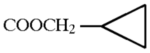 | 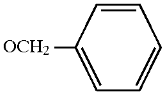 | O | O | H | CH | 149–151 |
| 326 | $CH_3$ | 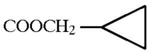 | OH | O | O | H | CH | 146–148 |
| 327 | $CH_3$ | 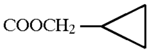 | $OCH_2O\underset{\underset{O}{\|}}{C}C_4H_9$-t | O | O | H | CH | 1.5330 |
| 328 | $CH_3$ | 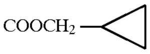 | $OCH_2OC_2H_5$ | O | O | H | CH | |
| 329 | $CH_3$ | 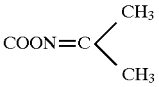 | OH | O | O | H | CH | 173–175 |
| 330 | $CH_3$ | $COOC_3H_7$ | $O^-$ $Na^+$ | O | O | H | CH | |
| 331 | $CH_3$ | $COOC_3H_7$ | 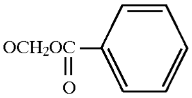 | O | O | H | CH | |
| 332 | $CH_3$ | $COOC_3H_7$ | $OCH_2CH{=}CH_2$ | O | O | H | CH | |
| 333 | $CH_3$ | $COOC_3H_7$ | 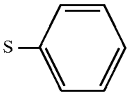 | O | O | H | CH | |
| 334 | $CH_3$ | $COOC_3H_7$ | $N(CH_3)_2$ | O | O | H | CH | |
| 335 | $CH_3$ | $COOC_3H_7$ | $O^-CH_3\underset{\underset{CH_3}{\|}}{C}H{-}NH_3^+$ | O | O | H | CH | |
| 336 | $CH_3$ | 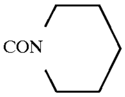 | 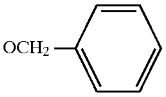 | O | O | H | CH | Unmeasurable |

TABLE 22-continued

| Compound No. | $R^1$ | $R^2$ | R | W | X | Yn | Z | m.p. (°C.) or ($n_D^{20}$) |
|---|---|---|---|---|---|---|---|---|
| 337 | $CH_3$ | 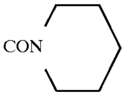 | OH | O | O | H | CH | 138–143 |

TABLE 23

| Compound No. | $R^1$ | $R^2$ | R | W | X | Yn | Z | m.p. (°C.) or ($n_D^{20}$) |
|---|---|---|---|---|---|---|---|---|
| 338 | $CH_3$ | 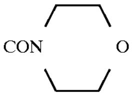 | OH | O | O | H | CH | |
| 339 | $CH_3$ | $COOCH_2OC_2H_5$ | 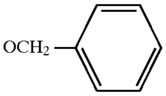 | O | O | H | CH | 110–113 |
| 340 | $CH_3$ | $COOCH_2OC_2H_5$ | OH | O | O | H | CH | 152–154 |
| 341 | $CH_3$ | $COOC_2H_4SCH_3$ | OH | O | O | H | CH | 140–143 |
| 342 | $CH_3$ | $COOC_2H_4SCH_3$ | $OCH_2CH{=}CH_2$ | O | O | H | CH | 64–66 |
| 343 | $CH_3$ | $COOCH(CF_3)_2$ | 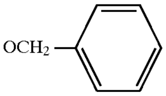 | O | O | H | CH | 158–160.5 |
| 344 | $CH_3$ | $COOCH(CF_3)_2$ | OH | O | O | H | CH | 137–140 |
| 345 | $CH_3$ | $COOCH_3$ | $O^- H_3^+NCH(CH_3)_2$ | O | O | H | CH | 133.5–137 |
| 346 | $CH_3$ | 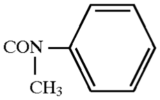 | OH | O | O | H | CH | 189–191 |
| 347 | $CH_3$ | $COOC_2H_4OCH_3$ | 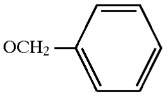 | O | O | H | CH | 105–107 |
| 348 | $CH_3$ | $COOC_2H_4OCH_3$ | OH | O | O | H | CH | 138–142 |
| 349 | $CH_3$ | $COOC_2H_4OCH_3$ | $OCH_2OCC_4H_9$-t<br>‖<br>O | O | O | H | CH | |
| 350 | 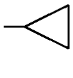 | $COOCH_3$ | 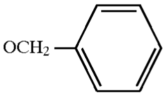 | O | O | H | CH | |
| 351 | 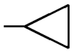 | $COOCH_3$ | OH | O | O | H | CH | |
| 352 | 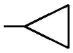 | $COOCH_3$ | $OCH_2OCC_4H_9$-t<br>‖<br>O | O | O | H | CH | |

TABLE 24

| Compound No. | $R^1$ | $R^2$ | R | W | X | Yn | Z | m.p. (°C.) or ($n_D^{20}$) |
|---|---|---|---|---|---|---|---|---|
| 353 | 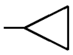 | $COOCH_3$ | $OCH_2OC_2H_5$ | O | O | H | CH | |
| 354 | $CH_3$ | $COOCH_2SCH_3$ | $OCH_2CH{=}CH_2$ | O | O | H | CH | 99–101 |
| 355 | $CH_3$ | $COOCH_2SCH_3$ | OH | O | O | H | CH | 152–155.5 |
| 356 | $CH_3$ | $COOCH_2CF_3$ | OH | O | O | H | CH | 152.5–155 |
| 357 | $CH_3$ | $COOCH_2CF_3$ | $OCH_2CH{=}CH_2$ | O | O | H | CH | 114–116 |
| 358 | $CH_3$ | $COOCH_2CF_3$ | 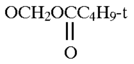 | O | O | H | CH | |
| 359 | $CH_3$ | COOH | 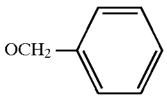 | O | O | H | CH | 222–225 |
| 360 | $CH_3$ | $COC_2H_5$ | 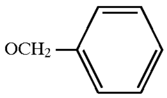 | O | O | H | CH | |
| 361 | $CH_3$ | $COC_2H_5$ | OH | O | O | H | CH | |
| 362 | $CH_3$ | $COC_3H_7$ | 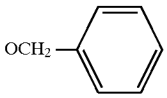 | O | O | H | CH | |
| 363 | $CH_3$ | $COC_3H_7$ | OH | O | O | H | CH | |
| 364 | $CH_3$ | $COC_4H_9$ | 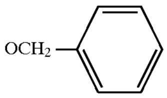 | O | O | H | CH | 119–121 |
| 365 | $CH_3$ | $COC_4H_9$ | OH | O | O | H | CH | 136–138 |
| 366 | $CH_3$ | $COC_5H_{11}$ | 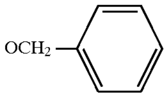 | O | O | H | CH | 106–109 |
| 367 | $CH_3$ | $COC_5H_{11}$ | OH | O | O | H | CH | 130–132 |
| 368 | $CH_3$ | 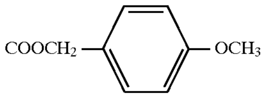 | OH | O | O | H | CH | Unmeasurable |
| 369 | $CH_3$ | 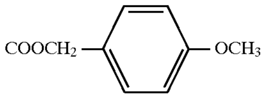 | 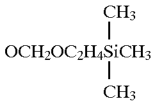 | O | O | H | CH | 1.5519 |

TABLE 25

| Compound No. | $R^1$ | $R^2$ | R | W | X | Yn | Z | m.p. (°C.) or ($n_D^{20}$) |
|---|---|---|---|---|---|---|---|---|
| 370 | $CH_3$ | COOH | 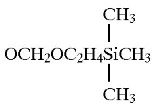 | O | O | H | CH | 132–135 |
| 371 | $CH_3$ | COOH | $OCH_2CH{=}CH_2$ | O | O | H | CH | 207–210 |
| 372 | H | $COOCH_2C_4H_9$-t | OH | O | O | H | CH | |
| 373 | H | $COSC_2H_5$ | OH | O | O | H | CH | |
| 374 | H | $CONHC_2H_5$ | OH | O | O | H | CH | |
| 375 | H | $CON(CH_3)_2$ | OH | O | O | H | CH | |
| 376 | H | $COSC_3H_7$ | OH | O | O | H | CH | |

TABLE 25-continued

| Compound No. | $R^1$ | $R^2$ | R | W | X | Yn | Z | m.p. (°C.) or ($n_D^{20}$) |
|---|---|---|---|---|---|---|---|---|
| 377 | H | $COSC_4H_9$ | OH | O | O | H | CH | |
| 378 | $CH_3OCH_2$ | $COOCH_3$ | $OCH_2$— 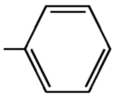 | O | O | H | CH | 92–95 |
| 379 | $CH_3OCH_2$ | $COOCH_3$ | OH | O | O | H | CH | 150–153 |
| 380 | $CH_3OCH_2$ | $COOC_2H_5$ | $OCH_2O\overset{O}{\overset{\|}{C}}C_4H_9$-t | O | O | H | CH | |
| 381 | $CH_3OC_2H_4$ | $COOCH_3$ | $OCH_2$— 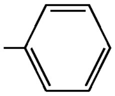 | O | O | H | CH | |
| 382 | $CH_3OC_2H_4$ | $COOCH_3$ | OH | O | O | H | CH | |
| 383 | $CH_3OC_2H_4$ | $COOCH_3$ | $OCH_2O\overset{O}{\overset{\|}{C}}C_4H_9$-t | O | O | H | CH | |

TABLE 26

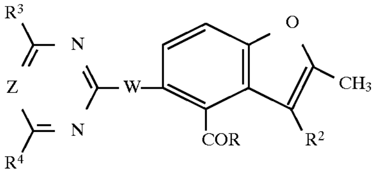

| Compound No. | $R^2$ | $R^3$ | $R^4$ | R | W | Z | m.p. (°C.) or ($n_D^{20}$) |
|---|---|---|---|---|---|---|---|
| 384 | $COOCH_3$ | $CH_3$ | $CH_3$ | $OCH_2$— 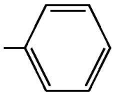 | O | CH | 145–147 |
| 385 | $COOCH_3$ | $CH_3$ | $CH_3$ | OH | O | CH | 174–177 |
| 386 | $COOCH_3$ | $CH_3$ | $OCH_3$ | OH | O | CH | 138–140 |
| 387 | $COOCH_3$ | $CH_3$ | Cl | OH | O | CH | |
| 388 | $COOCH_3$ | $CH_3$ | $OCH_3$ | $OCH_2$— 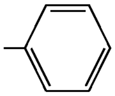 | O | CH | 102.5–106 |
| 389 | $COOCH_3$ | $CH_3$ | $OCH_3$ | OH | O | N | 143–146 |
| 390 | $COOCH_3$ | $CH_3$ | $OCH_3$ | $OCH_2$— 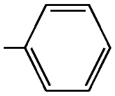 | O | N | 117–120 |
| 391 | $COOCH_3$ | $OCH_3$ | Cl | OH | O | CH | 162–164 |
| 392 | $COOCH_3$ | $OCH_3$ | $NHCH_3$ | OH | O | CH | |
| 393 | $COOCH_3$ | $OCH_3$ | $OCHF_2$ | OH | O | CH | 151–155 |
| 394 | $COOCH_3$ | $OCHF_2$ | $OCHF_2$ | OH | O | CH | |
| 395 | $COOCH_3$ | $OCH_3$ | $N(CH_3)_2$ | OH | O | CH | 167–170 |
| 396 | $COOCH_3$ | $CH_3$ | $CH_3$ | $OCH_2O\overset{O}{\overset{\|}{C}}C_4H_9$-t | O | N | |
| 397 | $COOCH_3$ | $CH_3$ | $OCH_3$ | $OCH_2O\overset{O}{\overset{\|}{C}}C_4H_9$-t | O | CH | |

TABLE 26-continued

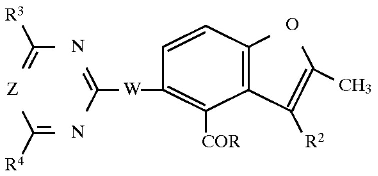

| Compound No. | $R^2$ | $R^3$ | $R^4$ | R | W | Z | m.p. (°C.) or ($n_D^{20}$) |
|---|---|---|---|---|---|---|---|
| 398 | $COOCH_3$ | Cl | $OCH_3$ | $OCH_2$ 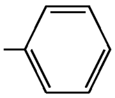 | O | CH | 129–132 |

TABLE 27

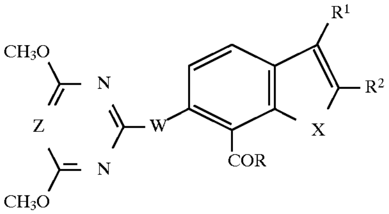

| Compound No. | $R^1$ | $R^2$ | R | W | X | Z | m.p. (°C.) or ($n_D^{20}$) |
|---|---|---|---|---|---|---|---|
| 399 | H | H | H | O | S | CH | |
| 400 | H | H | OH | O | S | CH | |
| 401 | H | H | $OCH_2O\underset{\underset{O}{\|}}{C}C_4H_9$-t | O | S | CH | |
| 402 | H | H | H | O | $NCH_3$ | CH | |
| 403 | H | H | OH | O | $NCH_3$ | CH | |
| 404 | H | H | $OCH_2O\underset{\underset{O}{\|}}{C}C_4H_9$-t | O | $NCH_3$ | CH | |
| 405 | H | $COOC_2H_5$ | H | O | O | CH | 116–124 |
| 406 | H | $COOC_2H_5$ | OH | O | O | CH | |
| 407 | H | $COOC_2H_5$ | $OCH_2O\underset{\underset{O}{\|}}{C}C_4H_9$-t | O | O | CH | |
| 408 | CH | $COOC_2H_5$ | H | O | O | CH | |
| 409 | $CH_3$ | $COOC_2H_5$ | OH | O | O | CH | |
| 410 | H | $COOC_2H_5$ | OH | O | $NCH_3$ | CH | |
| 411 | H | $COOC_2H_5$ | OH | O | S | CH | |
| 412 | $COOC_2H_5$ | H | H | O | O | CH | |
| 413 | $COOC_2H_5$ | H | OH | O | O | CH | |
| 414 | $COOC_2H_5$ | H | H | O | $NCH_3$ | CH | |
| 415 | $COOC_2H_5$ | H | H | O | $NCH_3$ | N | |
| 416 | $COOC_2H_5$ | $CH_3$ | OH | O | O | CH | |
| 417 | $COOC_2H_5$ | H | OH | O | $NCH_3$ | CH | |
| 418 | $COOC_2H_5$ | H | H | O | S | CH | |
| 419 | $COOC_2H_5$ | H | OH | O | S | CH | |
| 420 | $COOC_2H_5$ | H | H | O | S | CH | |
| 421 | $COOC_2H_5$ | H | OH | O | S | CH | |
| 422 | H | $CH_3$ | $OCH_2$ 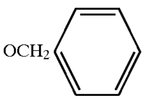 | O | $NCH_3$ | CH | |

TABLE 28

| Compound No. | $R^1$ | $R^2$ | R | W | X | Z | m.p. (°C.) or ($n_D^{20}$) |
|---|---|---|---|---|---|---|---|
| 423 | H | $CH_3$ | OH | O | $NCH_3$ | CH | |
| 424 | H | H | $OCH_2OCH_3$ | O | $NCH_2CH{=}CH_2$ | CH | |
| 425 | H | H | OH | O | $NCH_2CH{=}CH_2$ | CH | |
| 426 | H | $CH_3$ | $OCH_2OCH_3$ | O | $NCH_2CH{=}CH_2$ | CH | |
| 427 | H | $CH_3$ | OH | O | $NCH_2CH{=}CH_2$ | CH | |
| 428 | H | $CH_3$ | $OCH_2CH{=}CH_2$ | O | $NCH_2COOCH_3$ | CH | |
| 429 | H | $CH_3$ | OH | O | $NCH_2COOCH_3$ | CH | |
| 430 | H | $CH_3$ | 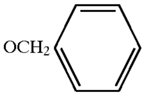 | O | $NC({=}O)CH_3$ | CH | |
| 431 | H | $CH_3$ | OH | O | $NC({=}O)CH_3$ | CH | |
| 432 | H | $CH_3$ | 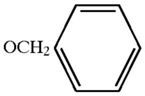 | O | 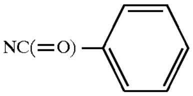 | CH | |
| 433 | H | $CH_3$ | OH | O | 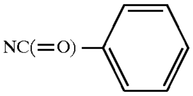 | CH | |
| 434 | H | $CH_3$ | 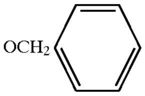 | O | $NCOOC_2H_5$ | CH | |
| 435 | H | $CH_3$ | OH | O | $NCOOC_2H_5$ | CH | |
| 436 | H | $CH_3$ | 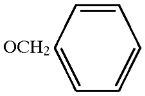 | O | 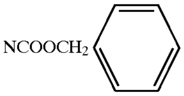 | CH | |
| 437 | H | $CH_3$ | OH | O | 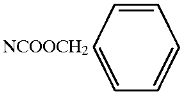 | CH | |
| 438 | H | $CH_3$ | 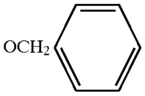 | O | 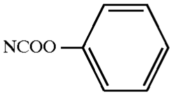 | CH | |
| 439 | H | $CH_3$ | OH | O | 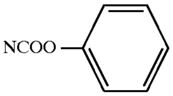 | CH | |
| 440 | H | $CH_3$ | $OCH_2CH{=}CH_2$ | O | $NSO_2CH_3$ | CH | |
| 441 | H | $CH_3$ | OH | O | $NSO_2CH_3$ | CH | |
| 442 | H | $CH_3$ | 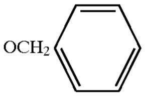 | O | NH | CH | |
| 443 | H | $CH_3$ | OH | O | NH | CH | |
| 444 | H | $CH_3$ | OH | O | NH | N | |

TABLE 29

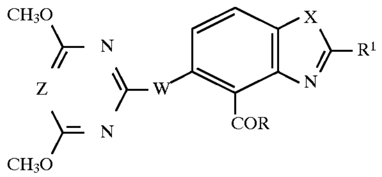

| Compound No. | $R^1$ | R | W | X | Z | m.p. (°C.) or ($n_D^{20}$) |
|---|---|---|---|---|---|---|
| 445 | H | 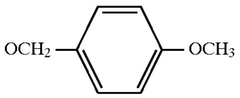 | O | O | CH | Unmeasurable |
| 446 | H | $OCH_3$ | O | O | CH | 144–148 |
| 447 | H | OH | O | O | CH | |
| 448 | H | OH | O | O | N | |
| 449 | H | OH | S | O | CH | |
| 450 | H | OH | S | O | N | |
| 451 | $CH_3$ | OH | O | O | CH | |
| 452 | $C_2H_5$ | OH | O | O | CH | |
| 453 | 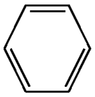 | OH | O | O | CH | |
| 454 | H | OH | O | NH | CH | |
| 455 | $CH_3$ | OH | O | NH | CH | |
| 456 | H | OH | O | NH | N | |
| 457 | H | OH | O | S | CH | |
| 458 | $CH_3$ | OH | O | S | CH | |
| 459 | H | OH | O | S | N | |
| 460 | $CH_3$ | OH | O | S | N | |

TABLE 30

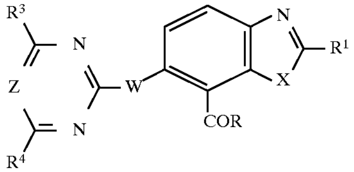

| Compound No. | $R^1$ | $R^3$ | $R^4$ | R | W | X | Z | m.p. (°C.) or ($n_D^{20}$) |
|---|---|---|---|---|---|---|---|---|
| 461 | H | $OCH_3$ | $OCH_3$ | $OC_2H_5$ | O | O | CH | 111–114 |
| 462 | H | $OCH_3$ | $OCH_3$ | $OCH_3$ | O | O | CH | 125–127 |
| 463 | H | $OCH_3$ | $OCH_3$ | OH | O | O | CH | 168–174 |
| 464 | H | $OCH_3$ | $OCH_3$ | $OCH_3$ | O | O | N | 141–144 |
| 465 | H | $OCH_3$ | $OCH_3$ | OH | O | O | N | |
| 466 | H | $OCH_3$ | $OCH_3$ | OH | S | O | CH | |
| 467 | H | $OCH_3$ | $OCH_3$ | OH | S | O | N | |
| 468 | $CH_3$ | $OCH_3$ | $OCH_3$ | $OCH_3$ | O | O | CH | 162–165 |
| 469 | $CH_3$ | $OCH_3$ | $OCH_3$ | OH | O | O | CH | 204–210 |
| 470 | $CH_3$ | $OCH_3$ | $OCH_3$ | OH | O | O | N | |
| 471 | $CH_3$ | $OCH_3$ | $OCH_3$ | OH | S | O | CH | |
| 472 | H | $OCH_3$ | $OCH_3$ | $OC_2H_4Si(CH_3)_3$ | O | O | CH | 1.5343 |
| 473 | $CH_3$ | $OCH_3$ | $OCH_3$ | $OCH_2OC_2H_5$ | O | O | N | |
| 474 | $C_2H_5$ | $OCH_3$ | $OCH_3$ | OH | O | O | CH | |
| 475 | 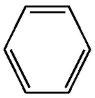 | $OCH_3$ | $OCH_3$ | OH | O | O | CH | 210–211 |
| 476 | H | $CH_3$ | $CH_3$ | $OCH_3$ | O | O | CH | 1.5582 |
| 477 | H | $OCH_3$ | $OCH_3$ | $OCH_2OC_2H_5$ | O | O | CH | Unmeasurable |
| 478 | H | $OCH_3$ | $OCH_3$ | OH | O | S | CH | |
| 479 | $CH_3$ | $OCH_3$ | $OCH_3$ | OH | O | S | CH | |

TABLE 30-continued

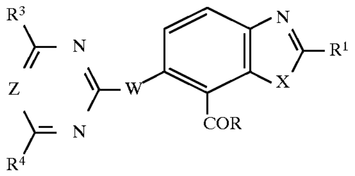

| Compound No. | $R^1$ | $R^3$ | $R^4$ | R | W | X | Z | m.p. (°C.) or ($n_D^{20}$) |
|---|---|---|---|---|---|---|---|---|
| 480 | H | $OCH_3$ | $OCH_3$ | OH | O | S | N | |
| 481 | $CH_3$ | $OCH_3$ | $OCH_3$ | OH | O | S | N | |
| 482 | $CH_2NO_2$ | $OCH_3$ | $OCH_3$ | OH | O | S | CH | 168–169 |
| 483 | $CH_3$ | $OCH_3$ | $OCH_3$ | OH | CH(CN) | O | CH | |

TABLE 31

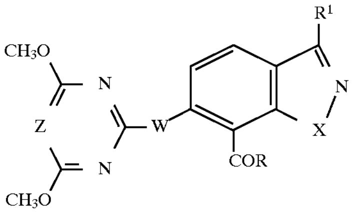

| Compound No. | $R^1$ | R | W | X | Z | m.p. (°C.) or ($n_D^{20}$) |
|---|---|---|---|---|---|---|
| 484 | H | OH | O | O | CH | |
| 485 | H | OH | S | O | CH | |
| 486 | H | OH | O | O | N | |
| 487 | $CH_3$ | $OCH_3$ | O | O | CH | 167–171 |
| 488 | $CH_3$ | OH | O | O | CH | 155–159 |
| 489 | $CH_3$ | OH | O | O | N | |
| 490 | $CH_3$ | OH | S | O | N | |
| 491 | $CH_3$ | OH | S | O | CH | |
| 492 | H | OH | O | S | CH | |
| 493 | H | OH | O | S | N | |
| 494 | H | OH | O | NH | CH | |
| 495 | H | OH | O | $NCH_3$ | CH | |

TABLE 32

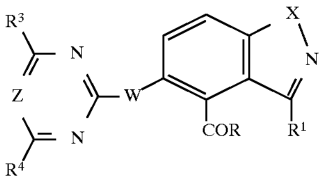

| Compound No. | $R^1$ | $R^3$ | $R^4$ | R | W | X | Z | m.p. (°C.) or ($n_D^{20}$) |
|---|---|---|---|---|---|---|---|---|
| 496 | H | $OCH_3$ | $OCH_3$ | OH | O | O | CH | |
| 497 | H | $OCH_3$ | $OCH_3$ | OH | S | O | CH | |
| 498 | H | $OCH_3$ | $OCH_3$ | OH | O | NH | CH | 169–171 |
| 499 | $CH_3$ | $OCH_3$ | $OCH_3$ | OH | O | O | CH | |
| 500 | $CH_3$ | $OCH_3$ | $OCH_3$ | OH | O | O | N | |
| 501 | $CH_3$ | $OCH_3$ | $OCH_3$ | OH | S | O | N | |

TABLE 32-continued

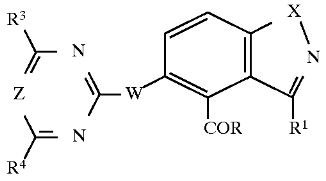

| Compound No. | $R^1$ | $R^3$ | $R^4$ | R | W | X | Z | m.p. (°C.) or ($n_D^{20}$) |
|---|---|---|---|---|---|---|---|---|
| 502 | $CH_3$ | $CH_3$ | $CH_3$ | OH | O | O | CH | |
| 503 | $CH_3$ | $CH_3$ | $OCH_3$ | OH | O | O | CH | |
| 504 | H | $OCH_3$ | $OCH_3$ | OH | O | S | CH | |
| 505 | H | $OCH_3$ | $OCH_3$ | OH | O | S | N | |
| 506 | H | $OCH_3$ | $OCH_3$ | OH | O | $NCOCH_3$ | CH | 175–178 |

TABLE 33

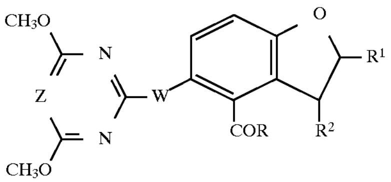

| Compound No. | $R^1$ | $R^2$ | R | W | Z | m.p. (°C.) or ($n_D^{20}$) |
|---|---|---|---|---|---|---|
| 507 | $OC_2H_5$ | H | $OCH_3$ | O | CH | 1.5243 |
| 508 | $OC_2H_5$ | H | OH | O | CH | 1.5306 |
| 509 | $CH_3$ | H | $OCH_3$ | O | CH | 1.5319 |
| 510 | $CH_3$ | H | OH | O | CH | Unmeasurable |
| 511 | $CH_3$ | H | $OCH_3$ | O | N | |
| 512 | $CH_3$ | H | OH | O | N | |
| 513 | $CH_3$ | H | $OCH_3$ | S | CH | |
| 514 | $CH_3$ | H | OH | S | CH | |
| 515 | $OC_2H_5$ | H | $OCH_3$ | O | N | |
| 516 | $OC_2H_5$ | H | OH | O | N | |
| 517 | $OC_2H_5$ | H | OH | S | CH | |
| 518 | $OC_2H_5$ | H | OH | S | N | |

TABLE 33-continued

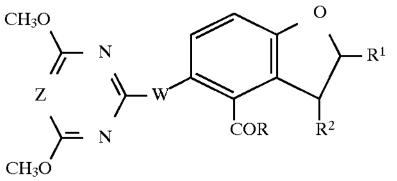

| Compound No. | $R^1$ | $R^2$ | R | W | Z | m.p. (°C.) or ($n_D^{20}$) |
|---|---|---|---|---|---|---|
| 519 | $OC_2H_5$ | $CH_3$ | $OCH_2$ 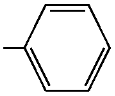 | O | CH | 1.5575 |
| 520 | $OC_2H_5$ | $CH_3$ | OH | O | CH | 105–109 |
| 521 | $OC_2H_5$ | $CH_3$ | $OCH_2OCC_4H_9$-t<br>‖<br>O | O | CH | |
| 522 | $OC_2H_5$ | CN | $OCH_2$ 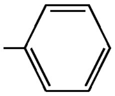 | O | CH | |
| 523 | $OC_2H_5$ | CN | OH | O | CH | |
| 524 | $OC_2H_5$ | CN | $OCH_2OCC_4H_9$-t<br>‖<br>O | O | CH | |

TABLE 33-continued

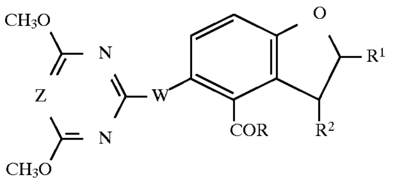

| Compound No. | $R^1$ | $R^2$ | R | W | Z | m.p. (°C.) or ($n_D^{20}$) |
|---|---|---|---|---|---|---|
| 525 | $OC_2H_5$ | $COCH_3$ | $OCH_2$ 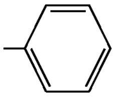 | O | CH | |
| 526 | $OC_2H_5$ | $COCH_3$ | OH | O | CH | |
| 527 | $OC_2H_5$ | $COCH_3$ | $OCH_2OCC_4H_9$-t<br>‖<br>O | O | CH | |

TABLE 34

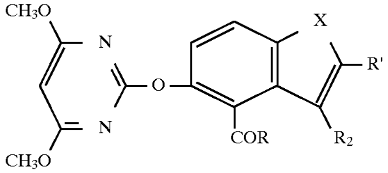

| Compound No. | $R^1$ | $R^2$ | R | X | m.p. (°C.) or ($n_D^{20}$) |
|---|---|---|---|---|---|
| 528 | $CH_3$ | $COOC_2H_4SCH_3$ | $OCH_2OCOC_4H_9$-t | O | 69–71 |
| 529 | $CH_3$ | COOH | $OCH_2OC_2H_4OCH_3$ | O | 139–141 |
| 530 | $CH_3$ | $COOCH_2CH{=}CHCH_3$ | $OCH_2OC_2H_4OCH_3$ | O | 1.5441 |
| 531 | $CH_3$ | $COOCH_2CH{=}CHCl$ | $OCH_2OC_2H_4OCH_3$ | O | Unmeasurable |
| 532 | $CH_3$ | $COOCH_2CCl{=}CHCl$ | $OCH_2OC_2H_4OCH_3$ | O | 1.5488 |
| 533 | $CH_3$ | $COOCH_2CH{=}CHCH_3$ | OH | O | 143–144 |
| 534 | $CH_3$ | $COOCH_2CH{=}CHCl$ | OH | O | 146–148 |
| 535 | $CH_3$ | $COOCH_2CCl{=}CHCl$ | OH | O | 155–158 |
| 536 | $CH_3$ | CONH 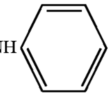 | $OCH_2CH{=}CH_2$ | O | 191–194 |
| 537 | $CH_3$ | $CON(CH_3)$ 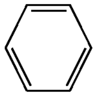 | $OCH_2CH{=}CH_2$ | O | 128–131 |
| 538 | $CH_3$ | $CONHC_3H_7$-i | $OCH_2OCOC_4H_9$-t | O | 183–184.5 |
| 539 | $CH_3$ | $COSC_5H_{11}$ | $OCH(CH_3)OCOC_4H_9$-t | O | 1.5380 |

TABLE 34-continued

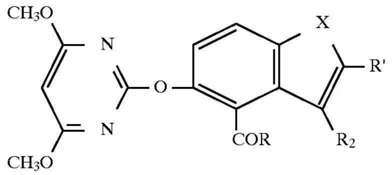

| Compound No. | $R^1$ | $R^2$ | R | X | m.p. (°C.) or ($n_D^{20}$) |
|---|---|---|---|---|---|
| 540 | $CH_3$ | $COON{=}C(CH_3)_2$ | $OCH(CH_3)OCOC_4H_9$-t | O | 186–189 |
| 541 | H | $COOCH_2CH{=}CH_2$ | $OCH_2$ 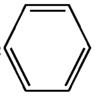 | O | 85–87 |
| 542 | H | COOH | $OCH_2$ 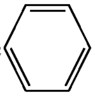 | O | 174–175 |
| 543 | $CH_3$ | CON 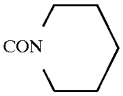 | $OCH_2CH{=}CH_2$ | O | 114–116 |
| 544 | $CH_3$ | $CONHC_4H_9$ | $OCH_2CH{=}CH_2$ | O | 148–150 |
| 545 | $CH_3$ | $COOCH_2C(CH_3){=}CH_2$ | $OCH_2OC_2H_4OCH_3$ | O | 1.5438 |
| 546 | $CH_3$ | $COOCH(CH_3)CH{=}CH_2$ | $OCH_2OC_2H_4OCH_3$ | O | 1.5373 |
| 547 | $CH_3$ | $COOCH_2CH{=}C(CH_3)_2$ | $OCH_2OC_2H_4OCH_3$ | O | 1.5461 |
| 548 | $CH_3$ | $COOCH_2C{\equiv}CCH_3$ | $OCH_2OC_2H_4OCH_3$ | O | 69–71 |
| 549 | $CH_3$ | $COOCH_2CH_2C{\equiv}CH$ | $OCH_2OC_2H_4OCH_3$ | O | 66–68 |
| 550 | $CH_3$ | $COOCH(CH_3)C{\equiv}CH$ | $OCH_2OC_2H_4OCH_3$ | O | 1.5420 |
| 551 | $CH_3$ | $COOCH(CH_3)CH{=}CH_2$ | OH | O | 140–144.5 |

TABLE 35

| Compound No. | $R^1$ | $R^2$ | R | X | m.p. (°C.) or ($n_D^{20}$) |
|---|---|---|---|---|---|
| 552 | $CH_3$ | $COOCH_2C{\equiv}CCH_3$ | OH | O | 174–178 |
| 553 | $CH_3$ | $COOCH_2CH_2C{\equiv}CH$ | OH | O | Unmeasurable |
| 554 | $CH_3$ | $COOCH(CH_3)C{\equiv}CH$ | OH | O | 160–165 |
| 555 | $CH_3$ | $COSCH(CH_3)C_2H_5$ | $OCH_2CH{=}CH_2$ | O | 100–103 |
| 556 | $CH_3$ | $COOC_3H_7$ | $OCH(CH_3)OCOC_4H_9$ | O | 102–106 |
| 557 | $CH_3$ | $COOC_3H_7$ | $OCH(CH_3)OCOC_4H_9$-t | O | 126–129 |
| 558 | $CH_3$ | $CONHC_4H_9$ | OH | O | 177–179 |
| 559 | $CH_3$ | $CON(CH_3)C_4H_9$ | $OCH_2CH{=}CH_2$ | O | 1.5465 |
| 560 | $CH_3$ | $CON(CH_3)C_4H_9$ | OH | O | 162–166 |
| 561 | $CH_3$ | $CONHCH_2$ 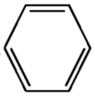 | $OCH_2CH{=}CH_2$ | O | 218–220 |
| 562 | $CH_3$ | $COSC_4H_9$-i | OH | O | 130–133 |
| 563 | $CH_3$ | $CONHCH_2$ 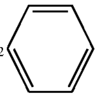 | OH | O | 158–163 |
| 564 | $CH_3$ | $COOCH_2C{\equiv}CC_2H_5$ | $OCH_2OCH_3$ | O | 95–97 |

TABLE 35-continued

| Compound No. | $R^1$ | $R^2$ | R | X | m.p. (°C.) or ($n_D^{20}$) |
|---|---|---|---|---|---|
| 565 | $CH_3$ | $COOCH_2CH_2C\equiv CCH_3$ | $OCH_2OCH_3$ | O | 140.5–143 |
| 566 | $CH_3$ | $COOCH_2CH_2CH_2C\equiv CH$ | $OCH_2OCH_3$ | O | 78–81 |
| 567 | $CH_3$ | $COOCH(CH_3)CH_2C\equiv CH$ | $OCH_2OCH_3$ | O | 137–138.5 |
| 568 | $CH_3$ | $COOCH(C_2H_5)C\equiv CH$ | $OCH_2OCH_3$ | O | 138–140 |
| 569 | $CH_3$ | $COSCH_2CH=CH_2$ | $OCH_2OCH_3$ | O | 1.5850 |
| 570 | $CH_3$ | $COOCH_2C\equiv CC_2H_5$ | OH | O | 167–169 |
| 571 | $CH_3$ | $COOCH_2CH_2C\equiv CCH_3$ | OH | O | Unmeasurable |
| 572 | $CH_3$ | $COOCH_2CH_2CH_2C\equiv CH$ | OH | O | 160–161.5 |
| 573 | $CH_3$ | $COOCH(CH_3)CH_2C\equiv CH$ | OH | O | 133–135 |
| 574 | $CH_3$ | $COOCH(C_2H_5)C\equiv CH$ | OH | O | 155–156.5 |
| 575 | $C_2H_5$ | COOH | OH | O | 171–174.5 |
| 576 | $CH_3$ | $COOC_3H_7$ | $OCH(CH_3)OCOC_2H_5$ | O | 104.5–107 |
| 577 | $CH_3$ | $COOC_3H_7$ | $OCH(CH_3)OCOC_3H_7$ | O | 104–105.5 |
| 578 | $CH_3$ | $COOC_3H_7$ | $OCH(CH_3)OCOC_3H_7$-i | O | 123–126 |
| 579 | $CH_3$ | $COOC_3H_7$ | $OCH(CH_3)OCOC_4H_9$-i | O | 124.5–126.5 |

TABLE 36

| Compound No. | $R^1$ | $R^2$ | R | X | m.p. (°C.) or ($n_D^{20}$) |
|---|---|---|---|---|---|
| 580 | $CH_3$ | COS 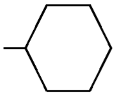 | $OCH_2CH=CH_2$ | O | 97–99 |
| 581 | $CH_3$ | COS 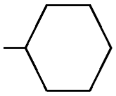 | OH | O | 110–114 |
| 582 | $CH_3$ | $COOCH_2CH_2Cl$ | $OCH_2CH=CH_2$ | O | 99–101 |
| 583 | $CH_3$ | $COOCH_2CHCl_2$ | $OCH_2CH=CH_2$ | O | 97–98 |
| 584 | $CH_3$ | $COOCH_2CCl_3$ | $OCH_2CH=CH_2$ | O | 126–128.5 |
| 585 | $CH_3$ | $COOCH_2CH_2Cl$ | OH | O | 155–157 |
| 586 | $CH_3$ | $COOCH_2CHCl_2$ | OH | O | 129–132 |
| 587 | $CH_3$ | $COOCH_2CCl_3$ | OH | O | 97–101 |
| 588 | $CH_3$ | $COOCH_2CH_2Br$ | $OCH_2CH=CH_2$ | O | 106–108 |
| 589 | $CH_3$ | $COOCH_2CH_2CN$ | $OCH_2CH=CH_2$ | O | 128–130 |
| 590 | $CH_3$ | $COOCH_2CH_2Br$ | OH | O | 159–162 |
| 591 | $CH_3$ | $COOCH_2CH_2CN$ | OH | O | 177–179.5 |
| 592 | $CH_3$ | $COOCH(CF_3)_2$ | $OCH_2CH=CH_2$ | O | 139–141 |
| 593 | $CH_3$ | $COOCH_2$ 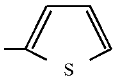 | $OCH_2CH=CH_2$ | O | 85–89 |
| 594 | $CH_3$ | $COOCH_2$ 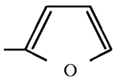 | $OCH_2CH=CH_2$ | O | 98–101.5 |
| 595 | $CH_3$ | $COOCH_2$ 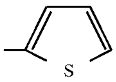 | OH | O | 160–162 |
| 596 | $CH_3$ | $COOCH_2$ 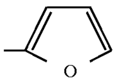 | OH | O | 155–158 |
| 597 | $CH_3$ | $COSCH_2CH_2CH(CH_3)_2$ | $OCH_2CH=CH_2$ | O | 72–74 |
| 598 | $CH_3$ | $COSCH_2CH_2CH(CH_3)_2$ | OH | O | 99–101 |

TABLE 36-continued

| Compound No. | $R^1$ | $R^2$ | R | X | m.p. (°C.) or ($n_D^{20}$) |
|---|---|---|---|---|---|
| 599 | $CH_3$ | $COSCH_2CH_2N(C_2H_5)_2$ | $OCH_2CH{=}CH_2$ | O | 68–69.5 |
| 600 | $CH_3$ | $COSCH_2CH_2N(C_2H_5)_2$ | OH | O | 139–142 |
| 601 | H | $COOCH_2$ | OH | O | 158–163 |
| 602 | $C_2H_5$ | $COC_2H_5$ 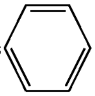 | $OCH_2$ 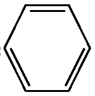 | O | 110–112 |

TABLE 37

| Compound No. | $R^1$ | $R^2$ | R | X | m.p. (°C.) or ($n_D^{20}$) |
|---|---|---|---|---|---|
| 603 | $C_2H_5$ | $COC_2H_5$ | OH | O | 140.5–143 |
| 604 | $C_4H_9$ | $COCH_3$ | OH | O | 134–136 |
| 605 | H | $COOCH_2$ 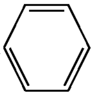 | $OCH_2CH{=}CH_2$ | O | 100–103 |
| 606 | $CH_3$ | H | $OCH_2CH{=}CH_2$ | S | 89–91 |
| 607 | $CH_3$ | H | OH | S | 151–155 |
| 608 | $CH_3$ | $COOC_2H_5$ | $OCH_2$ 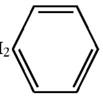 | $NCH_3$ | 151–156 |
| 609 | $CH_3$ | $COOC_2H_5$ | OH | $NCH_3$ | 200–202 |
| 610 | $CH_3$ | $COOC_4H_9$-t | $OCH_2$ 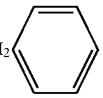 | NH | 183–187 |
| 611 | $CH_3$ | $COOC_4H_9$-t | OH | NH | 187–190 |
| 612 | $CH_3$ | H | OH | NH | 167–170 |
| 613 | $CH_3$ | $COOCH_3$ | $OCH_2$ 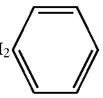 | NH | 164–166 |
| 614 | $CH_3$ | $COOCH_3$ | OH | NH | 194–197 |
| 615 | $CH_3$ | $COOCH_2CH{=}CH_2$ | $OCH_2$ 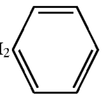 | NH | 204–208 |
| 616 | $CH_3$ | COOH | $OCH_2$ 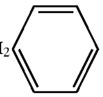 | NH | 161–164 |
| 617 | $CH_3$ | $COOC_3H_7$ | OH | NH | 175–179 |
| 618 | $CH_3$ | $COOC_3H_7$-i | OH | NH | 180–183 |
| 619 | $CH_3$ | $COOC_4H_9$ | OH | NH | 143–148 |
| 620 | $CH_3$ | $COOC_4H_9$-i | OH | NH | 140–146.5 |
| 621 | $CH_3$ | $COOC_4H_9$-s | OH | NH | 145–150 |
| 622 | $CH_3$ | $COOC_5H_{11}$ | OH | NH | 119–123 |
| 623 | $CH_3$ | $COOC_6H_{13}$ | OH | NH | 125–130 |

TABLE 37-continued
| Compound No. | $R^1$ | $R^2$ | R | X | m.p. (°C.) or ($n_D^{20}$) |
|---|---|---|---|---|---|
| 624 | $CH_3$ | $COOC_3H_7$ | 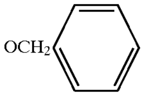 | NH | 207–209 |
TABLE 38
| Compound No. | $R^1$ | $R^2$ | R | X | m.p. (°C.) or ($n_D^{20}$) |
|---|---|---|---|---|---|
| 625 | $CH_3$ | $COOC_3H_7$-i | 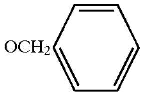 | NH | 203–205 |
| 626 | $CH_3$ | $COOC_4H_9$ | 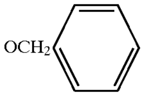 | NH | 191.5–194 |
| 627 | $CH_3$ | $COOC_4H_9$-i | 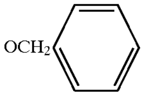 | NH | 200–203 |
| 628 | $CH_3$ | $COOC_4H_9$-s | 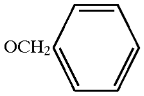 | NH | 170–173 |
| 629 | $CH_3$ | $COOC_5H_{11}$ | 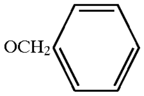 | NH | 137–139 |
| 630 | $CH_3$ | $COOC_6H_{13}$ | 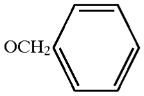 | NH | 130–133 |
| 631 | $CH_3$ | 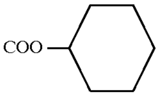 | 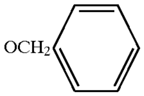 | NH | 181–184 |
| 632 | $CH_3$ | 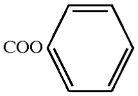 | 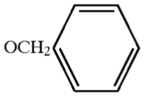 | NH | 192.5–196 |
| 633 | $CH_3$ | $COOCH_2CH_2OCH_3$ | 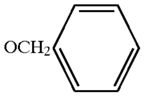 | NH | 187–190 |
| 634 | $CH_3$ | $COCF_3$ | OH | NH | 162–167 |
| 635 | $CH_3$ | $COCF_3$ | 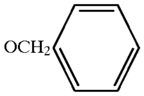 | NH | 165–167 |
| 636 | $CH_3$ | 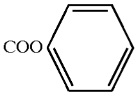 | OH | NH | 223–227 |
| 637 | $CH_3$ | $COOCH_2CH_2OCH_3$ | OH | NH | 182–186 |

TABLE 38-continued

| Compound No. | $R^1$ | $R^2$ | R | X | m.p. (°C.) or ($n_D^{20}$) |
|---|---|---|---|---|---|
| 638 | $CH_3$ | Cl | OH | NH | 176–179 |
| 639 | $CH_3$ | $COC_2H_5$ | OH | NH | 192–195 |
| 640 | $CH_3$ | $COC_2H_5$ | $OCH_2$ 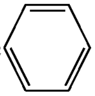 | NH | 173–176 |
| 641 | $CH_3$ | CN | $OCH_2$ 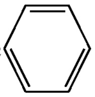 | NH | 151–154 |

TABLE 39

| Compound No. | $R^1$ | $R^2$ | R | X | m.p. (°C.) or ($n_D^{20}$) |
|---|---|---|---|---|---|
| 642 | $CH_3$ | $COCH_3$ | OH | NH | 198–203 |
| 643 | $CH_3$ | $COCH_3$ | $OCH_2$ 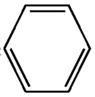 | NH | 206–211 |
| 644 | $CH_3$ | CN | $OCH_2$ 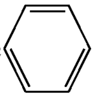 | O | 156–158 |
| 645 | $CH_3$ | Br | OH | S | 178–180 |
| 646 | $CH_3$ | Br | $OCH_2C(Br){=}CH_2$ | S | 126–128 |
| 647 | $CH_3$ | Br | $OCH_2CH{=}CH_2$ | S | |
| 648 | $CH_3$ | $COC_3H_7$ | $OCH_2$ 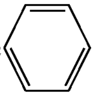 | NH | |
| 649 | $CH_3$ | $COC_3H_7$ | OH | NH | 193–196 |
| 650 | $CH_3$ | $CH_2CH{=}CH_2$ | OH | NH | 130–134 |
| 651 | $CH_3$ | $C_3H_7$ | OH | NH | 137–142 |
| 652 | $CH_3$ | $COOCH_2CH_2F$ | OH | NH | 193–195 |
| 653 | $CH_3$ | $COOCH_2CH_2Cl$ | OH | NH | 203–205 |
| 654 | $CH_3$ | $COOCH(CH_3)CH_2Cl$ | OH | O | 143–147 |
| 655 | $CH_3$ | $COOCH(CH_2Cl)_2$ | OH | O | 115–119 |
| 656 | $CH_3$ | $COOCH(CH_3)CH2F$ | OH | O | 150–153 |
| 657 | $CH_3$ | $COOCH(CH_3)CF_3$ | OH | O | 125–128 |
| 658 | $CH_3$ | $COOCH_2CHF_2$ | OH | O | 144–147 |
| 659 | $CH_3$ | $COOCH_2CH_2CH_2F$ | OH | O | 153–156 |
| 660 | $CH_3$ | $COOCH_2CH_2OH$ | OH | O | 148–151 |
| 661 | $CH_3$ | $COOCH_2COOC_2H_5$ | OH | O | 130–133 |
| 662 | $CH_3$ | COO 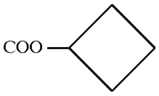 | OH | O | 154–157 |
| 663 | $CH_3$ | $CON(C_2H_5)_2$ | OH | NH | 151–155 |

TABLE 40

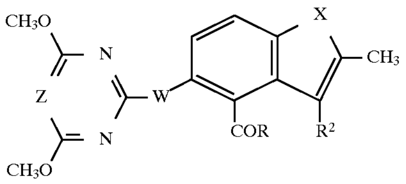

| Compound No. | $R^2$ | R | X | W | Z | m.p. (°C.) or ($n_D^{20}$) |
|---|---|---|---|---|---|---|
| 664 | H | $OCH_2$ 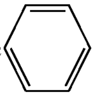 | NH | O | CH | 135–139 |
| 665 | H | OH | NH | O | CH | 167–170 |
| 666 | $CH_2CH{=}CH_2$ | $OCH_3$ | NH | O | CH | |
| 667 | $CH_2CH{=}CH_2$ | OH | NH | O | CH | 130–134 |
| 668 | $CH_2C{\equiv}CH$ | OCH3 | NH | O | CH | |
| 669 | $CH_2C{\equiv}CH$ | OH | NH | O | CH | |
| 670 | $CH_2CN$ | OCH3 | NH | O | CH | |
| 671 | $CH_2CN$ | OH | NH | O | CH | 165–169 |
| 672 | $CH_2COOCH_3$ | $OCH_2$ 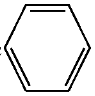 | NH | O | CH | |
| 673 | $CH_2COOCH_3$ | OH | NH | O | CH | |
| 674 | $CH_2N(CH_3)_2$ | $OCH_2CH{=}CH_2$ | NH | O | CH | |
| 675 | $CH_2N(CH_3)_2$ | OH | NH | O | CH | |
| 676 | $CH{=}CH{-}CN$ | $OCH_2CH{=}CH_2$ | NH | O | CH | |
| 677 | $CH{=}CH{-}CN$ | OH | NH | O | CH | |
| 678 | $CH{=}CH{-}NO_2$ | $OCH_2CH{=}CH_2$ | NH | O | CH | |
| 679 | $CH{=}CH{-}NO_2$ | OH | NH | O | CH | |
| 680 | CHO | $OCH_2$ 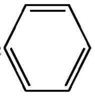 | NH | O | CH | 148–149 |
| 681 | CHO | OH | NH | O | CH | 201–206 |
| 682 | $CH{=}N{-}C_3H_7$-i | $OCH_2CH{=}CH_2$ | NH | O | CH | |
| 683 | $CH{=}N{-}C_3H_7$-i | OH | NH | O | CH | |
| 684 | CH=N— 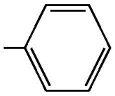 | $OCH_2CH{=}CH_2$ | NH | O | CH | |

TABLE 41

| Compound No. | $R^2$ | R | X | W | Z | m.p. (°C.) or ($n_D^{20}$) |
|---|---|---|---|---|---|---|
| 685 | CH=N— 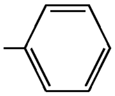 | OH | NH | O | CH | |
| 686 | CH=N—NH 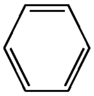 | $OCH_2$ 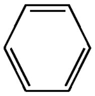 | NH | O | CH | |
| 687 | CH=N—NH 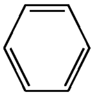 | OH | NH | O | CH | |

TABLE 41-continued

| Compound No. | $R^2$ | R | X | W | Z | m.p. (°C.) or ($n_D^{20}$) |
|---|---|---|---|---|---|---|
| 688 | $CH{=}N{-}N(CH_3)_2$ | 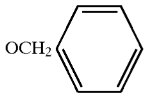 | NH | O | CH | |
| 689 | $CH{=}N{-}N(CH_3)_2$ | OH | NH | O | CH | |
| 690 | $CH{=}NOH$ | 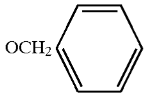 | NH | O | CH | |
| 691 | $CH{=}NOH$ | OH | NH | O | CH | 165–170 |
| 692 | $CH{=}NO{-}CH_3$ | 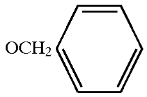 | NH | O | CH | 131–133 |
| 693 | $CH{=}NO{-}CH_3$ | OH | NH | O | CH | 171–175 |
| 694 | H | OH | NH | O | N | 152–154 |
| 695 | $CH{=}NO{-}CH_3$ | OH | NH | O | N | |
| 696 | $CH{=}NO{-}CH_3$ | $OCH_3$ | NH | S | CH | |
| 697 | $CH{=}NO{-}CH_3$ | OH | NH | S | CH | |
| 698 | $CH{=}NO{-}CH_3$ | $OCH_2C{\equiv}CH$ | NH | O | CH | |
| 699 | $CH{=}NO{-}CH_3$ | $OCH_2OCH_3$ | NH | O | CH | |
| 700 | $CH{=}NO{-}CH_3$ | $OCH(CH_3)OC({=}O)C_4H_9$-t | NH | O | CH | |
| 701 | $CH{=}NO{-}CH_3$ | 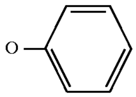 | NH | O | CH | |
| 702 | $CH{=}NO{-}CH_3$ | $O{-}N{=}C(CH_3)_2$ | NH | O | CH | |
| 703 | $CH{=}NO{-}CH_3$ | $SCH_3$ | NH | O | CH | |
| 704 | $CH{=}NO{-}CH_3$ | $SCH_2CH{=}CH_2$ | NH | O | CH | |
| 705 | $CH{=}NO{-}CH_3$ | $SCH_2C{\equiv}CH$ | NH | O | CH | |

TABLE 42

| Compound No. | $R^1$ | R | X | W | Z | m.p. (°C.) or ($n_D^{20}$) |
|---|---|---|---|---|---|---|
| 706 | $CH{=}NO{-}CH_3$ | 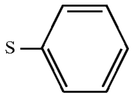 | NH | O | CH | |
| 707 | $CH{=}NO{-}CH_3$ | $NHC_2H_5$ | NH | O | CH | |
| 708 | $CH{=}NO{-}CH_3$ | 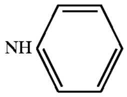 | NH | O | CH | |
| 709 | $CH{=}NO{-}CH_3$ | $NHSO_2CH_3$ | NH | O | CH | |
| 710 | $CH{=}NO{-}CH_3$ | 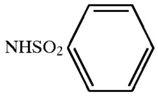 | NH | O | CH | |
| 711 | $CH{=}NO{-}CH_3$ | 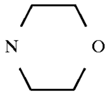 | NH | O | CH | |

TABLE 42-continued
| Compound No. | $R^1$ | R | X | W | Z | m.p. (°C.) or ($n_D^{20}$) |
|---|---|---|---|---|---|---|
| 712 | $CH=NO-CH_3$ | 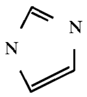 | NH | O | CH | |
| 713 | $CH=NO-C_3H_7$-i | 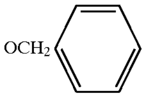 | NH | O | CH | |
| 714 | $CH=NO-C_3H_7$-i | OH | NH | O | CH | 123–127 |
| 715 | $CH=NO-CH_2CH=CH_2$ | OH | NH | O | CH | |
| 716 | $CH=NO-CH_2C\equiv CH$ | OH | NH | O | CH | |
| 717 | 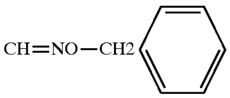 | $OCH_2CH=CH_2$ | NH | O | CH | |
| 718 | 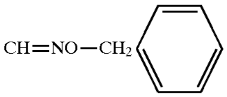 | OH | NH | O | CH | |
| 719 | 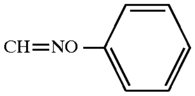 | $OCH_3$ | NH | O | CH | |
| 720 | 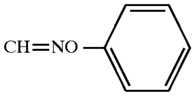 | OH | NH | O | CH | |
| 721 | $COOC_2H_5$ | 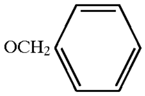 | NH | O | CH | 196–199 |
| 722 | $NH_2$ | $OCH_2CH=CH_2$ | NH | O | CH | 132–135 |
TABLE 43
| Compound No. | $R^2$ | R | X | W | Z | m.p. (°C.) or ($n_D^{20}$) |
|---|---|---|---|---|---|---|
| 723 | $NH_2$ | 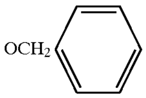 | NH | O | CH | |
| 724 | $NH_2$ | OH | NH | O | CH | |
| 725 | $NHCH_3$ | 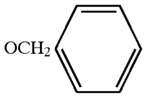 | NH | O | CH | |
| 726 | $NHCH_3$ | OH | NH | O | CH | |
| 727 | 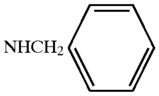 | $OCH_2CH=CH_2$ | NH | O | CH | |

TABLE 43-continued

| Compound No. | $R^2$ | R | X | W | Z | m.p. (°C.) or ($n_D^{20}$) |
|---|---|---|---|---|---|---|
| 728 | 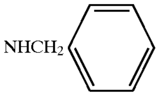 | OH | NH | O | CH | |
| 729 | 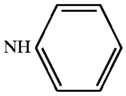 | $OCH_2CH{=}CH_2$ | NH | O | CH | |
| 730 | 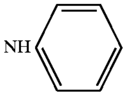 | OH | NH | O | CH | |
| 731 | $N(CH_3)_2$ | 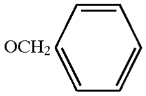 | NH | O | CH | |
| 732 | $N(CH_3)_2$ | OH | NH | O | CH | |
| 733 | 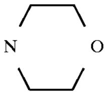 | 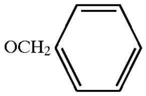 | NH | O | CH | |
| 734 | 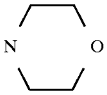 | OH | NH | O | CH | |
| 735 | $NHC(=O)CH_3$ | $OCH_2CH{=}CH_2$ | NH | O | CH | 177–180 |
| 736 | $NHC(=O)CH_3$ | OH | NH | O | CH | 230–233 |
| 737 | 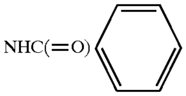 | $OCH_2CH{=}CH_2$ | NH | O | CH | |
| 738 | 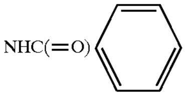 | OH | NH | O | CH | 168–172 |
| 739 | $NHCOOC_2H_5$ | $OCH_2CH{=}CH_2$ | NH | O | CH | |
| 740 | $NHCOOC_2H_5$ | OH | NH | O | CH | 177–179 |

TABLE 44

| Compound No. | $R^2$ | R | X | W | Z | m.p. (°C.) or ($n_D^{20}$) |
|---|---|---|---|---|---|---|
| 741 | $NHC(=O)SC_2H_5$ | $OCH_2CH{=}CH_2$ | NH | O | CH | |
| 742 | $NHC(=O)SC_2H_5$ | OH | NH | O | CH | |
| 743 | 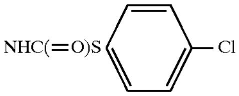 | $OCH_2CH{=}CH_2$ | NH | O | CH | |
| 744 | 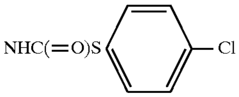 | OH | NH | O | CH | |
| 745 | $NHC(=O)NHCH_3$ | $OCH_2CH{=}CH_2$ | NH | O | CH | |
| 746 | $NHC(=O)NHCH_3$ | OH | NH | O | CH | |

TABLE 44-continued

| Compound No. | $R^2$ | R | X | W | Z | m.p. (°C.) or ($n_D^{20}$) |
|---|---|---|---|---|---|---|
| 747 | $NHC(=O)N(CH_3)_2$ | $OCH_2$ 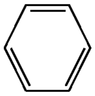 | NH | O | CH | |
| 748 | $NHC(=O)N(CH_3)_2$ | OH | NH | O | CH | |
| 749 | $NHSO_2CH_3$ | $OCH_2CH=CH_2$ | NH | O | CH | |
| 750 | $NHSO_2CH_3$ | OH | NH | O | CH | |
| 751 | $NHSO_2$ 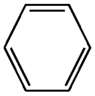 | $OCH_2CH=CH_2$ | NH | O | CH | |
| 752 | $NHSO_2$ 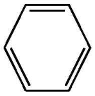 | OH | NH | O | CH | |
| 753 | $N=CHCH_3$ | $OCH_2CH=CH_2$ | NH | O | CH | |
| 754 | $N=CHCH_3$ | OH | NH | O | CH | |
| 755 | N=CH 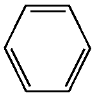 | $OCH_2CH=CH_2$ | NH | O | CH | |
| 756 | N=CH 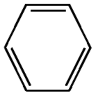 | OH | NH | O | CH | 265–270 |
| 757 | N= 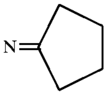 | $OCH_2CH=CH_2$ | NH | O | CH | |
| 758 | N= 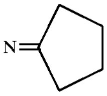 | OH | NH | O | CH | |
| 759 | $NO_2$ | $OCH_2CH=CH_2$ | NH | O | CH | 155–159 |
| 760 | $NO_2$ | OH | NH | O | CH | >300° C. |

TABLE 45

| Compound No. | $R^2$ | R | X | W | Z | m.p. (°C.) or ($n_D^{20}$) |
|---|---|---|---|---|---|---|
| 761 | $NO_2$ | $OCH_2CH=CH_2$ | $NCH_3$ | O | CH | |
| 762 | $NO_2$ | OH | $NCH_3$ | O | CH | |
| 763 | $COOC_2H_5$ | $OCH_2$ 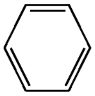 | $NCH_2CH=CH_2$ | O | CH | 1.5774 |
| 764 | $COOC_2H_5$ | OH | $NCH_2CH=CH_2$ | O | CH | |
| 765 | $NH_2$ | $OCH_2$ 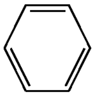 | $NCH_2CH=CH_2$ | O | CH | |
| 766 | $NH_2$ | OH | $NCH_2CH=CH_2$ | O | CH | 215–220 |
| 767 | H | $OCH_2OCH_3$ | $NCH_2C\equiv CH$ | O | CH | |

TABLE 45-continued

| Compound No. | $R^2$ | R | X | W | Z | m.p. (°C.) or ($n_D^{20}$) |
|---|---|---|---|---|---|---|
| 768 | H | OH | $NCH_2C{\equiv}CH$ | O | CH | |
| 769 | $COOC_2H_5$ | $OCH_3$ | $NCH_2OCH_3$ | O | CH | |
| 770 | $COOC_2H_5$ | OH | $NCH_2OCH_3$ | O | CH | 158–162 |
| 771 | $COOC_2H_5$ | $OCH_2$ 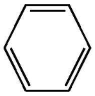 | $NCH_2OC(=O)C_4H_9$-t | O | CH | 182–183.5 |
| 772 | $COOC_2H_5$ | OH | $NCH_2OC(=O)C_4H_9$-t | O | CH | 193–195 |
| 773 | $COOC_2H_5$ | $OCH_2$ 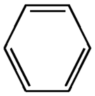 | $NCH_2COOC_2H_5$ | O | CH | 141–143.5 |
| 774 | $COOC_2H_5$ | OH | $NCH_2COOC_2H_5$ | O | CH | 190–193 |
| 775 | H | OH | $NC(=O)CH_3$ | O | CH | |
| 776 | H | OH | $NC(=O)CH_3$ | $CH_2$ | CH | |
| 777 | H | OH | $NC(=O)CH_3$ | CH(CN) | CH | |
| 778 | H | OH | $NC(=O)CH_3$ | C(=O) | CH | |
| 779 | H | $OCH_3$ | $NC(=O)CH_3$ | N(CHO) | CH | |
| 780 | Cl | $OCH_2OCH_3$ | $NC(=O)CH_3$ | O | CH | |
| 781 | Cl | OH | $NC(=O)CH_3$ | O | CH | |
| 782 | $OCH_3$ | $OCH_2$ 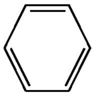 | $NC(=O)CH_3$ | O | CH | |

TABLE 46

| Compound No. | $R^2$ | R | X | W | Z | m.p. (°C.) or ($n_D^{20}$) |
|---|---|---|---|---|---|---|
| 783 | $OCH_3$ | OH | $NC(=O)CH_3$ | O | CH | |
| 784 | 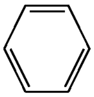 | $OCH_2CH=CH_2$ | $NC(=O)CH_3$ | O | CH | |
| 785 | 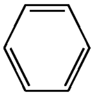 | OH | $NC(=O)CH_3$ | O | CH | |
| 786 | $COOCH_3$ | $OCH_2$ 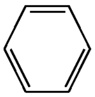 | $NC(=O)CH_3$ | O | CH | 133–135 |
| 787 | $COOCH_3$ | OH | $NC(=O)CH_3$ | O | CH | 186–189 |
| 788 | $COOC_2H_5$ | $OCH_2$ 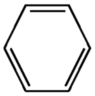 | $NC(=O)CH_3$ | O | CH | 128–130.5 |
| 789 | $COOC_2H_5$ | OH | $NC(=O)CH_3$ | O | CH | 174–177 |
| 790 | $COOCH_2CH=CH_2$ | $OC_2H_4Si(CH_3)_3$ | $NC(=O)CH_3$ | O | CH | |
| 791 | $COOCH_2CH=CH_2$ | OH | $NC(=O)CH_3$ | O | CH | |
| 792 | $COOCH_2C{\equiv}CH$ | $OCH_2OCH_3$ | $NC(=O)CH_3$ | O | CH | |
| 793 | $COOCH_2C{\equiv}CH$ | OH | $NC(=O)CH_3$ | O | CH | |
| 794 | $C(=O)SCH_3$ | $OCH_3$ | $NC(=O)CH_3$ | O | CH | |
| 795 | $C(=O)SCH_3$ | OH | $NC(=O)CH_3$ | O | CH | |

TABLE 46-continued

| Compound No. | $R^2$ | R | X | W | Z | m.p. (°C.) or ($n_D^{20}$) |
|---|---|---|---|---|---|---|
| 796 | $COOC_2H_5$ | $OCH_2$ 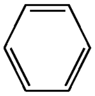 | $COOCH_2$ 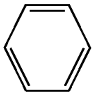 | O | CH | 128–132.5 |
| 797 | $COOC_2H_5$ | OH | $COOCH_2$ 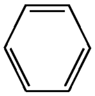 | O | CH | 113–115 |
| 798 | $COOCH_2$ 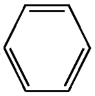 | $OCH_2OCH_3$ | $COOCH_2$ 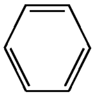 | O | CH | |
| 799 | $COOCH_2$ 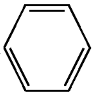 | OH | $COOCH_2$ 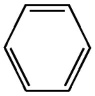 | O | CH | |

TABLE 47

| Compound No. | $R^2$ | R | X | W | Z | m.p. (°C.) or ($n_D^{20}$) |
|---|---|---|---|---|---|---|
| 800 | COO 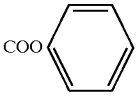 | $OCH_2$ 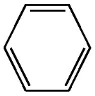 | C(=O) 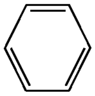 | O | CH | |
| 801 | COO 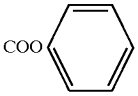 | OH | C(=O) 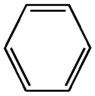 | O | CH | |
| 802 | $C(=O)SCH_2CH=CH_2$ | $OCH_2CH=CH_2$ | C(=O) 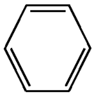 | O | CH | |
| 803 | $C(=O)SCH_2CH=CH_2$ | OH | C(=O) 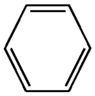 | O | CH | |
| 804 | $C(=O)SCH_2C\equiv CH$ | $OCH_2CH=CH_2$ | C(=O) 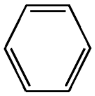 | O | CH | |
| 805 | $C(=O)SCH_2C\equiv CH$ | OH | C(=O) 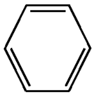 | O | CH | |
| 806 | $C(=O)CH_3$ | $OCH_2$ 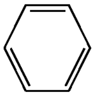 | $C(=O)SCH_2$ 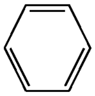 | O | CH | |
| 807 | $C(=O)CH_3$ | OH | $C(=O)SCH_2$ 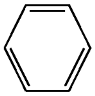 | O | CH | |

TABLE 47-continued
| Compound No. | $R^2$ | R | X | W | Z | m.p. (°C.) or ($n_D^{20}$) |
|---|---|---|---|---|---|---|
| 808 | 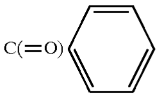 | OH | 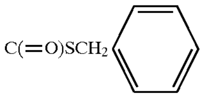 | O | CH | |
| 809 | 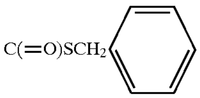 | OH | 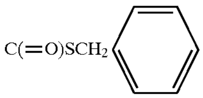 | O | CH | |
| 810 | 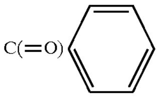 | OH | 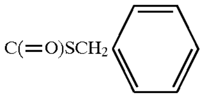 | O | CH | |
| 811 | H | OH | 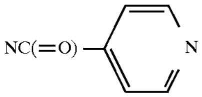 | O | CH | |
| 812 | $COOC_2H_5$ | 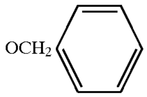 | $NCOOC_2H_5$ | O | CH | 105–108 |
| 813 | $COOC_2H_5$ | OH | $NCOOC_2H_5$ | O | CH | 170–173 |
| 814 | $COOC_2H_5$ | 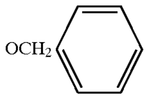 | $NCOOC_4H_9$-t | O | CH | 1.5649 |
| 815 | $COOC_2H_5$ | OH | $NCOOC_4H_9$-t | O | CH | 138–142 |
TABLE 48
| Compound No. | $R^2$ | R | X | W | Z | m.p. (°C.) or ($n_D^{20}$) |
|---|---|---|---|---|---|---|
| 816 | H | $OCH_2CH=CH_2$ | 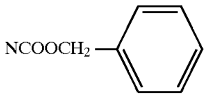 | O | CH | |
| 817 | H | OH | 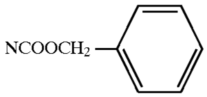 | O | CH | |
| 818 | H | 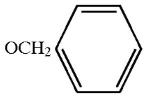 | 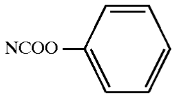 | O | CH | |
| 819 | H | OH | 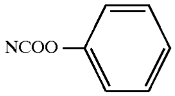 | O | CH | |
| 820 | H | $OCH_2CH=CH_2$ | $NC(=O)SCH_3$ | O | CH | |
| 821 | H | OH | $NC(=O)SCH_3$ | O | CH | |
| 822 | H | $OCH_2CH=CH_2$ | 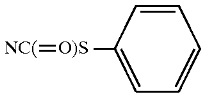 | O | CH | |

TABLE 48-continued
| Compound No. | $R^2$ | R | X | W | Z | m.p. (°C.) or ($n_D^{20}$) |
|---|---|---|---|---|---|---|
| 823 | H | OH | 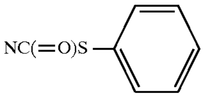 | O | CH | |
| 824 | $COOC_2H_5$ | 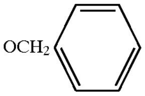 | $NC(=O)N(CH_3)_2$ | O | CH | 1.5767 |
| 825 | $COOC_2H_5$ | OH | $NC(=O)N(CH_3)_2$ | O | CH | 172–174 |
| 826 | $COOC_2H_5$ | 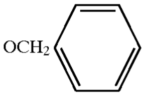 | $NSO_2CH_3$ | O | CH | 140.5–145 |
| 827 | $COOC_2H_5$ | OH | $NSO_2CH_3$ | O | CH | 186–188 |
| 828 | $COOC_2H_5$ | 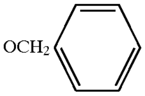 | 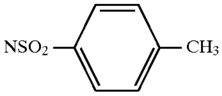 | O | CH | Unmeasurable |
| 829 | $COOC_2H_5$ | OH | 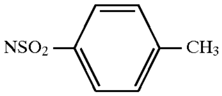 | O | CH | 149–152 |
| 830 | $COOC_2H_5$ | 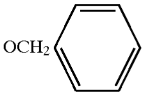 | $NSi(CH_3)_2C_4H_9$-t | O | CH | Unmeasurable |
| 831 | $COOC_2H_5$ | OH | $NSi(CH_3)_2C_4H_9$-t | O | CH | 175–178 |
| 832 | $COOC_2H_5$ | 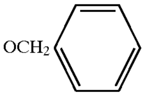 | $N-SCCl_3$ | O | CH | 173–177 |
TABLE 49
| Compound No. | $R^2$ | R | X | W | Z | m.p. (°C.) or ($n_D^{20}$) |
|---|---|---|---|---|---|---|
| 833 | $COOC_2H_5$ | OH | $N-SCCl_3$ | O | CH | |
| 834 | H | $OCH_3$ | 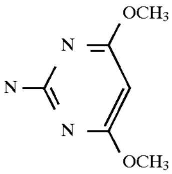 | O | CH | 187–190 |
| 835 | H | OH | 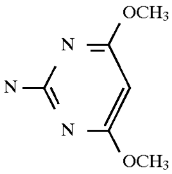 | O | CH | 182–183.5 |

TABLE 49-continued

| Compound No. | $R^2$ | R | X | W | Z | m.p. (°C.) or ($n_D^{20}$) |
|---|---|---|---|---|---|---|
| 836 | CN | 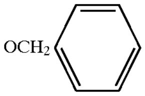 | 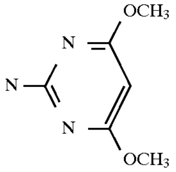 | O | CH | 176–177 |
| 837 | H | 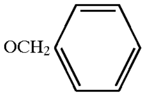 | NC(=O)$CH_3$ | O | CH | |
| 838 | H | OH | NC(=O)$CH_3$ | O | CH | |
| 839 | H | $OCH_2CH=CH_2$ | NC(=O)$CH_3$ | O | CH | |
| 840 | H | OH | NC(=O)$CH_3$ | O | CH | |
| 841 | H | OH | NC(=O)$CH_3$ | O | CH | |

TABLE 50

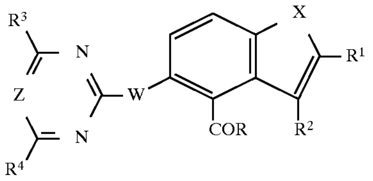

| Compound No. | $R^1$ | $R^2$ | $R^3$ | $R^4$ | R | X | W | Z | m.p. (°C.) or ($n_D^{20}$) |
|---|---|---|---|---|---|---|---|---|---|
| 842 | $CH_3$ | H | $CH_3$ | $CH_3$ | OH | NH | O | CH | 184–186 |
| 843 | $CH_3$ | $CH=NOCH_3$ | $CH_3$ | $CH_3$ | OH | NH | O | CH | |
| 844 | $CH_3$ | H | $N(CH_3)_2$ | $OCH_3$ | OH | NH | O | CH | 164–167 |
| 845 | $CH_3$ | H | $NHCH_3$ | $OCH_3$ | OH | NC(=O)$CH_3$ | O | CH | |
| 846 | $CF_3$ | H | $OCH_3$ | $OCH_3$ | OH | NC(=O)$CH_3$ | O | CH | |

TABLE 51

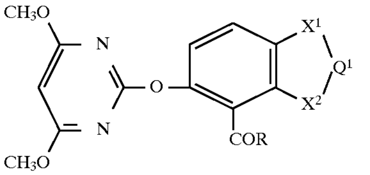

| Compound No. | $X^1$ | $Q^1$ | $X^2$ | R | m.p. (°C.) or ($n_D^{20}$) |
|---|---|---|---|---|---|
| 847 | $CH_2$ | $CH_2$ | C=O | $OCH_3$ | 150–153 |
| 848 | $CH_2$ | $CH_2$ | C=O | OH | 181.5–184 |
| 849 | $CH_2$ | $CH_2$ | $C=NOCH_3$ | $OCH_3$ | 152–154 |
| 850 | $CH_2$ | $CH_2$ | $C=NOCH_3$ | OH | |
| 851 | $CH_2$ | $CH_2$ | CHOH | $OCH_3$ | 135–137 |
| 852 | $CH_2$ | $CH_2$ | CHOH | OH | 151–153.5 |
| 853 | NH | C=O | O | $OC_2H_4Si(CH_3)_3$ | Unmeasurable |
| 854 | NH | C=O | O | OH | 188–189 |
| 855 | NH | C=O | NH | $OCH_3$ | |
| 856 | NH | C=O | NH | OH | |
| 857 | NH | $C=C(CN)COOCH_3$ | O | $OC_2H_4Si(CH_3)_3$ | 100–105 |
| 858 | NH | $C=C(CN)COOCH_3$ | O | OH | 250–260 |
| 859 | NH | $C=C(CN)_2$ | O | $OC_2H_4Si(CH_3)_3$ | 185–187 |
| 860 | NH | $C=C(CN)_2$ | O | $O^-N^+(C_4H_9)_4$ | 125–130 |

TABLE 51-continued

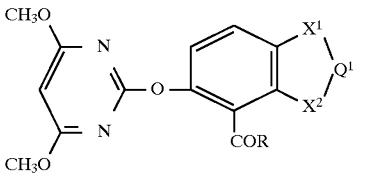

| Compound No. | $X^1$ | $Q^1$ | $X^2$ | R | m.p. (°C.) or ($n_D^{20}$) |
|---|---|---|---|---|---|
| 861 | NH | C=C(CN)C(O) 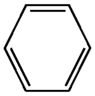 | O | $OC_2H_4Si(CH_3)_3$ | |
| 862 | NH | C=C(CN)C(O) 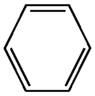 | O | OH | |
| 863 | NH | C=C(CN)C(O) 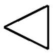 | O | $OC_2H_4Si(CH_3)_3$ | |
| 864 | NH | C=C(CN)C(O) 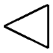 | O | OH | |
| 865 | O | C=O | S | $OCH_3$ | 138–139 |
| 866 | O | C=O | S | OH | |

TABLE 52

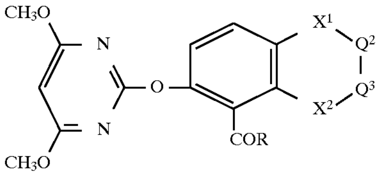

| Compound No. | $X^1$ | $Q^2$ | $Q^3$ | $X^2$ | R | m.p. (°C.) or ($n_D^{20}$) |
|---|---|---|---|---|---|---|
| 867 | $CH_2$ | $CH_2$ | $CH_2$ | C=O | $OCH_3$ | 185–187 |
| 868 | $CH_2$ | $CH_2$ | $CH_2$ | C=O | OH | 183–189 |
| 869 | $CH_2$ | $CH_2$ | $CH_2$ | $C=NOCH_3$ | $OCH_3$ | 128–131 |
| 870 | $CH_2$ | $CH_2$ | $CH_2$ | $C=NOCH_3$ | OH | |
| 871 | $CH_2$ | $CH_2$ | $CH_2$ | CHOH | $OCH_3$ | |
| 872 | $CH_2$ | $CH_2$ | $CH_2$ | CHOH | OH | 147.5–149 |
| 873 | $CH_2$ | $CH_2$ | $CH_2$ | $CH_2$ | $OCH_2$— 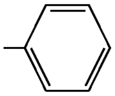 | 1.5332 |
| 874 | $CH_2$ | $CH_2$ | $CH_2$ | $CH_2$ | $OCH_3$ | 127–128 |
| 875 | $CH_2$ | $CH_2$ | $CH_2$ | $CH_2$ | OH | 141–147 |
| 876 | $CH_2$ | $CH_2$ | $C(CH_3)_2$ | O | $OCH_3$ | |
| 877 | $CH_2$ | $CH_2$ | $C(CH_3)_2$ | O | OH | 151–153 |
| 878 | NH | C=O | $CH_2$ | O | $OC_2H_4Si(CH_3)_3$ | 148–150 |
| 879 | NH | C=O | $CH_2$ | O | OH | 200–202 |
| 880 | $NCH_3$ | C=O | $CH_2$ | O | $OC_2H_4Si(CH_3)_3$ | Unmeasurable |
| 881 | $NCH_3$ | C=O | $CH_2$ | O | OH | 178–180 |
| 882 | NH | C=O | $CH(C_2H_5)$ | O | $OC_2H_4Si(CH_3)_3$ | Unmeasurable |
| 883 | NH | C=O | $CH(C_2H_5)$ | O | OH | 195–197 |
| 884 | NH | $CH_2$ | $CH_2$ | O | $OC_2H_4Si(CH_3)_3$ | 1.5333 |
| 885 | NH | $CH_2$ | $CH_2$ | O | OH | 160–164 |
| 886 | NH | $CH_2$ | $CH_2$ | S | $OC_2H_4Si(CH_3)_3$ | Unmeasurable |
| 887 | NH | $CH_2$ | $CH_2$ | S | OH | 164–166 |
| 888 | NH | $CH_2$ | $CH_2$ | NH | $OCH_3$ | |
| 889 | NH | $CH_2$ | $CH_2$ | NH | OH | |

TABLE 52-continued

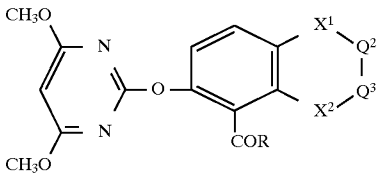

| Compound No. | $X^1$ | $Q^2$ | $Q^3$ | $X^2$ | R | m.p. (°C.) or ($n_D^{20}$) |
|---|---|---|---|---|---|---|
| 890 | NH | $CH(CH_3)$ | $CH_2$ | O | $OC_2H_4Si(CH_3)_3$ | Unmeasurable |
| 891 | NH | $CH(CH_3)$ | $CH_2$ | O | OH | 174–175 |
| 892 | NH | $CH_2$ | $CH(CH_3)$ | O | OH | 110–115 |
| 893 | NH | $CH_2$ | $CH(C_2H_5)$ | O | OH | |

TABLE 53

| Compound No. | $X^1$ | $Q^2$ | $Q^3$ | $X^2$ | R | m.p. (°C.) or ($n_D^{20}$) |
|---|---|---|---|---|---|---|
| 894 | NH | $CH_2$ | $C(CH_3)_2$ | O | $OC_2H_4Si(CH_3)_3$ | |
| 895 | NH | $CH_2$ | $C(CH_3)_2$ | O | OH | |
| 896 | NH | $CH_2$ | $C{=}CH_2$ | O | $OC_2H_4Si(CH_3)_3$ | Unmeasurable |
| 897 | NH | $CH_2$ | $C{=}CH_2$ | O | OH | 90–95 |
| 898 | NH | $CH_2$ | $C{=}CHCH_3$ | O | $OC_2H_4Si(CH_3)_3$ | |
| 899 | NH | $CH_2$ | $C{=}CHCH_3$ | O | OH | |
| 900 | NH | $CH_2$ | $CH(CH_2COOCH_3)$ | O | $OC_2H_4Si(CH_3)_3$ | Unmeasurable |
| 901 | NH | $CH_2$ | $CH(CH_2COOCH_3)$ | O | OH | |

TABLE 54

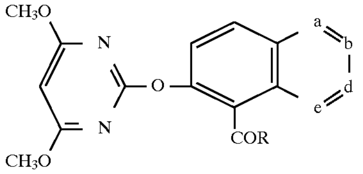

| Compound No. | a | b | d | e | R | m.p. (°C.) or ($n_D^{20}$) |
|---|---|---|---|---|---|---|
| 902 | N | CH | CH | CH | H | 159–161 |
| 903 | N | CH | CH | CH | OH | 195–198 |
| 904 | N | CH | CH | CH | $OCH_3$ | 160–162 |
| 905 | CH | N | CH | CH | H | |
| 906 | CH | N | CH | CH | OH | |
| 907 | CH | N | CH | CH | $OCH_3$ | |
| 908 | CH | CH | N | CH | H | |
| 909 | CH | CH | N | CH | OH | |
| 910 | CH | CH | N | CH | $OCH_3$ | |
| 911 | N | N | CH | CH | H | |
| 912 | N | N | CH | CH | OH | |
| 913 | N | N | CH | CH | $OCH_3$ | |
| 914 | N | CH | N | CH | H | |
| 915 | N | CH | N | CH | OH | 174–177 |
| 916 | N | CH | N | CH | $OCH_3$ | |
| 917 | N | CH | CH | N | H | |
| 918 | N | CH | CH | N | OH | 148–151 |
| 919 | N | CH | CH | N | $OCH_3$ | 164–166 |

TABLE 54-continued

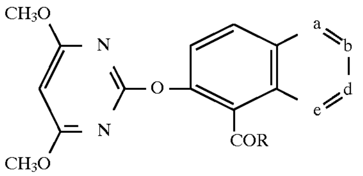

| Compound No. | a | b | d | e | R | m.p. (°C.) or ($n_D^{20}$) |
|---|---|---|---|---|---|---|
| 920 | CH | N | N | CH | H | |
| 921 | CH | N | N | CH | OH | |
| 922 | CH | N | N | CH | $OCH_3$ | |
| 923 | CH | N | CH | N | H | |
| 924 | CH | N | CH | N | OH | |
| 925 | CH | N | CH | N | $OCH_3$ | |
| 926 | CH | CH | N | N | H | |
| 927 | CH | CH | N | N | OH | |
| 928 | CH | CH | N | N | $OCH_3$ | |

TABLE 55

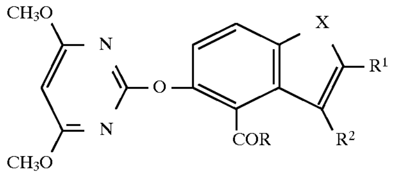

| Compound No. | $R^1$ | $R^2$ | R | X | m.p. (°C.) or ($n_D^{20}$) |
|---|---|---|---|---|---|
| 929 | $CH_3$ | $COOCH(CH_2F)_2$ | OH | O | 149–152 |
| 930 | $CH_3$ | COOH | $OCH_2OC_2H_4OCH_3$ | O | 139–141 |
| 931 | $CH_3$ | $COOC_2H_4OC_2H_5$ | OH | O | 143.5–146 |
| 932 | $CH_3$ | $COOC_2H_4OC_2H_5$ | $OCH_2CH{=}CH_2$ | O | 92–94 |
| 933 | $CH_3$ | $COOCH_2CH(OCH_3)_2$ | OH | O | 153–155 |
| 934 | $CH_3$ | $COOCH_2CH(OCH_3)_2$ | $OCH_2CH{=}CH_2$ | O | 75–77 |
| 935 | $CH_3$ | $COOCH_2C(CH_3){=}CH_2$ | OH | O | 143–146 |
| 936 | $CH_3$ | $COOCH_2C(CH_3){=}CH_2$ | $OCH_2OCH_3$ | O | 98–100 |
| 937 | $CH_3$ | $COOC_2H_4N(CH_3)_2$ | OH | O | 194–197 |
| 938 | $CH_3$ | $COOCH_2CH{=}C(CH_3)_2$ | $OCH_2OCH_3$ | O | 96–98 |
| 939 | $CH_3$ | $COOCH(CH_3)CH{=}CHCH_3$ | $OCH_2OCH_3$ | O | 72–75 |
| 940 | $CH_3$ | $COOCH(CH_3)CH_2Cl$ | $OCH_2CH{=}CH_2$ | O | 114–116 |
| 941 | $CH_3$ | $COOCH(CH_2Cl)_2$ | $OCH_2CH{=}CH_2$ | O | 138–140 |
| 942 | $CH_3$ | $COOCH(CH_3)CH_2F$ | $OCH_2CH{=}CH_2$ | O | 104–107 |
| 943 | $CH_3$ | $COOCH(CH_3)CF_3$ | $OCH_2CH{=}CH_2$ | O | 118–119.5 |
| 944 | $CH_3$ | $COOCH_2CHF_2$ | $OCH_2CH{=}CH_2$ | O | 103–106 |
| 945 | $CH_3$ | $COOCH_2CH_2CH_2F$ | $OCH_2CH{=}CH_2$ | O | 58–61 |
| 946 | $CH_3$ | $COOCH_2CH_2OH$ | $OCH_2CH{=}CH_2$ | O | 121–124 |
| 947 | $CH_3$ | $COOCH_2CO_2C_2H_5$ | $OCH_2CH{=}CH_2$ | O | 93–95 |
| 948 | $CH_3$ | 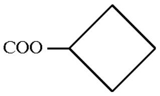 | $OCH_2CH{=}CH_2$ | O | 109–110 |
| 949 | H | H | OH | N-Pym | 190–193 |
| 950 | H | H | OH | NH | 169–170 |
| 951 | $CH_3$ | CN | 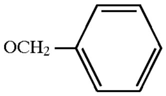 | NH | 169–172 |

(In this Table, Pym indicates 4,6-dimethoxypirimidin-2-yl.)

TABLE 56

| Compound No. | $R^1$ | $R^2$ | R | X | m.p. (°C.) or ($n_D^{20}$) |
|---|---|---|---|---|---|
| 952 | $CH_3$ | CN | OH | NH | 185–189 |
| 953 | $CH_3$ | $CH_2CN$ | 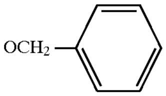 | NH | 151–156 |
| 954 | $CH_3$ | $COCOOC_2H_5$ | 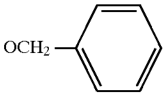 | NH | 150–153 |
| 955 | $CH_3$ | $COCOOC_2H_5$ | OH | NH | 179–183 |
| 956 | $CH_3$ | 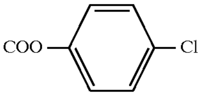 | 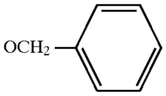 | NH | 82–85 |

TABLE 56-continued
| Compound No. | $R^1$ | $R^2$ | R | X | m.p. (°C.) or ($n_D^{20}$) |
|---|---|---|---|---|---|
| 957 | $CH_3$ | 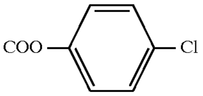 | OH | NH | 143–146 |
| 958 | $CH_3$ | 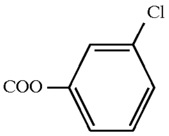 | 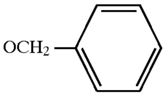 | NH | 89–92 |
| 959 | $CH_3$ | 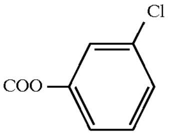 | OH | NH | 127–129 |
| 960 | $CH_3$ | 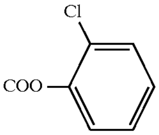 | 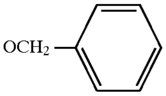 | NH | 94–99 |
| 961 | $CH_3$ | 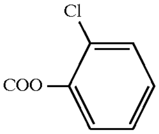 | OH | NH | 137–140 |
| 962 | $CH_3$ | 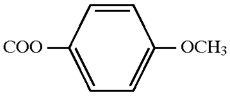 | 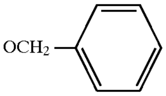 | NH | 103–105 |
| 963 | $CH_3$ | 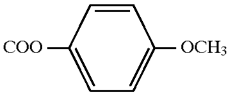 | OH | NH | 170–173 |
| 964 | $CH_3$ | 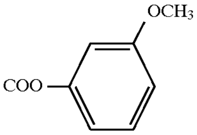 | 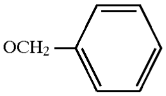 | NH | 106–109 |
| 965 | $CH_3$ | 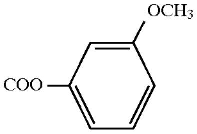 | OH | NH | 123–125 |
| 966 | $CH_3$ | 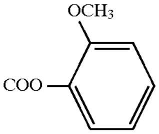 | 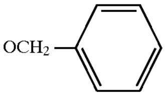 | NH | 89–91 |
| 967 | $CH_3$ | 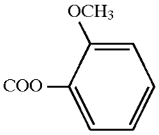 | OH | NH | 140–143 |

TABLE 57

| Compound No. | $R^1$ | $R^2$ | R | X | m.p. (°C.) or ($n_D^{20}$) |
|---|---|---|---|---|---|
| 968 | $CH_3$ | $COOCH_2CH{=}CH_2$ | OH | NH | |
| 969 | $CH_3$ | $COOCH2C{\equiv}CH$ | OH | NH | |
| 970 | $CH_3$ | $CONHCH_3$ | 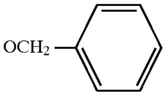 | NH | |
| 971 | $CH_3$ | $CONHCH_3$ | OH | NH | |
| 972 | $CH_3$ | 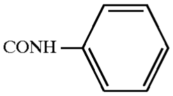 | 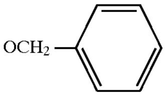 | NH | |
| 973 | $CH_3$ | 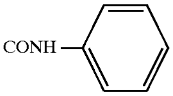 | OH | NH | |
| 974 | $CH_3$ | 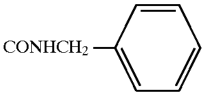 | 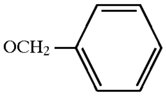 | NH | |
| 975 | $CH_3$ | 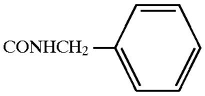 | OH | NH | |
| 976 | $CH_3$ | $COSCH_3$ | OH | NH | |
| 977 | $CH_3$ | $COSC_2H_5$ | OH | NH | |
| 978 | $CH_3$ | $COSC_3H_7$ | OH | NH | |
| 979 | $CH_3$ | $COSC_4H_9$ | OH | NH | |
| 980 | $CH_3$ | 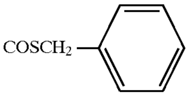 | OH | NH | |
| 981 | $CH_3$ | 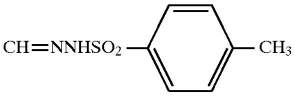 | OH | NH | 172–176 |
| 982 | $CH_3$ | $CH_3$ | 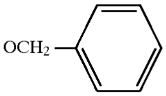 | NH | 115–118 |
| 983 | $CH_3$ | $CH_3$ | OH | NH | 168–172 |
| 984 | $CH_3$ | H | $OCH(CH_3)OCOC_4H_9$-t | NH | 52–55 |
| 985 | $CH_3$ | COOH | OH | NH | 178–182 |
| 986 | $CH_3$ | $COOCH_2OCH_3$ | $OCH_2OCH_3$ | NH | 145–148 |
| 987 | $CH_3$ | 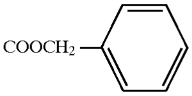 | OH | NH | 203–206 |

TABLE 58

| Compound No. | $R^1$ | $R^2$ | R | X | m.p. (°C.) or ($n_D^{20}$) |
|---|---|---|---|---|---|
| 988 | $CH_3$ | $COOC_3H_7$ | $OCH_2CH{=}CH_2$ | S | |
| 989 | $CH_3$ | $COOC_3H_7$ | OH | S | |
| 990 | $CH_3$ | $COOC_3H_7$-i | OH | S | |
| 991 | $CH_3$ | $COOC_4H_9$ | OH | S | |
| 992 | $CH_3$ | $CONHC_3H_7$ | OH | S | |
| 993 | $CH_3$ | $COSC_2H_5$ | OH | S | |
| 994 | H | $COOC_2H_5$ | OH | NH | |
| 995 | Cl | $COOC_2H_5$ | OH | NH | |
| 996 | CN | $COOC_2H_5$ | OH | NH | |
| 997 | $NO_2$ | $COOC_2H_5$ | OH | NH | |
| 998 | $CH_2Cl$ | $COOC_2H_5$ | OH | NH | |
| 999 | $CH_2OH$ | $COOC_2H_5$ | OH | NH | |
| 1000 | $CH_2OCH_3$ | $COOC_2H_5$ | OH | NH | |
| 1001 | H | $COCH_3$ | OH | NH | |
| 1002 | H | CHO | OH | NH | |
| 1003 | H | CN | OH | NH | |
| 1004 | H | $CH_3$ | OH | NH | |
| 1005 | $C_2H_5$ | $COOC_2H_5$ | OH | NH | |
| 1006 | $C_2H_5$ | H | OH | NH | |

TABLE 59

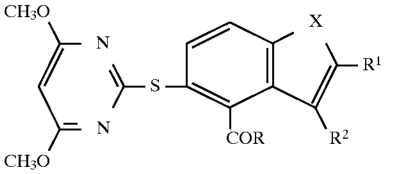

| Compound No. | $R^1$ | $R^2$ | R | X | m.p. (°C.) or ($n_D^{20}$) |
|---|---|---|---|---|---|
| 1007 | $CH_3$ | $COOC_3H_7$-i | $OCH_3$ | O | 120–121.5 |
| 1008 | $CH_3$ | $COOC_3H_7$-i | $OCH_2CH{=}CH_2$ | O | 1.5651 |
| 1009 | $CH_3$ | $COOC_3H_7$-i | OH | O | 188–191 |
| 1010 | $CH_3$ | $COOCH_3$ | $OCH_2CH{=}CH_2$ | O | 118–122 |
| 1011 | $CH_3$ | $COOCH_2$— 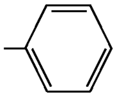 | $OCH_2CH{=}CH_2$ | NH | |
| 1012 | $CH_3$ | $COOCH_2$— 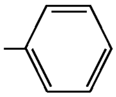 | OH | NH | |
| 1013 | $CH_3$ | H | OH | NH | |

Compounds (I) of the present invention can be produced, for example, in accordance with the following processes 1 to 6.

Process 1

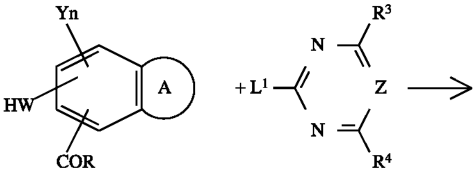

(II) (III)

-continued

Process 1

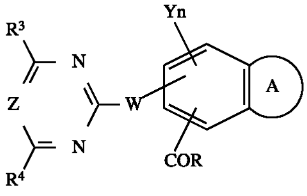

(I)

(wherein $L^1$ is a halogen atom, an alkylsulfonyl group, a benzylsulfonyl group or a substituted benzylsulfonyl group, and R, $R^3$, $R^4$, A, W, Y, Z and n are as defined above.)

A compound of the formula (I) can be produced by reacting a compound of the formula (II) with a compound of the formula (III) in a suitable solvent in the presence of an at least equal amount of a base at a temperature within a range of from room temperature to the boiling point of the solvent for from 0.5 to 24 hours.

As the base, an alkali metal such as metal sodium or metal potassium, an alkali metal hydride or an alkaline earth metal hydride such as sodium hydride, potassium hydride or calcium hydride, an alkali metal alkoxide such as potassium t-butoxide, an alkali metal carbonate such as sodium carbonate or potassium carbonate, an alkali metal hydrogen carbonate such as sodium hydrogen carbonate or potassium hydrogen carbonate, or an alkali metal hydroxide such as sodium hydroxide or potassium hydroxide, may be used.

As the solvent, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as methyl acetate or ethyl acetate, a ketone solvent such as acetone or methyl ethyl ketone, an aprotic polar solvent such as N,N-dimethylformamide, N,N-dimethylacetamide or dimethylsulfoxide, or acetonitrile, may, for example, be used.

The condensed heterocyclic carbonyl derivative (II) as the starting material can be obtained by known methods, for example, the methods disclosed in Bulletin de la Saciete Chimique de France), p. 2763–2766 (1975), J. Indian. Chem. Soc. Vol 45 (5), p. 439–445 (1968), Indian. J. Chem. Section B, 25B (8), p. 870–871 (1986), J. Chem. Soc. Organic Chemistry (1), p. 1–4 (1969), Indian. J. Chem. Section B, 15B (91), p. 1056–1058 (1977), Pract. Heterocyclic. Chem. Academic, p. 55 (1968), Organic Reaction, Vol 20, p. 337 (1973), Helvetica Chemica Acta., Vol 54, p. 959 (1970), J. Org. Chem., Vol 33 (12), p. 4426 (1968), Chemical and Pharmaceutical Bulletin, Vol 25 (11), p. 2988 (1977), and Parmaco, Edizione Scientifica (ITA), Vol 36 (9), p. 794 (1981).

Further, in a case where R in the formula (II) is H, a product wherein R is OH can be obtained by oxidation in accordance with a known method.

Process 2

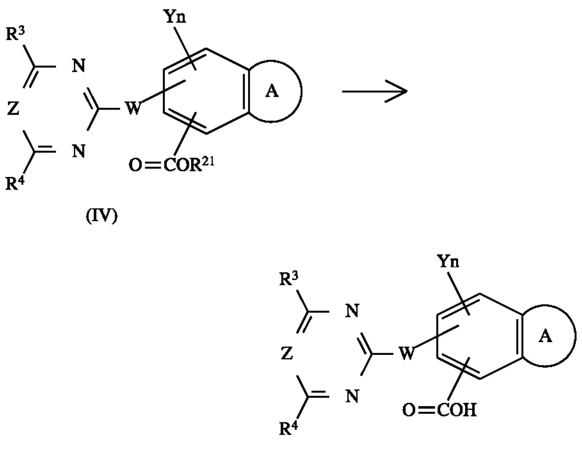

(IV)

(V)

(wherein $R^{21}$ is an alkyl group, an allyl group, a benzyl group or a trimethylsilylethyl group, and A, W, Y, Z, $R^3$, $R^4$ and n are as defined above.)

When $R^{21}$ is an alkyl group, a compound of the formula (V) can be produced by reacting a compound of the formula (IV) in water or in a suitable solvent containing water in the presence of an at least equimolar amount of a base at a temperature within a range of from room temperature to the boiling point of the solvent for from 0.5 to 24 hours, followed by acidifying.

As the base, an alkali metal hydroxide such as sodium hydroxide or potassium hydroxide, an alkali metal carbonate such as sodium carbonate or potassium carbonate, or an alkali metal hydrogen carbonate such as sodium hydrogen carbonate or potassium hydrogen carbonate, may be used.

As the solvent, an alcohol solvent such as methanol, ethanol or 2-propanol, an ether solvent such as diethyl ether, tetrahydrofuran or 1,4-dioxane, a ketone solvent such as acetone or methyl ethyl ketone, an aprotic polar solvent such as N,N-dimethylformamide, N,N-dimethylacetamide or diemthylsulfoxide, or other solvent such as acetonitrile, may, for example, be used.

When $R^{21}$ is an allyl group, a product can be produced by reacting such a compound with dimedone or with an allyl acceptor such as formic acid or n-butylamine in a solvent such as acetonitrile, diemthylformamide or tetrahydrofuran using a palladium catalyst such as tetrakistriphenylphosphine palladium (O) at a temperature within a range of from room temperature to the boiling point of the solvent for from 1 to 24 hours.

Further, when $R^{21}$ is a benzyl group, a product can be produced by hydrogenation in a suitable solvent using a platinum catalyst or palladium catalyst at an ordinary temperature under an ordinary pressure (if required, under heating and under pressure).

When $R^{21}$ is a trimethylsilylethyl group, a product can be produced by reacting such a material with an at least equimolar amount of tetrabutylammonium fluoride or the like in tetrahydrofuran at room temperature.

As the solvent, an alcohol solvent such as methanol or ethanol, an ester solvent such as methyl acetate or ethyl acetate, a ketone solvent such a.s acetone or methyl ethyl ketone, an ether solvent such as diethyl ether, 5 dioxane or tetrahydrofuran, or acetic acid, may, for example, be used.

Process 3

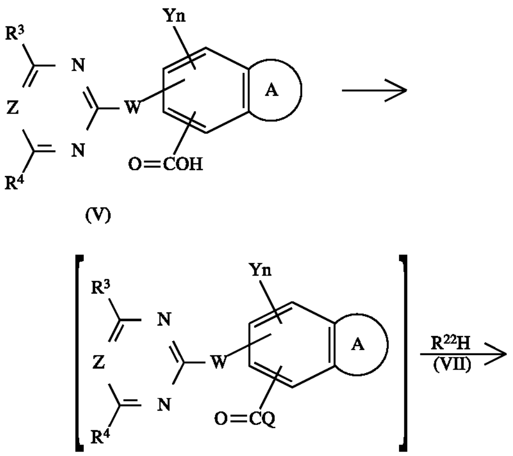

(V)

(VI)

-continued

Process 3

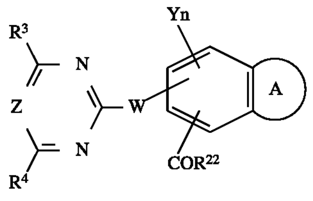

(I)

{wherein Q is a halogen atom, a cyano group, or an imidazolyl group, $R^{22}$ is an alkoxy group which may be substituted, a benzyloxy group which may be substituted, an isopropylidenaminoxy group, a phenyloxy group which may be substituted, a phenylthio group which may be substituted, an alkenyloxy group, an alkynyloxy group, an alkylthio group, or a group of the formula —$NR^6R^7$ (wherein each of $R^6$ and $R^7$ which may be the same or different, is a hydrogen atom, an alkyl group, a phenyl group which may be substituted, an alkylsulfonyl group, or a phenylsulfonyl group which may be substituted, or $R^6$ and $R^7$ may, together with the nitrogen atom, form a ring ), and $R^3$, $R^4$, A, W, Y, Z and n are as defined above.}

For the production of a compound of the formula (I) of the present invention, a compound of the formula (V) is reacted with an at least equimolar amount of a condensing agent in a suitable solvent at a temperature within a range of from −10° C. to the boiling point of the solvent for from 0.5 to 24 hours to obtain a compound of the formula (VI). After isolating or without isolating it, it is reacted with a compound of the formula (VII) together with an at least equimolar amount of a base in a suitable solvent at a temperature within a range of from −10° C. to the boiling point of the solvent for from 0.5 to 24 hours, to obtain a compound of the formula (I).

As the condensing agent, thionyl chloride, oxalic acid dichloride, a chlorocarbonic acid ester, carbonyl diimidazole, a cyanophospholic acid ester or a carbodiimide may, for example, be used.

As the base, an alkali metal such as metal sodium or metal potassium, an alkali metal hydride or alkaline earth metal hydride such as sodium hydride, potassium hydride or calcium hydride, an alkali metal alkoxide such as potassium t-butoxide, an alkali metal carbonate such as sodium carbonate or potassium carbonate, or an alkali metal hydroxide such as sodium hydroxide or potassium hydroxide, may, for example, be used.

As the solvent, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as methyl acetate or ethyl acetate, a ketone solvent such as acetone or methyl ethyl ketone, an aprotic polar solvent such as N,N-dimethylformamide, N,N-dimethylacetamide or dimethylsulfoxide, or other solvent such as acetonitrile, may, for example, be used.

Process 4

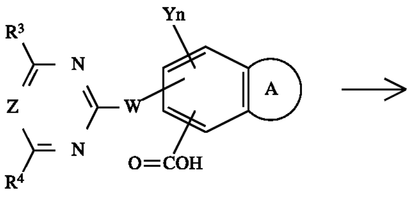

(V)

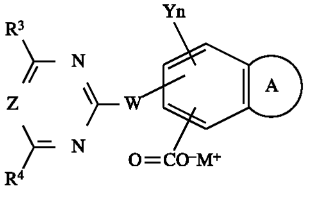

(VIII)

(wherein $R^3$, $R^4$, A, W, Y, Z and n are as defined above, and M is an alkali metal, an alkaline earth metal, ammonium or organic ammonium.)

A compound of the formula (VIII) can be produced by reacting the compound of the formula (V) together with an equimolar amount of a base in a suitable solvent at a temperature within a range of from room temperature to the boiling point of the solvent for from 0.5 to 24 hours.

As the base, an alkali metal hydroxide or alkaline earth metal hydroxide such as sodium hydroxide or calcium hydroxide, an alkali metal carbonate or alkaline earth metal carbonate such as sodium carbonate or calcium carbonate, an alkali metal hydride or alkaline earth metal hydride such as sodium hydride, potassium hydride or calcium hydride, an alkali metal alkoxide such as sodium methoxide or sodium ethoxide, an alkali metal hydrogen carbonate such as sodium hydrogen carbonate or potassium hydrogen carbonate, ammonia, or an organic amine such as isopropylamine, may, for example, be used.

As the solvent, a hydrocarbon solvent such as benzene, toluene or xylene, a halogenated hydrocarbon solvent such as dichloromethane or chloroform, an ester solvent such as methyl acetate or ethyl acetate, an alcohol solvent such as methanol, ethanol or 2-propanol, an ether solvent such as diethyl ether, tetrahydrofuran or dioxane, a ketone solvent such as acetone or methyl ethyl ketone, an aprotic polar solvent such as N,N-dimethylformamide, N,N-dimethylacetamide or dimethylsulfoxide, or other solvent such as acetonitrile or water, may, for example, be used.

Process 5

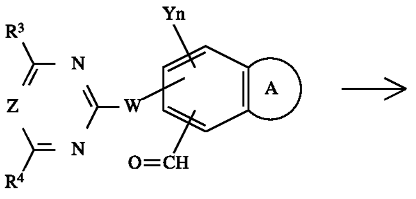

(IX)

-continued

Process 5

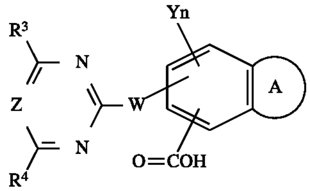

(V)

(wherein A, $R^3$, $R^4$, W, Y, Z and n are as defined above.)

The compound of the formula (V) of the present invention can be obtained by reacting the compound of the formula (IX) with a suitable oxidizing agent in a suitable solvent at a temperature within a range of from 0° C. to the boiling point of the solvent for from 0.5 to 24 hours.

As the oxidizing agent, a permanganate such as potassium permanganate, a chromic acid such as chromic anhydride, hydrogen peroxide, an organic peracid such as n-chloroperbenzoic acid, or nickel peroxide, may, for example, be used. As the solvent, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as methyl acetate or ethyl acetate, a ketone solvent such as acetone or methyl ethyl ketone, an aprotic polar solvent such as N,N-dimethylformamide, N,N-dimethylacetamide or dimethylsulfoxide, or other solvent such as acetonitrile or water, may, for example, be used.

Process 6

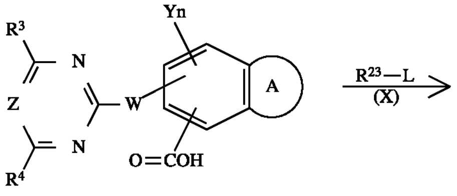

(V)

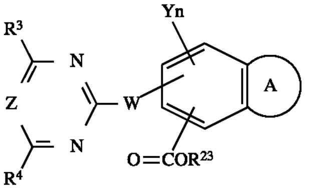

(XI)

(wherein $R^{23}$ is an alkyl group which may be substituted, a benzyl group which may be substituted, an alkenyl group, an alkynyl group, or a 2-trimethylsilylethoxymethyl group, $L^2$ is a hydrogen atom, and $R^3$, $R^4$, A, W, Y, Z and n are as defined above.)

A compound of the formula (XI) can be produced by reacting a compound of the formula (V) with a compound of the formula (X) in a suitable solvent in the presence of a base at a temperature within a range of from 10° C. to the boiling point of the solvent for from 0.5 to 24 hours.

As the base, an alkali metal hydroxide such as sodium hydroxide or potassium hydroxide, an alkali metal carbonate such as sodium carbonate or potassium carbonate, an alkali metal hydrogen carbonate such as sodium hydrogen carbonate or potassium hydrogen carbonate, or an alkali metal hydride such as sodium hydride, may, for example, be used.

As the solvent, a ketone solvent such as acetone or methyl ethyl ketone, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as methyl acetate or ethyl acetate, an aprotic polar solvent such as N,N-dimethylformamide, N,N-dimethylacetamide or dimethylsulfoxide, or other solvent such as acetonitrile, may, for example, be used.

Process 7

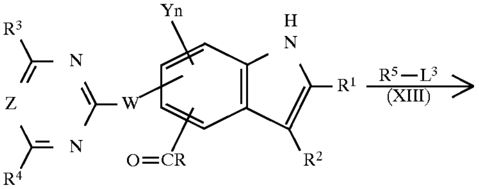

(XII)

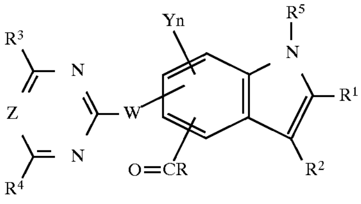

(XIV)

(wherein $L^3$ is a leaving group such as a halogen, and R, $R^1$, $R^2$, $R^3$, $R^4$, $R^5$, W and Z are as defined above, provided that $R^5$ excludes a hydrogen atom.)

A compound of the formula (XIV) can be produced by reacting a compound of the formula (XII) with a compound of the formula (XIII) in a suitable solvent in the presence of an at least equimolar amount of a base at a temperature within a range of from −10° C. to the boiling point of the solvent for from 0.5 to 24 hours.

As the base, an alkali metal such as metal sodium or metal potassium, an alkali metal hydride such as sodium hydride or potassium hydride, an alkali metal alkoxide such as potassium t-butoxide, an alkali metal carbonate such as sodium carbonate or potassium carbonate, or an alkali metal hydroxide such as sodium hydroxide or potassium hydroxide, may, for example, be used.

As the solvent, a hydrocarbon solvent such as toluene or xylene, a halogenated hydrocarbon solvent such as dichloromethane or chloroform, an ether solvent such as diethyl ether or tetrahydrofuran, a ketone solvent such as acetone, an aprotic polar solvent such as N,N-dimethylformamide or dimethylsulfoxide, or other solvent such as acetonitrile, may, for example, be used.

Process 8

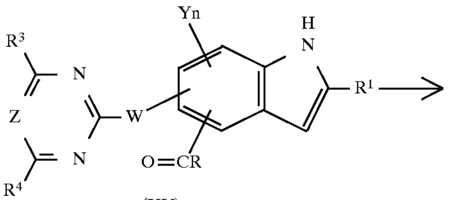

(XV)

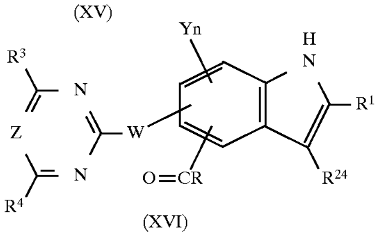

(XVI)

(wherein $R^{24}$ is a formyl group or a nitro group, and $R^1$, $R^3$, $R^4$, R, W, Y, Z and n are as defined above.)

A compound of the formula (XVI) can be obtained by subjecting the compound of the formula (XV) to a Vilsmeier reaction with phosphorus oxychloride in N,N-dimethylformamide to obtain a formyl product, or reacting it with a nitric acid ester in tetrahydrofuran in the presence of an alcoholate or reacting it with nitronium tetrafluoroborate in acetonitrile or in tetrahydrofuran at a temperature within a range of from −50° C. to the boiling point of the solvent, to obtain a nitro product.

Further, the obtained nitro product may be reduced by a conventional method to obtain an amino product, which can be led to various derivatives.

Among the compounds of the formula (I) of the present invention wherein A is (A-11), a compound of the formula (XIX) can be produced by the following process.

Process 9

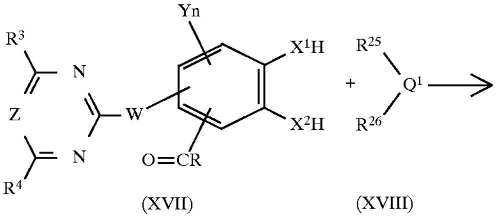

(XVII) (XVIII)

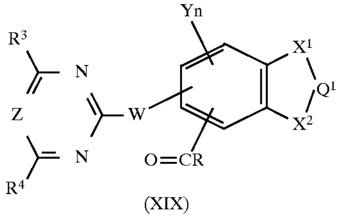

(XIX)

(wherein $X^1$ and $X^2$ represent an oxygen atom, a sulfur atom and $NR^{14}$ among those defined above, R, $R^3$, $R^4$, $R^{14}$, $Q^1$, W, Y, Z and n are as defined above, each of $R^{25}$ and $R^{26}$ which may be the same or different, is a chlorine atom, an alkoxy group or a lower alkylthio group.)

A compound of the formula (XIX) can be produced by reacting a compound of the formula (XVII) with a compound of the formula (XVIII) in a suitable solvent in the presence or absence of a base at a temperature within a range of from −30° C. to the boiling point of the solvent, preferably from 0° C. to 120° C., for from 0.5 to 24 hours.

As the base to be used, preferred is an organic base such as triethylamine, pyridine, N,N-diisopropylethylamine or N,N-dimethylaniline. However, an alkali metal hydride or an alkaline earth metal hydride such as sodium hydride, potassium hydride or calcium hydride, an alkali metal alkoxide such as potassium t-butoxide, an alkali metal carbonate such as sodium carbonate or potassium carbonate, or an alkali metal hydrogen carbonate such as sodium hydrogen carbonate or potassium hydrogen carbonate, may also be used.

As the solvent to be used, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as ethyl acetate, a ketone solvent such as acetone or methyl ethyl ketone, an aprotic polar solvent such as N,N-dimethylacetamide, N,N-dimethylformamide or dimethylsulfoxide, or other solvent such as acetonitrile, may, for example, be employed.

Among the compounds of the formula (I) of the present invention wherein A is (A-12), a compound of the formula (XII) can be produced by the following process.

Process 10

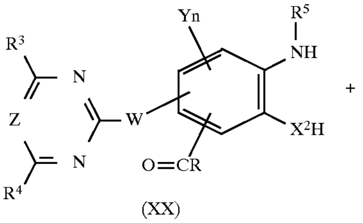

(XX)

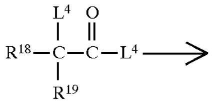

(XXI)

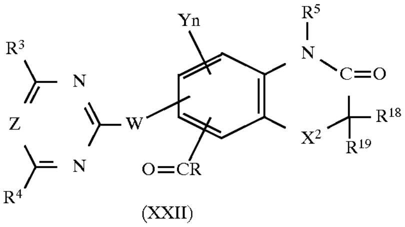

(XXII)

(wherein $R^5$, $R^{18}$ and $R^{19}$ represent a hydrogen atom and a lower alkyl group among those defined above, $X^2$ represents an oxygen atom, a sulfur atom and $NR^{14}$ among those defined above, $L^4$ is a chlorine atom or a bromine atom, and R, $R^3$, $R^4$, $R^{14}$, W. Y, Z and n are as defined above.)

A compound of the formula (XXII) can be produced by reacting a compound of the formula (XX) with a compound of the formula (XXI) in a suitable solvent in the presence of a base at a temperature within a range of from 0° C. to the boiling point of the solvent, preferably from 10° C. to 80° C., for from 1 to 20 hours.

As the base to be used, an alkali metal carbonate such as sodium carbonate or potassium carbonate, an alkali metal hydrogen carbonate such as sodium hydrogen carbonate or potassium hydrogen carbonate, an alkali metal hydride or alkaline earth metal hydride such as sodium hydride, potassium hydride or calcium hydride, an alkali metal hydroxide such as sodium hydroxide or potassium hydroxide, an alkali metal alkoxide such as potassium t-butoxide, or an organic base such as triethylamine, pyridine, N,N-diisopropylethylamine or N,N-dimethylaniline, may, for example, be employed.

As the solvent, a hydrocarbon solvent such as benzene, toluene or xylene, a halogenated hydrocarbon solvent such as dichloromethane or chloroform, an ether solvent such as diethyl ether, tetrahydrofuran or 1,4-dioxane, an ester solvent such as ethyl acetate, a ketone solvent such as acetone or methyl ethyl ketone, an aprotic polar solvent such as N,N-dimethylacetamide, N,N- dimethylformamide or dimethylsulfoxide, or other solvent such as acetonitrile, may, for example, be used.

Among the compounds of the formula (I) wherein A is (A-12), a compound of the formula (XXVI) can be produced in accordance with the following process.

Process 11

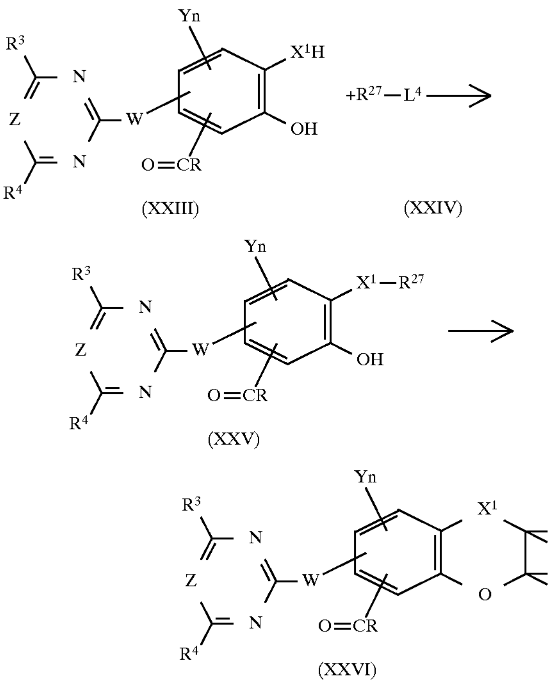

(XXIII) (XXIV)

(XXV)

(XXVI)

(wherein $R^{27}$ is a group of the formula $CR^{18}R^{19}$(—CH═$CHR^{18}$ or a group of the formula $CR^{18}R^{19}C{\equiv}CR^{18}$, $R^{18}$ and $R^{19}$ represent a hydrogen atom and a lower alkyl group among those defined above, $X^1$ represents an oxygen atom, a sulfur atom and $NR^{14}$ among those defined above, and $L^4$, R, $R^3$, $R^4$, $R^{14}$, W, Y, Z and n are as defined above.)

A compound of the formula (XXV) can be produced by reacting a compound of the formula (XXIII) with a compound of the formula (XXIV) in a suitable solvent in the presence of a base at a temperature within a range of from 0° C. to the boiling point of the solvent, preferably from 20° C. to 80° C., for from 1 to 24 hours.

As the base and the solvent to be used, the same as those described for Process 6 may be employed.

Further, a compound of the formula (XXVI) can be produced by subjecting a compound of the formula (XXV) to an intramolecular cyclization reaction in a suitable solvent in the presence of a suitable catalyst at a temperature of from 0° C. to the boiling point of the solvent, preferably from 20° C. to 150° C., for from 5 to 72 hours.

As the catalyst to be used, an alkali metal carbonate such as potassium carbonate or sodium carbonate, or silver oxide (yellow), may, for example, be mentioned.

As the solvent to be used, preferred is an alcohol solvent such as methanol or ethanol, or an aprotic polar solvent such as N,N-dimethylacetamide, N,N-dimethylformamide or dimethylsulfoxide. However, a hydrocarbon solvent such as benzene, toluene or xylene, a halogenated hydrocarbon solvent such as dichloromethane or chloroform, an ether solvent such as tetrahydrofuran or 1,4-dioxane, an ester solvent such as ethyl acetate, a ketone solvent such as acetone or methyl ethyl ketone, or other solvent such as acetonitrile, may also be used.

Among the compounds of the formula (I) of the present invention wherein A is (A-12), a compound of the formula (XXX) can be produced by the following process.

Process 12

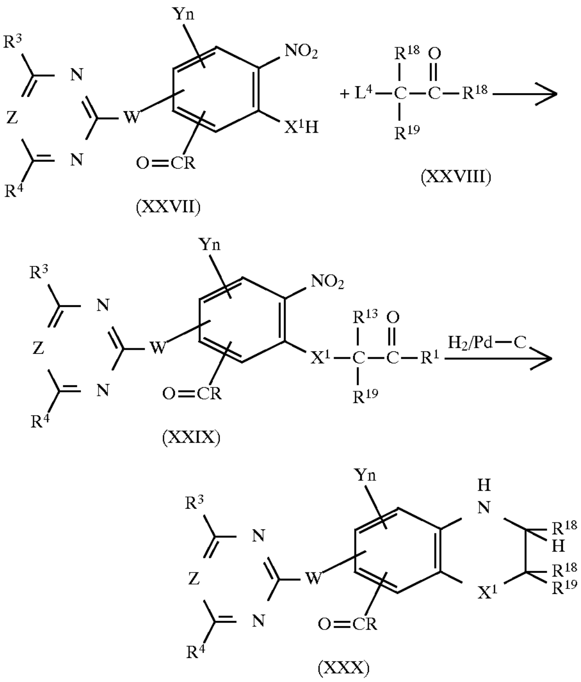

(XXVII) (XXVIII)

(XXIX)

(XXX)

(wherein $R^{18}$ and $R^{19}$ represent a hydrogen atom and a lower alkyl group among those defined above, $X^1$ represents an oxygen atom, a sulfur atom and $NR^{14}$ among those defined above, and $L^4$, R, $R^3$, $R^4$, $R^{14}$, W, Y, Z and n are as defined above.)

A compound of the formula (XXIX) can be produced by reacting a compound of the formula (XXVII) with a compound of the formula (XXVIII) in a suitable solvent in the presence of a base at a temperature within a range of from 0° C. to the boiling point of the solvent, preferably from 20° C. to 80° C., for from 3 to 24 hours. In this case, the reaction may be accelerated by an addition of an alkali metal iodide such as potassium iodide, as the case requires.

The base and the solvent to be used may be the same as those as described for Process 6.

Further, a compound of the formula (XXX) can be produced by subjecting a compound of the formula (XXIX) to hydrogenation in a suitable solvent in the presence of a palladium carbon catalyst at an ordinary temperature under an ordinary pressure for from 3 to 72 hours.

As the solvent to be used, preferred is an alcohol solvent such as methanol or ethanol. However, a hydrocarbon solvent such as benzene, toluene or xylene, an ether solvent such as tetrahydrofuran or 1,4-dioxane, an ester solvent such as ethyl acetate, a ketone solvent such as acetone or methyl ethyl ketone, or other solvent such as acetonitrile, may also be used.

Among the compounds of the formula (I) of the present invention wherein A is (A-12), a compound of the formula (XXXIV) can be produced by the following process.

Process 13

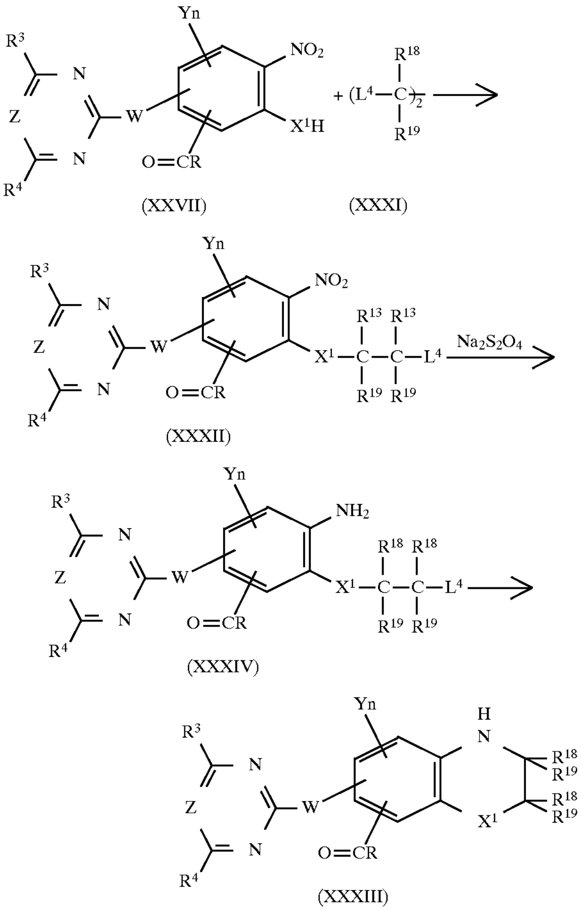

(XXVII) (XXXI) (XXXII) (XXXIV) (XXXIII)

(wherein $R^{18}$ and $R^{19}$ represent a hydrogen atom and a lower alkyl group among those defined above, $X^1$ represents an oxygen atom, a sulfur atom and $NR^{14}$ among those defined above, and $L^4$, R, $R^3$, $R^4$, $R^{14}$, W, Y. Z and n are as defined above.)

A compound of the formula (XXXII) can be produced by reacting a compound of the formula (XXVII) with a compound of the formula (XXXI) in a suitable solvent in the presence of a base at a temperature within a range of from 0° C. to the boiling point of the solvent, preferably from 20° C. to 80° C., for from 5 to 24 hours. In this case, the reaction may be accelerated by an addition of an alkali metal iodide such as potassium iodide, as the case requires.

A compound of the formula (XXXIII) can be produced by subjecting a compound of the formula (XXXIV) to an intramolecular cyclization reaction in a suitable solvent in the presence of a base at a temperature within a range of from 0° C. to the boiling point of the solvent, preferably from 20° C. to 80° C., for from 5 to 24 hours.

The base and the solvent to be used may be the same as those described for Process 6.

Further, a compound of the formula (XXXIV) can be produced by reducing a compound of the formula (XXXIII) in a suitable solvent using sodium hydrosulfite at a temperature within a range of from 0° C. to the boiling point of the solvent, preferably from 30° C. to 50° C., for from 0.1 to 1 hour.

As the solvent to be used, preferred is an alcohol solvent such as methanol or ethanol, or water. However, an ether solvent such as tetrahydrofuran or 1,4-dioxane, a ketone solvent such as acetone or methyl ethyl ketone, or other solvent such as acetonitrile, may be used in combination, as the case requires.

Now, the processes for the production of the compounds of the present invention, as well as methods for preparation of formulations and methods for application will be specifically described with reference to Examples.

BEST MODE FOR CARRYING OUT THE INVENTION

EXAMPLE 1

Preparation of 5-(4, 6-dimethoxypyrimidin-2-yl)oxy-4-formyl-3-methylbenzothiophene (Compound No. 104)

A mixture comprising 2.1 g of 4-formyl-5-hydroxy-3-methylbenzothiophene, 2.4 g of 4,6-dimethoxy-2-methylsulfonylpyrimidine and 1.8 g of potassium carbonate in 30 ml of N,N-dimethylformamide, was heated and stirred at 70° C. for 3 hours. The mixture was returned to room temperature, then poured into water and extracted with ethyl acetate. The organic layer was washed with water and then dried over anhydrous sodium sulfate. Then, it was concentrated under reduced pressure, and the oily substance thereby obtained was purified by silica gel column chromatography (n-hexane/ethyl acetate=10/1) to obtain 3.1 g (yield: 86%) of the desired compound.

EXAMPLE 2

Preparation of 5-(4,6-dimethoxypyrimidin-2-yl) oxy-3-methylbenzothiophene-4-carboxylic acid (Compound No. 105)

0.6 g of 5-(4,6-dimethoxypyrimidin-2-yl)oxy-4-formyl-3-methylbenzothiophene was dissolved in 80 ml of acetone. While stirring the solution at room temperature, 0.6 g of potassium permanganate dissolved in 10 ml of water was dropwise added thereto over a period of 15 minutes, and the mixture was further stirred at room temperature for 4 hours. It was then concentrated under reduced pressure to remove acetone, and then a saturated sodium bicarbonate aqueous solution was added thereto to make the mixture alkaline. The mixture was extracted with ethyl acetate, and then the aqueous layer was precipitated with 10% hydrochloric acid. The precipitated crystals were collected by filtration and washed with water to obtain 0.47 g (yield: 76%) of the desired compound.

EXAMPLE 3

Preparation of benzyl 5-(4,6-dimethoxypyrimidin-2-yl) oxy-3-ethoxycarbonyl-2-methylbenzofuran-4-carboxylate (Compound No. 1)

A mixture comprising 12.88 g of benzyl 3-ethoxycarbonyl-5-hydroxy-2-methylbenzofuran-5-carboxylate, 8.33 g of 4,6-dimethoxy-2-methylsulfonylpyrimidine and 5.53 g of potassium carbonate in 150 ml of N,N-dimethylformamide, was heated and stirred at 70° C. for 3 hours. The mixture was returned to room temperature, then poured into ice water and extracted with ethyl acetate. The organic layer was washed with water and then dried over anhydrous sodium sulfate. It was concentrated under reduced pressure, and the oily substance thereby obtained was purified by silica gel column chromatography (n-hexane/ethyl acetate=4/1) to obtain 14.45 g (yield: 81%) of the desired compound.

EXAMPLE 4

Preparation of 5-(4,6-dimethoxypyrimidin-2-yl) oxy-3-ethoxycarbonyl-2-methylbenzofuran-4-carboxylic acid (Compound No. 2)

A mixture comprising 14.4 g of benzyl 5-(4,6-dimethoxypyrimidin-2-yl) oxy-3-ethoxycarbonyl-2-methylbenzofuran-4-carboxylate and 4.52 g of 10% palladium carbon in 100 ml of ethanol, was subjected to hydrogenation under an ordinary pressure while stirring at room temperature. After completion of the reaction, an insoluble matter was separated by filtration, and the filtrate was concentrated under reduced pressure, whereupon the precipitated crystals were washed with a solvent mixture of diethyl ether/n-hexane to obtain 10.47 g (yield: 89%) of the desired compound.

EXAMPLE 5

Preparation of pivaloyloxymethyl 5-(4,6-dimethoxypyrimidin-2-yl) oxy-3-ethoxycarbonyl-2-methylbenzofuran-4-carboxylate (Compound No. 4)

A mixture comprising 0.40 g of 5-(4,6-dimethoxypyrimidin-2-yl) oxy-3-ethoxycarbonyl-2-methylbenzofuran-4-carboxylic acid, 0.26 g of chloromethyl pivalate and 0.21 g of potassium carbonate in 20 ml of N,N-dimethylformamide, was stirred at room temperature for 6 hours, then poured into ice water and extracted with ethyl acetate. The organic layer was washed with water and then dried over anhydrous sodium sulfate. It was concentrated under reduced pressure, and the oily substance thereby obtained was purified by silica gel column chromatography (n-hexane/ethyl acetate=4/1) to obtain 0.43 g (yield: 84%) of the desired compound.

EXAMPLE 6

Preparation of methyl 5-(4,6-dimethoxypyrimidin-2-yl) oxybenzoxazol-4-carboxylate (Compound No. 446) A mixture comprising 0.6 g of methyl 5-hydroxybenzoxazol-4-carboxylate, 0.6 g of 2-chloro-4,6-dimethoxypyrimidine and 0.7 g of potassium carbonate in 30 ml of N,N-dimethylformamide, was heated and stirred at 115° C. for two hours. The mixture was returned to room temperature, then poured into water and extracted with ethyl acetate. The organic layer was washed with water, dried over anhydrous sodium sulfate and then concentrated under reduced pressure. The oily substance thereby obtained was purified by silica gel column chromatography (n-hexane/ethyl acetate =5/1) to obtain 0.4 g (yield: 39%) of the desired compound.

EXAMPLE 7

Preparation of methyl 6-(4, 6-dimethoxy-1,3,5-triazin-2-yl) oxybenzoxazol-7-carboxalate (Compound No. 464)

0.6 g of methyl 6-hydroxyybenzoxazol-7-carboxylate, 0.55 g of 2-chloro-4,6-dimethoxy-1,3,5-triazine and 0.5 g of potassium carbonate in 30 ml of N,N-dimethylformamide were heated and stirred at 115° C. for 3 hours. The mixture was returned to room temperature, then poured into water and extracted with ethyl acetate. The organic layer was washed with water, dried over anhydrous sodium sulfate and then concentrated under reduced pressure. The oily substance thereby obtained was purified by silica gel column chromatography (n-hexane/ethyl acetate=5/1) to obtain 0.6 g (yield: 58%) of the desired compound.

EXAMPLE 8

Preparation of methyl 5-(4,6-dimethoxypyrimidin-2-yl) oxy-2-ethoxy-2,3-dihydrobenzofuran-4-carboxylate (Compound No. 507)

A mixture comprising 1.0 g of methyl 2-ethoxy-5-hydroxy-2,3-dihydrobenzofuran-4-carboxylate, 1.0 g of 4,6-dimethoxy-2-methylsulfonylpyrimidine and 0.78 g of potassium carbonate in 30 ml of N,N-dimethylformamide, was heated and stirred at 100° C. for two hours. The mixture was returned to room temperature, then poured into water and extracted with ethyl acetate. The organic layer was washed with water and then dried over anhydrous sodium sulfate. It was concentrated under reduced pressure, and the oily substance thereby obtained was purified by silica gel column chromatography (n-hexane/ethyl acetate =4/1) to obtain 1.5 g (yield; 95%) of the desired compound.

EXAMPLE 9

Preparation of 5-(4,6-dimethoxypyrimidin-2-yl) oxy-2-ethoxy-2,3-dihydrobenzofuran-4-carboxylic acid (Compound No. 508)

While stirring 1.2 g of methyl 5-(4,6-dimethoxypyrimidin-2-yl) oxy-2-ethoxy-2,3-dihydrobenzofuran-4-carboxylate in 20 ml of dimethylsulfoxide at room temperature, 2 ml of a 2N sodium hydroxide aqueous solution was dropwise added thereto over a period of 10 minutes and then the mixture was further stirred for 15 hours. The mixture was poured into water and extracted with diethyl ether. Then, the aqueous layer was acidified with 10% hydrochloric acid, and precipitated crystals were extracted with ethyl acetate, and the organic layer was washed with water and then dried over anhydrous sodium sulfate. It was concentrated under reduced pressure, and the oily substance thereby obtained was purified by silica gel column chromatography (n-hexane/ethyl acetate=1/1) to obtain 1.0 g (yield: 87%) of the desired compound.

EXAMPLE 10

Preparation of sodium 3-benzoyl-5-(4, 6-dimethoxypyrimidin-2-yl) oxy-2-trifluoromethylbenzofuran-4-carboxylate (Compound No. 77)

While stirring 0.35 g of sodium hydride in 30 ml of N,N-dimethylformamide at room temperature, 1.73 g of 3-benzoyl-5-hydroxy-2-trifluoromethylbenzofuran-4-carboxylic acid was gradually added thereto. After completion of the addition, the mixture was further stirred for one hour. While stirring this mixture at room temperature, 1.08 g of 4,6-dimethoxy-2-methylsulfonylpyrimidine was added thereto, and then the mixture was stirred at 70° C. for 3 hours. The mixture was returned to room temperature and poured into water. Precipitated crystals were separated by filtration and washed with water and acetone to obtain 1.02 g (yield: 40.5%) of the desired compound.

EXAMPLE 11

Preparation of benzyl 5-(4,6-dimethoxy-1,3, 5-triazin-2-yl) oxy-2-methyl-3-methoxycarbonylbenzofuran-4-carboxylate (Compound No. 32)

A mixture comprising 2 g of benzyl 5-hydroxy-2-methyl-3-methoxycarbonylbenzofuran-4-carboxylate, 1 g of 4,6-dimethoxy-2-methylsulfonyl-1,3,5-triazine and 1 g of potassium carbonate in 20 ml of N,N-dimethylformamide, was heated and stirred at 70° C. for two hours. The mixture was returned to room temperature, poured into ice water and extracted with ethyl acetate. The organic layer was washed with water and then dried over anhydrous sodium sulfate. Then, it was concentrated under reduced pressure, and the obtained solid was thoroughly washed with ethanol to obtain 2.4 g (yield: 86%) of the desired compound.

EXAMPLE 12

Preparation of methyl 6-(4,6-dimethoxypyrimidin-2-yl) oxy-3-methyl-benzisoxazol-7-carboxylate (Compound No. 487)

A mixture comprising 1.3 g of methyl 6-hydroxy-3-methyl-benzisoxazol-7-carboxylate, 1.4 g of 4,6-dimethoxy- 2-methylsulfonylpyrimidine and 1 g of potassium carbonate in 20 ml of N,N-dimethylformamide, was heated and stirred at 70° C. for two hours. The mixture was returned to room temperature, poured into ice water and extracted with ethyl acetate. The organic layer was washed with water and then dried over anhydrous sodium sulfate. Then, it was concentrated under reduced pressure, and the obtained crystals were thoroughly washed with isopropyl ether to obtain 1.6 g (yield: 73%) of the desired compound.

EXAMPLE 13

Preparation of 6-(4,6-dimethoxypyrimidin-2-yl) oxy-3-methyl-benzisoxazol-7-carboxylic acid (Compound No. 488)

While heating and stirring 1.0 g of methyl 6-(4,6-dimethoxypyrimidin-2-yl)oxy-3-methylbenzisoxazol-7-carboxylate in 20 ml of N,N-dimethylsulfoxide at 70° C., 1.7 ml of a 2N sodium hydroxide aqueous solution was dropwise added thereto over a period of 10 minutes. Then, the mixture was further heated and stirred at 70° C. for 30 minutes. The mixture was returned to room temperature, then poured into water and extracted with diethyl ether. The aqueous layer was acidified with 10% hydrochloric acid, and precipitated crystals were extracted with ethyl acetate. The organic layer was washed with water and then dried over anhydrous sodium sulfate. It was then concentrated under reduced pressure, and the crystals thereby obtained were washed with isopropyl ether to obtain 0.7 g (yield: 71%) of the desired compound.

EXAMPLE 14

Preparation of sodium 6-(4,6-dimethoxypyrimidin-2-yl) oxy-3-methoxycarbonyl-2-methylbenzofuran-4-carboxylate (Compound No. 130)

While stirring 0.5 g of 5-(4, 6-dimethoxypyrimidin-2-yl) oxy-3-methoxycarbonyl-2-methyl-benzofuran-4-carboxylic acid in 5 ml of tetrahydrofuran at room temperature, 0.05 g of 60% sodium hydride was added thereto. The mixture was stirred at room temperature for 6 hours. Then, precipitated crystals were collected by filtration and washed with isopropyl ether to obtain 0.40 g (yield: 75%) of the desired compound.

EXAMPLE 15

Preparation of N-[5-(4,6-dimethoxypyrimidin-2-yl) oxy-3-ethoxycarbonyl-2-methylbenzofuran-4-carbonyl]imidazole (Compound No. 16)

While stirring 0.8 g of 5-(4, 6-dimethoxypyrimidin-2-yl) oxy-3-ethoxycarbonyl-2-methyl-benzofuran-4-carboxylic acid in 30 ml of tetrahydrofuran at room temperature, 0.36 g of carbonyldiimidazole was added thereto. The mixture was stirred at room temperature for one hour and then concentrated under reduced pressure. The residue was dissolved in ethyl acetate and washed with water. It was dried over anhydrous sodium sulfate and then concentrated under reduced pressure, and the crystals thereby obtained were washed with n-hexane to obtain 0.81 g (yield: 90%) of the desired compound.

EXAMPLE 16

Preparation of 4-allyloxycarbonyl-5-(4, 6-dimethoxypyrimidin-2-yl)oxy-2-methylbenzofuran-3-carboxylic acid (Compound No. 371)

A mixture comprising 54.2 g of 4-allyloxycarbonyl-5-hydroxy-2-methylbenzofuran-3-carboxylic acid, 47 g of 4,6-dimethoxy-2-methylsulfonylpyridine and 65 g of potassium carbonate in 200 ml of N,N-dimethylformamide, was heated and stirred at 70° C. for two hours. The mixture was returned to room temperature, and then the reaction solution was poured into water and extracted with ethyl acetate. The organic layer was washed with water and then dried over anhydrous magnesium sulfate. Crystals obtained by concentration under reduced pressure, were washed with isopropyl ether to obtain 79.2 g (yield: 98%) of the desired compound.

EXAMPLE 17

Preparation of 4-allyloxycarbonyl-5-(4, 6-dimethoxypyrimidin-2-yl)oxy-2-methylbenzofuran-2-carbonyl chloride (Compound No. 254)

30.4 g of 4-allyloxycarbonyl-5-(4, 6-dimethoxypyrimidin-2-yl) oxy-2-methylbenzofuran-3-carboxylic acid was dissolved in 73 ml of thionyl chloride, and the solution was heated and stirred at 60° C. for 30 minutes. It was returned to room temperature, and then thionyl chloride was concentrated under reduced pressure. Toluene was added thereto, followed by further concentration. To the obtained oily substance, hexane was added for crystallization to obtain 31.4 g (yield: 99%) of the desired compound.

EXAMPLE 18

Preparation of allyl 5-(4,6-dimethoxypyrimidin-2-yl) oxy-3-dimethylcarbamoyl-2-methylbenzofuran-4-carboxylate (Compound No. 248)

3.0 g of 4-allyloxycarbonyl-5-(4, 6-dimethoxypyrimidin-2-yl)oxy-2-methylbenzofuran-3-carbonyl chloride was dissolved in 13 ml of dichloromethane, and 1.5 g of a 50% dimethylamine aqueous solution was dropwise added thereto under cooling with ice. After stirring for 30 minutes, the reaction solution was poured into water and extracted with dichloromethane. The organic layer was washed with water and then dried over anhydrous sodium sulfate. The oily substance obtained by concentration under reduced pressure, was purified by silica gel column chromatography (n-hexane/ethyl acetate=4/1) to obtain 1.84 g (yield; 60%) of the desired compound.

EXAMPLE 19

Preparation of 5-(4,6-dimethoxypyrimidin-2-yl) oxy-3-dimethylcarbamoyl-2-methylbenzofuran-4-carboxylic acid (Compound No. 247)

1.40 g of allyl 5-(4,6-dimethoxypyrimidin-2-yl) oxy-3-dimethylcarbamoyl-2-methylbenzofuran-4-carboxylate and 0.29 g of formic acid were dissolved in 12 ml of tetrahydrofuran, and 37 mg of tetrakistriphenylphosphine palladium (0) was added thereto under a nitrogen atmosphere. The mixture was heated and stirred at 50° C. for 3 hours. The mixture was returned to room temperature, and then isopropyl ether was added to the reaction solution. Precipitated crystals were collected by filtration to obtain 1.02 g (yield: 80%) of the desired compound.

EXAMPLE 20

Preparation of allyl 5-(4,6-dimethoxypyrimidin-2-yl) oxy-3-ethylthiocarbonyl-2-methylbenzofuran-4-carboxylate (Compound No. 152)

3.0 g of 4-allyloxycarobnyl-5-(4, 6-dimethoxypyrimidin-2-yl)oxy-2-methylbenzofuran-3-carbonyl chloride and 0.88 g of triethylamine were dissolved in 13 ml of dichloromethane, and 0.56 g of ethyl mercaptan was dropwise added thereto under cooling with ice. After stirring for 30 minutes, the reaction solution was poured into water and extracted with dichloromethane. The organic layer was washed with water, then dried over anhydrous sodium sulfate and concentrated under reduced pressure. The oily substance thereby obtained was purified by silica gel column chromatography (n-hexane/ethyl acetate =4/1) to obtain 1.74 g (yield: 55%) of the desired compound.

EXAMPLE 21

Preparation of 5-(4,6-dimethoxypyrimidin-2-yl) oxy-3-ethylthiocarbonyl-2-methylbenzofuran-4-carboxylic acid (Compound No. 153)

1.60 g of allyl 5-(4,6-dimethoxypyrimidin-2-yl) oxy-3-ethylthiocarbonyl-2-methylbenzofuran-4-carboxylate and 0.54 g of dimedone were dissolved in 14 ml of tetrahydrofuran, and 40 mg of tetrakistriphenylphosphine palladium (0) was added thereto under a nitrogen atmosphere. The mixture was stirred at room temperature for 3 hours. The reaction solution was concentrated under reduced pressure, and the residue was purified by silica gel column chromatography (n-hexane/ethyl acetate=2/1) to obtain 1.33 g (yield: 91%) of the desired compound.

EXAMPLE 22

Preparation of 2-trimethylsilylethoxymethyl 5-(4,6-dimethoxypyrimidin-2-yl) oxy-3-(4-methoxybenzyloxycarbonyl)-2-methylbenzofuran-4-carboxylate (Compound No. 369) 13.5 g of 5-(4,6-dimethoxypyrimidin-2-yl) oxy-3-(4-methoxybenzyloxycarbonyl)-2-methylbenzofuran-4-carboxylic acid and 3.3 g of triethylamine were dissolved in 120 ml of dichloromethane, and 5.0 g of 2-trimethylsilylethoxymethyl chloride was dropwise added thereto under cooling with ice. After stirring for 30 minutes, the reaction solution was poured into water and extracted with dichloromethane. The organic layer was washed with water, then dried over anhydrous magnesium sulfate and concentrated under reduced pressure. The residue thereby obtained was purified by silica gel column chromatography (n-hexane/ethyl acetate =4/1) to obtain 14.0 g (yield: 82%) of the desired compound.

EXAMPLE 23

Preparation of methyl 6-[(4, 6-dimethoxypyrimidin-2-yl) oxy]quinolin-5-carboxylate (Compound No. 904)

0.8 g of methyl 6-hydroxyquinolin-5-carboxylate, 0.96 g of 4,6-dimethoxy-2-methylsulfonylpyridine and 0.82 g of potassium carbonate were stirred in 30 ml of N,N-dimethylformamide at 80° C. for 3 hours. The mixture was returned to room temperature, then poured into ice water and extracted with ethyl acetate. The organic layer was washed with water and then dried over anhydrous magnesium sulfate. The residue obtained by concentration under reduced pressure, was crystallized from a solvent mixture of dichloromethane/isopropyl ether to obtain 1.21 g (yield: 89.0%) of the desired compound. mp: 160°–162° C.

EXAMPLE 24

Preparation of 6-[(4, 6-dimethoxypyrimidin-2-yl)oxy] quinolin-5-carboxylic acid (Compound No. 903)

0.8 g of methyl 6-[(4, 6-dimethoxypyrimidin-2-yl)oxy] quinolin-5-carboxylate was dissolved in 10 ml of methanol and 20 ml of methoxyethane, and 5 ml of an aqueous solution containing 0.39 g of potassium hydroxide was added thereto at 40° C. The mixture was extracted with dichloromethane. The aqueous layer was acidified (pH=4) with a 10% hydrochloric acid aqueous solution, and formed precipitates were collected by filtration and dried to obtain 0.5 g (yield: 66.0%) of the desired compound. mp: 195°–198° C.

EXAMPLE 25

Preparation of benzyl 5-[(4, 6-dimethoxypyrimidin-2-yl) oxy]2-methylindol-4-carboxylate (Compound No. 664)

A mixture comprising 2.2 g of benzyl 5-hydroxy-2-methylindol-4-carboxylate, 1.7 g of 4,6-dimethoxy-2-methylsulfonylpyrimidine and 1.3 g of potassium carbonate in 20 ml of N,N-dimethylformamide, was heated and stirred at a temperature of from 70° to 80° C. for two hours. The mixture was returned to room temperature, then poured into ice water and extracted with ethyl acetate. The organic layer was washed with water and then dried over anhydrous magnesium sulfate. The residue obtained by concentration under reduced pressure, was crystallized from isopropyl ether to obtain 2.8 g (yield: 85%) of the desired product. mp: 135°–139° C.

EXAMPLE 26

Preparation of benzyl 5-[(4, 6-dimethoxypyrimidin-2-yl) oxy]-3-formyl-2-methylindol-4-carboxylate (Compound No. 680)

0.46 ml of phosphorus oxychloride was dropwise added to 1.8 ml of N,N-dimethylformamide under cooling with ice, and the mixture was stirred for 30 minutes. Then, 2.3 g of benzyl 5-[(4,6-dimethoxypyrimidin-2-yl) oxy]-2-methylindol-4-carboxylate was dissolved in 10 ml of N,N-dimethylformamide, and the solution was dropwise added to the above mixture under cooling with ice. The mixture was stirred for 30 minutes, and then poured into ice water. An aqueous sodium hydroxide solution was added thereto for adjustment to pH9, followed by extraction with ethyl acetate. The organic layer was washed with water and dried over anhydrous magnesium sulfate. The residue obtained by concentration under reduced pressure, was crystallized from isopropyl ether to obtain 2 g (yield: 81.5%) of the desired compound. mp: 148°–149° C.

EXAMPLE 27

Preparation of allyl 5-[(4, 6-dimethoxypyrimidin-2-yl) oxy] -2-methyl-3-nitroindol-4-carboxylate (Compound No. 759)

2.0 g of allyl 5-[(4, 6-dimethoxypyrimidin-2-yl)oxy]-2-methylindol-4-carboxylate was dissolved in 25 ml of acetonitrile, and the solution was cooled to −30° C. 16.3 ml of a 0.5M sulfolane solution of nitronium tetrafluoroborate was dropwise added thereto, and the mixture was stirred for 5 hours. After adding 2 ml of aqueous ammonia, the mixture was returned to room temperature and extracted with ethyl acetate. The organic layer was washed with water and then dried over anhydrous sodium sulfate. Crystals obtained by concentration under reduced pressure, were washed with hexane to obtain 1.23 g (yield: 55%) of the desired compound.

EXAMPLE 28

Preparation of allyl 3-amino-5-[(4, 6-dimethoxypyrimidin-2-yl) oxy]-2-methylindol-4-carboxylate (Compound No. 722)

3.4 g of allyl 5-[(4,6-dimethoxypyrimidin-2-yl) oxy]-2-methyl-3-nitroindol-4-carboxylate was dissolved in 50 ml of methanol, and 5 ml of concentrated hydrochloric acid was added thereto. Then, 4.9 g of tin powder was gradually added at room temperature. Them, the mixture was stirred at room temperature for 12 hours. The solid was filtered off, and then residue was concentrated under reduced pressure and extracted with ethyl acetate. The organic layer was washed with water and then dried over anhydrous sodium sulfate. The residue obtained by concentration under reduced pressure, was crystallized from isopropyl ether to obtain 2.5 g (yield: 79%) of the desired product. mp: 132°–135° C.

EXAMPLE 29

Preparation of allyl 3-acetylamino-5-[(4, 6-dimethoxypyrimidin-2-yl)oxy]-2-methylindol-4-carboxylate (Compound No. 735)

0.5 g of allyl 5-[(4,6-dimethoxypyrimidin-2-yl) oxy]-2-methylindol-4-carboxylate was dissolved in 10 ml of pyridine, and 0.16 g of acetic anhydride was added thereto. The mixture was stirred for 12 hours. The reaction solution was poured into ice water and extracted with ethyl acetate. The organic layer was washed with water and then dried over anhydrous magnesium sulfate. The residue obtained by concentration under reduced pressure, was crystallized with isopropyl ether to obtain 0.49 g (yield: 87%) of the desired compound. mp: 177°–180° C.

EXAMPLE 30

Preparation of 3-acetylamino-5-[(4, 6-dimethoxypyrimidin-2-yl) oxy]-2-methylindol-4-carboxylic acid (Compound No. 736)

0.49 g of allyl 3-acetylamino-5-[(4, 6-dimethoxypyrimidin-2-yl)oxy]-2-methylindol-4-carboxylate was dissolved in 10 ml of tetrahydrofuran, and 0.1 g of dimedone and 0.01 g of tetrakistriphenylphosphine palladium were added thereto. The mixture was stirred at room temperature for 4 hours. Crystals obtained by concentration under reduced pressure, was washed with isopropyl ether to obtain 0.41 g (yield: 93%) of the desired compound. mp: 230°–233° C.

EXAMPLE 31

Preparation of benzyl-1-benzoyl-5-[(4, 6-dimethoxypyrimidin-2-yl) oxy]-3-ethoxycarbonyl-2-methylindol-4-carboxylate (Compound No. 796)

1.5 g of benzyl 5-[(4,6-dimethoxypyrimidin-2-yl) oxy]-3-ethoxycarbonyl-2-methylindol-4-carboxylate was dissolved in 50 ml of tetrahydrofuran, and 0.176 g of 60% sodium hydride was added thereto. The mixture was stirred at room temperature for 30 minutes. Then, 0.51 g of benzoyl chloride was dropwise added thereto at room temperature, and the mixture was stirred for 4 hours. After concentration under reduced pressure, the mixture was poured into ice water and extracted with ethyl acetate. The organic layer was washed with water and then dried over anhydrous magnesium sulfate. The residue obtained by concentration under reduced pressure, was crystallized from isopropyl ether to obtain 1.67 g (yield: 92%) of the desired compound. mp: 128°–132.5° C.

EXAMPLE 32

Preparation of l-benzoyl-5-[(4, 6-dimethoxypyrimidin-2-yl) oxy]-3-ethoxycarbonyl-2-methylindol-4-carboxylic acid (Compound No. 797)

1.6 g of benzyl 1-benzoyl-5-[(4, 6-dimethoxypyrimidin-2-yl) oxy]-3-ethoxycarbonyl-2-methylindol-4-carboxylate was dissolved in 50 ml of ethyl acetate, and 0.1 g of 10% palladium carbon was added thereto. Then, catalytic reduction was conducted. Insoluble matters were filtered off, and then filtrate was concentrated under reduced pressure. The residue thereby obtained was washed with isopropyl ether to obtain 1.28 g (yield: 97%) of the desired compound. mp: 113°–115° C.

EXAMPLE 33

Preparation of (2-trimethylsilyl)ethyl 6-[(4, 6-dimethoxypyrimidin-2-yl) oxy]-2-oxobenzoxazolin-7-carboxylate (Compound No. 853)

1.18 g of triphosgene was gradually added at room temperature to a mixture comprising 2.45 g of (2-trimethylsilyl)ethyl 3-amino-2-hydroxy-6-[(4, 6-dimethoxypyrimidin-2-yl)oxy]benzoate and 5 ml of triethylamine in 20 ml of dichloromethane. The mixture was stirred at room temperature for one hour, then poured into water and extracted with ethyl acetate. The organic layer was washed with water, 10% hydrochloric acid and a saturated sodium chloride aqueous solution and dried over anhydrous magnesium sulfate. The residue obtained by concentration under reduced pressure, was purified by silica gel column chromatography to obtain 2.25 g (yield: 97%) of the desired compound. (Yield: 86.5%) Refractive index: unmeasurable

EXAMPLE 34

Preparation of (2-trimethylsilyl)ethyl 7-[(4, 6-dimethoxypyrimidin-2-yl) oxy]-3-oxo-3,4-dihydro-2H-1, 4-benzooxadin-8-carboxylate (Compound No. 878)

0.60 g of chloroacetyl chloride was gradually dropwise added at 10° C. to a mixture comprising 2.04 g of (2-trimethylsilyl)ethyl 3-amino-2-hydroxy-6-[(4,6-dimethoxypyrimidin-2-yl) oxy]benzoate and 1.38 g of potassium carbonate in 15 ml of N,N-dimethylformamide, and then the mixture was gradually returned to room temperature and stirred for 5 hours. Further, the mixture was stirred at 50° C. for two hours to complete the reaction. The mixture was returned to room temperature, then poured into water, adjusted to pH3 with 10% hydrochloric acid and extracted with ethyl acetate. The organic layer was washed with water and a saturated sodium chloride aqueous solution and then dried over anhydrous magnesium sulfate. The residue obtained by concentration under reduced pressure, was purified by silica gel column chromatography to obtain 1.01 g (yield: 41.8%) of the desired compound. mp: 148°–150° C.

EXAMPLE 35

Preparation of (2-trimethylsilyl)ethyl 7-[(4, 6-dimethoxypyrimidin-2-vl) oxy]-2-methylene-3, 4-dihydro-2H-1,4-benzoxadin-8-carboxylate (Compound No. 896)

A mixture comprising 4.20 g of (2-trimethylsilyl)ethyl 3-amino-2-hydroxy-6-[(4, 6-dimethoxypyrimidin-2-yl) oxy] benzoate, 1.68 g of sodium carbonate and 1.42 g of propargyl bromide in 20 ml of N,N-dimethylformamide was heated and stirred at 50° C. for 4 hours. The mixture was returned to room temperature, then poured into water and extracted with ethyl acetate. The organic layer was washed with water and a saturated sodium chloride aqueous solution and then dried over anhydrous magnesium sulfate. The residue obtained by concentration under reduced pressure, was purified by silica gel column chromatography to obtain 2.90 g (yield: 63.9%) of (2-trimethylsilyl) ethyl 2-hydroxy-3-propargylamino-6-[(4, 6-dimethoxypryrimidin-2-yl)oxy] benzoate.

A mixture comprising 2.80 g of (2-trimethylsilyl)ethyl 2-hydroxy-3-propargylamino-6-[(4, 6-imethoxypyrimidin-2-yl)oxy]benzoate thus obtained and 0.20 g of mercury oxide (yellow) in 10 ml of N,N-imethylfromamide was heated and stirred under a nitrogen stream at 150° C. for two hours. The mixture was returned to room temperature, then poured into water and extracted with ethyl acetate. The organic layer was washed with water and a saturated sodium chloride aqueous solution and then dried over anhydrous magnesium sulfate. The residue obtained by concentration under reduced pressure, was purified by silica gel column chromatography to obtain 1.80 g of the desired compound. Refractive index: unmeasurable

EXAMPLE 36

Preparation of (2-trimethylsilyl)ethyl 7-[(4, 6-dimethoxypyrimidin-2-yl) oxy]-3-methyl-3,4-dihydro-2H-1,4-benzooxadin-8-carboxylate (Compound No. 890)

1.20 g of chloroacetone was gradually dropwise added at 10° C. to a mixture comprising 3.50 g of (2-trimethylsilyl) ethyl 2-hydroxy-3-nitro-6-[(4, 6-dimethoxypyrimidin-2-yl) oxy]benzoate, 1.80 g of potassium carbonate and 1.33 g of potassium iodide in 20 ml of acetone. Then, mixture was gradually returned to room temperature and stirred for 8 hours. Insoluble matters were filtered off, and the filtrate was concentrated under reduced pressure, poured into water and extracted with ethyl acetate. The organic layer was washed with water and a saturated sodium chloride aqueous solution and then dried over anhydrous magnesium sulfate. The residue obtained by concentration under reduced pressure, was purified by silica gel column chromatography to obtain 3.70 g (yield: 63.9%) of (2-trimethylsilyl)ethyl 2-acetonyloxy-3-nitro-6-[(4,6-dimethoxypyrimidin-2-yl) oxy]benzoate (yield: 93.7%)

3.60 g of (2-trimethylsilyl) ethyl-2-acetonitrileoxy-3-nitro-6-[(4, 6-dimethoxypyrimidin-2-yl)oxy]benzoate thus obtained was subjected to catalytic reduction under an ordinary pressure in 100 ml of methanol by means of 0.5 g of 10% palladium carbon. The reaction was terminated when the theoretical amount of about 700 ml of hydrogen was consumed. Palladium carbon was filtered off, and the filtrate was concentrated under reduced pressure. The residue thereby obtained was purified by silica gel column chromatography to obtain 3.10 g (yield: 94.8%) of the desired compound. Refractive index: unmeasurable

EXAMPLE 37

Preparation of (2-trimethylsilyl)ethyl 7-[(4, 6-dimethoxypyrimidin-2-yl) oxy]-3,4-dihydro-2H-1,4-benzooxadin-8-carboxylate (Compound No. 884)

A mixture comprising 3.50 g of (2-trimethylsilyl)ethyl 2-hydroxy-3-nitro-6-[(4, 6-dimethoxypyrimidin-2-yl)oxy] benzoate, 3.40 g of potassium carbonate and 9.40 g of 1,2-dibromoethane in 20 ml of N,N-dimethylformamide was heated and stirred at 80° C. for two hours. The mixture was returned to room temperature, then poured into water and extracted with ethyl acetate. The organic layer was washed with water and a saturated sodium chloride aqueous solution and then dried over anhydrous magnesium sulfate. The residue obtained by concentration under reduced pressure, was purified by silica gel column chromatography to obtain 3.60 g (yield: 82.8%) of (2-trimethylsilyl)ethyl 2-(2-bromoethoxy)-3-nitro-6-[(4, 6-dimethoxypyrimidin-2-yl) oxy]benzoate. 3.60 g of (2-trimethylsilyl)ethyl 2-(2-bromoethoxy-3-nitro-6-[(4, 6-dimethoxypyrimidin-2-yl) oxy]benzoate thus obtained and 7.00 g of 70% sodium hydrosulfite in a solvent mixture of water (15 ml) and methanol (30 ml) were stirred at room temperature for 20 minutes. The mixture was poured into water, saturated with sodium chloride and extracted with ethyl acetate. The organic layer was concentrated under reduced pressure and then extracted with ethyl acetate. The organic layer was washed with water and a saturated sodium chloride aqueous solution and then dried over anhydrous magnesium sulfate. 3.10 g of (2-trimethylsilyl)ethyl 3-amino-2-(2-bromoethoxy)-6-[(4, 6-dimethoxypyrimidin-2-yl)oxy] benzoate was obtained by concentration under reduced pressure. This product was used for the next reaction without purification. (Yield: 91.2%)

3.10 g of (2-trimethylsilyl)ethyl 3-amino-2-(2-bromoethoxy)-6-[(4, 6-dimethoxypyrimidin-2-yl)oxy] benzoate and 2.76 g of potassium carbonate in 10 ml of N,N-dimethylformamide were stirred at a temperature of from 60° C. to 80° C. for 3 hours. The mixture was returned to room temperature, then poured into water and extracted with ethyl acetate. The organic layer was washed with water and a saturated sodium chloride aqueous solution and then dried over anhydrous magnesium sulfate. 1.95 g (yield: 75.0%) of the desired compound was obtained by concentration under reduced pressure. Refractive index: 1.5333

EXAMPLE 38

Preparation of 7-[(4,6-dimethoxypyrimidin-2-yl) oxy]-3,4-dihydro-2H-1,4-benzoxadin-8-carboxylic acid (Compound No. 885)

15 ml of 1M tetrahydrofuran solution of tetrabutylammonium fluoride trihydrate was added to 1.65 g of (2-trimethylsilyl)ethyl 7-[(4,6-dimethoxypyrimidin-2-yl) oxy]-3,4-dihydro-2H-1,4-benzoxadin-8-carboxylate obtained in Example 39 in 30 ml of tetrahydrofuran, and the mixture was stirred at room temperature for 3 hours. The mixture was concentrated under reduced pressure, poured into water, adjusted to pH5 with a 20% citric acid aqueous solution and extracted with ethyl acetate. The organic layer was washed with water and a saturated sodium chloride aqueous solution and then dried over anhydrous magnesium sulfate. The residue obtained by concentration under reduced pressure, was crystallized from isopropyl ether to obtain 0.87 g (yield: 68.5%) of the desired compound. mp: 160°–164° C.

The herbicide of the present invention comprises a condensed heterocyclic derivative of the formula (I) as an active ingredient.

For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier which is commonly used for formulations, a surfactant, a dispersant or an adjuvant.

The carrier to be used for such formulations, may, for example, be a solid carrier such as Jeaklite, talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol sulfuric acid ester, an alkylaryl sulfonate, a lignin sulfonate, a polyoxyethylene glycol ether, a polyoxyethylene alkylaryl ether or a polyoxyethylene sorbitol monoalkylate may, for example, be mentioned.

The adjuvant may, for example, be carboxymethyl cellulose, polyethylene glycol or gum arabic.

In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% by weight, preferably from 0.05 to 5% by weight. In a case of an emulsifiable concentrate or a wettable powder, the proportion is selected suitably within a range of from 1 to 50% by weight, preferably from 5 to 20% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In a case of an emulsifiable concentrate or a wettable powder which is used in a liquid state, the dose of the active ingredient is selected suitably within a range of from 1 to 50,000 ppm, preferably from 10 to 10,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, “parts” means “parts by weight”.

FORMULATION EXAMPLE 1 (Wettable powder)

To 10 parts by weight of Compound No. 172, 0.5 part of polyoxyethyleneoctylphenyl ether, 0.5 part of sodium naphthalene sulfonate-formalin condensate, 20 parts of diatomaceous earth and 69 parts of clay were mixed and pulverized to obtain a wettable powder.

FORMULATION EXAMPLE 2 (Wettable powder)

To 10 parts of Compound No. 2, 0.5 part of polyoxyethyleneoctylphenyl ether, 0.5 part of sodium β-naphthalene sulfonate-formalin condensate, 20 parts of diatomaceous earth, 5 parts of fine silica and 64 parts of clay were mixed and pulverized to obtain a wettable powder.

FORMULATION EXAMPLE 3 (Wettable powder)

To 10 parts of Compound No. 24, 0.5 part of polyoxyethyleneoctylphenyl ether, 0.5 part of sodium β-naphthalene sulfonate-formalin condensate, 20 parts of diatomaceous earth, 5 parts of fine silica and 64 parts of calcium carbonate, were mixed and pulverized to obtain a wettable powder.

FORMULATION EXAMPLE 4 (Emulsifiable concentrate)

To 10 parts of Compound No. 9, 80 parts of a mixture comprising equal amounts of xylene and isophorone and 10 parts of a mixture comprising a polyoxyethylene sorbitol alkylate surfactant, a polyoxyethylenealkylaryl polymer and an alkylaryl sulfonate, were added, and the mixture was thoroughly stirred to obtain an emulsifiable concentrate.

FORMULATION EXAMPLE 5 (Granule)

1 part of Compound No. 168, 89 parts of a bulking agent comprising a 1:3 mixture of talc and bentonite, 5 parts of fine silica, 5 parts of a mixture comprising a polyoxyethylene sorbitol alkylate surfactant, a polyoxyethylenealkylaryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

Now, the herbicidal effects of the compounds of the present invention will be described with reference to Test Examples.

TEST EXAMPLE 1 (Test on herbicidal effects by paddy field soil treatment)

In a plastic pot (surface area: 100 $cm^2$) filled with paddy field soil, barnyardgrass (Eo), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 100 g of the active ingredient per 10 ares. The plants were then cultured in a green house, and the evaluation of the herbicidal effects was conducted on the 21st day after the application in accordance with the standards as identified in Table 60. Further, as comparative compounds, compounds identified in Table 61 were formulated and used in the same manner. The results are shown in Tables 62–65.

TABLE 60

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10 and less than 30% |
| 0 | Herbicidal effect or phytotoxicity: 0 to less than 10% |

TABLE 61

| Structural formulae | References |
|---|---|
| Comparative compound A<br>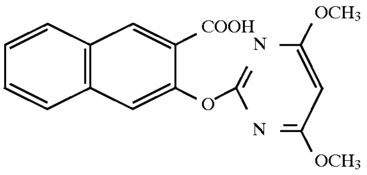 | Japanese Unexamined Patent Publication No. 121973/1990<br>Japanese Unexamined Patent Publication No. 56469/1990 |
| Comparative compound B<br>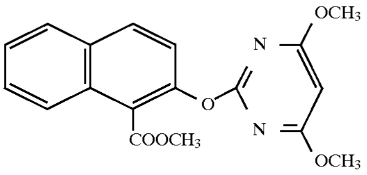 | Japanese Unexamined Patent Publication No. 121973/1990<br>Japanese Unexamined Patent Publication No. 56469/1990 |
| Comparative compound C<br>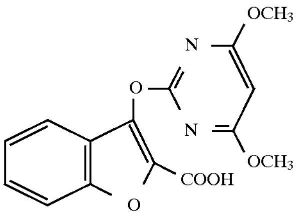 | Japanese Unexamined Patent Publication No. 121973/1990 |
| Comparative compound D<br>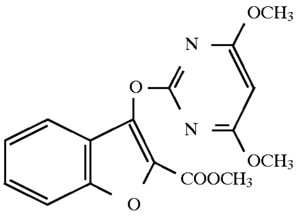 | Japanese Unexamined Patent Publication No. 121973/1990 |

TABLE 61-continued
| Structural formulae | References |
|---|---|
| Comparative compound E | |
| 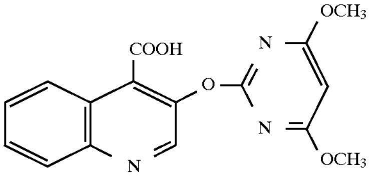 | Japanese Unexamined Patent Publication No. 121973/1990 |
| Comparative compound F | |
| 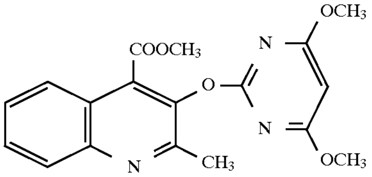 | Japanese Unexamined Patent Publication No. 121973/1990 |
TABLE 62
| Compound | Herbicidal effect | | |
|---|---|---|---|
| No. | Eo | Mo | Sc |
| 1 | 5 | 5 | 5 |
| 2 | 5 | 5 | 5 |
| 4 | 5 | 5 | 5 |
| 8 | 5 | 5 | 5 |
| 9 | 5 | 5 | 5 |
| 10 | 5 | 5 | 5 |
| 11 | 5 | 5 | 5 |
| 12 | 5 | 5 | 5 |
| 13 | 5 | 5 | 5 |
| 16 | 5 | 5 | 5 |
| 24 | 5 | 5 | 5 |
| 26 | 5 | 5 | 5 |
| 34 | 5 | 5 | 5 |
| 35 | 5 | 5 | 5 |
| 36 | 5 | 5 | 5 |
| 38 | 5 | 5 | 5 |
| 40 | 5 | 5 | 5 |
| 42 | 5 | 5 | 5 |
| 45 | 5 | 5 | 5 |
| 48 | 5 | 5 | 5 |
| 50 | 5 | 5 | 5 |
| 59 | 5 | 5 | 5 |
| 61 | 5 | 5 | 5 |
| 62 | 5 | 5 | 5 |
| 63 | 5 | 5 | 5 |
| 71 | 5 | 5 | 5 |
| 88 | 5 | 5 | 5 |
| 105 | 5 | 5 | 5 |
| 165 | 5 | 5 | 5 |
| 167 | 5 | 5 | 5 |
| 169 | 5 | 5 | 5 |
| 171 | 5 | 5 | 5 |
| 172 | 5 | 5 | 5 |
| 178 | 5 | 5 | 5 |
TABLE 63
| Compound | Herbicidal effect | | |
|---|---|---|---|
| No. | Eo | Mo | Sc |
| 182 | 5 | 5 | 5 |
| 262 | 5 | 5 | 5 |
| 286 | 5 | 5 | 5 |
| 301 | 5 | 5 | 5 |
| 365 | 5 | 5 | 5 |
| 405 | 5 | 5 | 5 |
| 445 | 5 | 5 | 5 |
| 505 | 5 | 5 | 5 |
| 506 | 5 | 5 | 5 |
| 507 | 5 | 5 | 5 |
| 508 | 5 | 5 | 5 |
| 509 | 5 | 5 | 5 |
| 511 | 5 | 5 | 5 |
| 512 | 5 | 5 | 5 |
| 515 | 5 | 5 | 4 |
| 516 | 5 | 5 | 4 |
| 519 | 5 | 5 | 5 |
| 520 | 5 | 5 | 5 |
| 522 | 5 | 5 | 5 |
| 523 | 5 | 5 | 5 |
| 524 | 5 | 5 | 5 |
| 525 | 5 | 5 | 5 |
| 526 | 5 | 5 | 5 |
| 527 | 5 | 5 | 5 |
| 528 | 5 | 5 | 5 |
| 529 | 5 | 5 | 5 |
| 530 | 5 | 5 | 5 |
| 531 | 5 | 5 | 5 |
| 533 | 5 | 5 | 5 |
| 535 | 5 | 5 | 5 |
| 539 | 5 | 5 | 5 |
| 541 | 5 | 5 | 5 |
| 542 | 5 | 5 | 5 |
| 543 | 5 | 5 | 5 |
TABLE 64
| Compound | Herbicidal effect | | |
|---|---|---|---|
| No. | Eo | Mo | Sc |
| 534 | 5 | 5 | 5 |
| 544 | 5 | 5 | 5 |
| 545 | 5 | 5 | 5 |
| 546 | 5 | 5 | 5 |
| 547 | 5 | 5 | 5 |
| 548 | 5 | 5 | 5 |
| 549 | 5 | 5 | 5 |
| 550 | 5 | 5 | 5 |
| 551 | 5 | 5 | 5 |
| 553 | 5 | 5 | 5 |
| 554 | 5 | 5 | 5 |
| 555 | 5 | 5 | 5 |
| 556 | 5 | 5 | 5 |
| 558 | 5 | 5 | 5 |
| 562 | 5 | 5 | 5 |
| 563 | 5 | 5 | 5 |
| 564 | 5 | 5 | 5 |
| 567 | 5 | 5 | 5 |
| 568 | 5 | 5 | 5 |
| 572 | 5 | 5 | 5 |
| 573 | 5 | 5 | 5 |
| 575 | 5 | 5 | 5 |
| 578 | 5 | 5 | 5 |
| 584 | 5 | 5 | 5 |
| 588 | 5 | 5 | 5 |
| 589 | 5 | 5 | 5 |
| 591 | 5 | 5 | 5 |
| 593 | 5 | 5 | 5 |
| 594 | 5 | 5 | 5 |
| 595 | 5 | 5 | 5 |
| 596 | 5 | 5 | 5 |

TABLE 64-continued

| Compound No. | Herbicidal effect Eo | Mo | Sc |
|---|---|---|---|
| 597 | 5 | 5 | 5 |
| 598 | 5 | 5 | 5 |
| 599 | 5 | 5 | 5 |

TABLE 65

| Compound No. | Herbicidal effect Eo | Mo | Sc |
|---|---|---|---|
| 600 | 5 | 5 | 5 |
| 611 | 5 | 5 | 5 |
| 613 | 5 | 5 | 5 |
| 614 | 5 | 5 | 5 |
| 615 | 5 | 5 | 5 |
| 616 | 5 | 5 | 5 |
| 619 | 5 | 5 | 5 |
| 622 | 5 | 5 | 5 |
| 626 | 5 | 5 | 5 |
| 628 | 5 | 5 | 4 |
| 665 | 5 | 5 | 5 |
| 671 | 5 | 5 | 5 |
| 681 | 5 | 5 | 5 |
| 693 | 5 | 5 | 5 |
| 770 | 3 | 5 | 5 |
| 772 | 5 | 5 | 5 |
| 787 | 5 | 5 | 5 |
| 789 | 5 | 5 | 5 |
| 797 | 5 | 5 | 5 |
| 813 | 5 | 5 | 5 |
| 815 | 5 | 5 | 5 |
| 831 | 5 | 5 | 5 |
| 834 | 5 | 3 | 5 |
| 929 | 5 | 5 | 5 |
| 931 | 5 | 5 | 5 |
| 933 | 5 | 5 | 5 |
| 952 | 5 | 5 | 5 |
| 955 | 5 | 5 | 5 |
| Comparative compound A | 0 | 0 | 0 |
| Comparative compound B | 4 | 1 | 2 |
| Comparative compound E | 0 | 0 | 0 |
| Comparative compound F | 0 | 0 | 0 |

TEST EXAMPLE 2 (Test on herbicidal effects by upland field soil treatment)

In a plastic pot.(surface area: 120 $cm^2$) filled with upland field soil, barnyardgrass (Ec), pale smartweed (Po), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 l/10 ares so as to apply 100 g of the active ingredient per 10 ares. The plants were then cultured in a green house, and the evaluation of the herbicidal effects was conducted on the 21st day after the application in accordance with the standards as identified in Table 60. Further, as comparative compounds, compounds identified in Table 61 were formulated and used in the same manner. The results are shown in Tables 66–69.

TABLE 66

| Compound No. | Herbicidal effect Ec | Po | Am | Ch | Ci |
|---|---|---|---|---|---|
| 2 | 5 | 5 | 5 | 5 | 5 |
| 4 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 16 | 5 | 5 | 5 | 5 | 5 |
| 24 | 5 | 5 | 5 | 5 | 5 |
| 26 | 5 | 5 | 5 | 5 | 5 |
| 30 | 5 | 5 | 5 | 5 | 5 |
| 34 | 5 | 5 | 5 | 5 | 5 |
| 35 | 5 | 5 | 5 | 5 | 5 |
| 36 | 5 | 5 | 5 | 5 | 5 |
| 38 | 5 | 5 | 5 | 5 | 5 |
| 40 | 5 | 5 | 5 | 5 | 5 |
| 42 | 5 | 5 | 5 | 5 | 5 |
| 48 | 5 | 5 | 5 | 5 | 5 |
| 50 | 5 | 5 | 5 | 5 | 5 |
| 59 | 5 | 5 | 5 | 5 | 5 |
| 61 | 5 | 5 | 5 | 5 | 5 |
| 62 | 5 | 5 | 5 | 5 | 5 |
| 88 | 5 | 5 | 5 | 5 | 5 |
| 105 | 5 | 5 | 5 | 5 | 5 |
| 109 | 5 | 5 | 5 | 5 | 5 |
| 165 | 5 | 5 | 5 | 5 | 5 |
| 167 | 5 | 5 | 5 | 5 | 5 |
| 169 | 5 | 5 | 5 | 5 | 5 |
| 171 | 5 | 5 | 5 | 5 | 5 |
| 172 | 5 | 5 | 5 | 5 | 5 |
| 178 | 5 | 5 | 5 | 5 | 5 |
| 204 | 5 | 5 | 5 | 5 | 5 |
| 262 | 5 | 4 | 5 | 5 | 5 |

TABLE 67

| Compound No. | Herbicidal effect Ec | Po | Am | Ch | Ci |
|---|---|---|---|---|---|
| 286 | 5 | 5 | 5 | 5 | 5 |
| 301 | 4 | 5 | 5 | 5 | 5 |
| 386 | 5 | 5 | 5 | 5 | 5 |
| 506 | 5 | 5 | 5 | 5 | 5 |
| 507 | 4 | 5 | 5 | 5 | 5 |
| 508 | 5 | 5 | 5 | 5 | 5 |
| 509 | 4 | 5 | 5 | 5 | 4 |
| 511 | 5 | 5 | 5 | 5 | 5 |
| 512 | 5 | 5 | 5 | 5 | 5 |
| 519 | 5 | 5 | 5 | 5 | 5 |
| 520 | 5 | 5 | 5 | 5 | 5 |
| 522 | 5 | 5 | 5 | 5 | 5 |
| 523 | 5 | 5 | 5 | 5 | 5 |
| 524 | 5 | 5 | 5 | 5 | 5 |
| 525 | 5 | 5 | 5 | 5 | 5 |
| 526 | 5 | 5 | 5 | 5 | 5 |
| 528 | 5 | 5 | 5 | 5 | 5 |
| 529 | 5 | 5 | 5 | 5 | 5 |
| 530 | 5 | 5 | 5 | 5 | 5 |
| 531 | 5 | 5 | 5 | 5 | 5 |
| 533 | 5 | 5 | 5 | 5 | 5 |
| 537 | 4 | 5 | 5 | 5 | 5 |
| 539 | 5 | 5 | 5 | 5 | 5 |
| 541 | 5 | 5 | 5 | 5 | 5 |
| 543 | 5 | 5 | 5 | 5 | 5 |
| 544 | 5 | 5 | 5 | 5 | 5 |
| 546 | 5 | 5 | 5 | 5 | 5 |
| 547 | 5 | 5 | 5 | 5 | 5 |
| 548 | 5 | 5 | 5 | 5 | 5 |
| 549 | 5 | 5 | 5 | 5 | 5 |
| 550 | 5 | 5 | 5 | 5 | 5 |

TABLE 67-continued

| Compound No. | Herbicidal effect Ec | Po | Am | Ch | Ci |
|---|---|---|---|---|---|
| 551 | 5 | 5 | 5 | 5 | 5 |
| 553 | 5 | 5 | 5 | 5 | 5 |
| 554 | 5 | 5 | 5 | 5 | 5 |

TABLE 68

| Compound No. | Herbicidal effect Ec | Po | Am | Ch | Ci |
|---|---|---|---|---|---|
| 555 | 5 | 5 | 5 | 5 | 5 |
| 556 | 4 | 5 | 5 | 5 | 5 |
| 558 | 4 | 5 | 5 | 5 | 5 |
| 562 | 5 | 5 | 5 | 5 | 5 |
| 563 | 5 | 5 | 5 | 5 | 5 |
| 564 | 4 | 5 | 5 | 5 | 5 |
| 567 | 4 | 5 | 5 | 5 | 5 |
| 568 | 5 | 5 | 5 | 5 | 5 |
| 573 | 5 | 5 | 5 | 5 | 5 |
| 575 | 5 | 5 | 5 | 5 | 5 |
| 578 | 5 | 5 | 5 | 5 | 5 |
| 584 | 5 | 5 | 5 | 5 | 5 |
| 588 | 5 | 5 | 5 | 5 | 5 |
| 589 | 5 | 5 | 5 | 5 | 5 |
| 591 | 5 | 5 | 5 | 5 | 5 |
| 594 | 5 | 5 | 5 | 5 | 5 |
| 595 | 5 | 5 | 5 | 5 | 5 |
| 596 | 5 | 5 | 5 | 5 | 5 |
| 597 | 5 | 5 | 5 | 5 | 5 |
| 598 | 5 | 5 | 5 | 5 | 5 |
| 599 | 5 | 5 | 5 | 5 | 5 |
| 600 | 4 | 5 | 5 | 5 | 5 |
| 611 | 5 | 5 | 5 | 5 | 5 |
| 613 | 5 | 5 | 5 | 5 | 5 |
| 614 | 5 | 5 | 5 | 5 | 5 |
| 615 | 4 | 5 | 5 | 5 | 5 |
| 616 | 5 | 5 | 5 | 5 | 5 |
| 626 | 5 | 5 | 5 | 5 | 5 |
| 627 | 4 | 5 | 5 | 5 | 5 |
| 628 | 5 | 5 | 5 | 5 | 5 |
| 665 | 5 | 5 | 5 | 5 | 5 |
| 667 | 3 | 5 | 5 | 5 | 5 |
| 681 | 5 | 5 | 5 | 5 | 5 |
| 693 | 3 | 5 | 5 | 5 | 5 |

TABLE 69

| Compound No. | Herbicidal effect Ec | Po | Am | Ch | Ci |
|---|---|---|---|---|---|
| 770 | 3 | 5 | 5 | 5 | 5 |
| 772 | 5 | 5 | 5 | 5 | 5 |
| 787 | 5 | 5 | 5 | 5 | 5 |
| 789 | 5 | 5 | 5 | 5 | 5 |
| 797 | 3 | 5 | 5 | 5 | 5 |
| 815 | 5 | 5 | 5 | 5 | 5 |
| 831 | 3 | 5 | 5 | 5 | 5 |
| 834 | 3 | 5 | 5 | 5 | 5 |
| 852 | 2 | 5 | 5 | 5 | 5 |
| 883 | 3 | 5 | 5 | 3 | 5 |
| 929 | 4 | 5 | 4 | 4 | 5 |
| 931 | 5 | 5 | 5 | 4 | 5 |
| 933 | 5 | 5 | 5 | 5 | 5 |
| 952 | 5 | 4 | 5 | 5 | 5 |
| 984 | 4 | 5 | 5 | 5 | 5 |
| Comparative compound A | 0 | 0 | 0 | 0 | 0 |
| Comparative compound B | 0 | 0 | 2 | 3 | 0 |

TABLE 69-continued

| Compound No. | Herbicidal effect Ec | Po | Am | Ch | Ci |
|---|---|---|---|---|---|
| Comparative compound C | 1 | 2 | 5 | 4 | 2 |
| Comparative compound D | 0 | 2 | 4 | 4 | 1 |
| Comparative compound E | 0 | 0 | 2 | 0 | 1 |
| Comparative compound F | 0 | 0 | 0 | 0 | 0 |

TEST EXAMPLE 3 (Test on herbicidal effects by upland field foliage treatment)

In a plastic pot (surface area: 120 $cm^2$) filled with upland field soil, barnyardgrass (Ec), pale smartweed (Po), slender amaranth (Am), common lambsquarters (Ch) and rice flat-sedge (Ci) were sown and covered with soil and were cultured in a green house for 2 weeks. A wettable powder prepared in accordance with Formulation Example 1 was diluted with water and applied onto the entire foliages of the plants from above by a small-sized sprayer in an amount of 100 l/10 ares so as to apply 100 g of the active ingredient per 10 ares. The plants were then cultured in the green house, and the evaluation of the herbicidal effects was conducted on the 14th day after the treatment in accordance with the standards as identified in Table 60. Further, as comparative compounds, compounds identified in Table 61 were formulated and used in the same manner. The results are shown in Tables 70–74.

TABLE 70

| Compound No. | Herbicidal effect Ec | Po | Am | Ch | Ci |
|---|---|---|---|---|---|
| 1 | 5 | 5 | 5 | 5 | 5 |
| 2 | 5 | 5 | 5 | 5 | 5 |
| 4 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 16 | 5 | 5 | 5 | 5 | 5 |
| 24 | 5 | 5 | 5 | 5 | 5 |
| 26 | 5 | 5 | 5 | 5 | 5 |
| 30 | 5 | 5 | 5 | 5 | 5 |
| 34 | 5 | 5 | 5 | 5 | 5 |
| 35 | 5 | 5 | 5 | 5 | 5 |
| 36 | 5 | 5 | 5 | 5 | 5 |
| 38 | 5 | 5 | 5 | 5 | 5 |
| 40 | 5 | 5 | 5 | 5 | 5 |
| 42 | 5 | 5 | 5 | 5 | 5 |
| 48 | 5 | 5 | 5 | 5 | 5 |
| 59 | 5 | 5 | 5 | 5 | 5 |
| 61 | 5 | 5 | 5 | 5 | 5 |
| 62 | 5 | 5 | 5 | 5 | 5 |
| 71 | 5 | 5 | 5 | 5 | 5 |
| 88 | 5 | 5 | 5 | 5 | 5 |
| 105 | 5 | 5 | 5 | 5 | 5 |
| 159 | 3 | 5 | 5 | 4 | 5 |
| 162 | 5 | 5 | 5 | 5 | 5 |
| 165 | 5 | 5 | 5 | 5 | 5 |
| 167 | 5 | 5 | 5 | 5 | 5 |
| 169 | 5 | 5 | 5 | 5 | 5 |
| 171 | 5 | 5 | 5 | 5 | 5 |
| 178 | 5 | 5 | 5 | 5 | 5 |
| 204 | 5 | 5 | 5 | 5 | 5 |

TABLE 71

| Compound | Herbicidal effect | | | | |
|---|---|---|---|---|---|
| No. | Ec | Po | Am | Ch | Ci |
| 262 | 5 | 5 | 5 | 5 | 5 |
| 286 | 5 | 5 | 5 | 5 | 5 |
| 301 | 5 | 5 | 5 | 5 | 3 |
| 344 | 3 | 5 | 5 | 5 | 4 |
| 365 | 3 | 5 | 5 | 5 | 5 |
| 367 | 4 | 5 | 5 | 4 | 5 |
| 445 | 5 | 5 | 5 | 5 | 5 |
| 488 | 5 | 5 | 5 | 5 | 5 |
| 505 | 5 | 5 | 5 | 5 | 4 |
| 506 | 5 | 5 | 5 | 5 | 5 |
| 507 | 5 | 5 | 5 | 5 | 5 |
| 508 | 5 | 5 | 5 | 5 | 5 |
| 509 | 5 | 5 | 5 | 5 | 5 |
| 511 | 5 | 5 | 5 | 5 | 5 |
| 512 | 5 | 5 | 5 | 5 | 5 |
| 519 | 5 | 5 | 5 | 5 | 5 |
| 520 | 5 | 5 | 5 | 5 | 5 |
| 523 | 5 | 5 | 5 | 5 | 5 |
| 524 | 5 | 5 | 5 | 5 | 5 |
| 525 | 3 | 5 | 5 | 5 | 3 |
| 526 | 5 | 5 | 5 | 5 | 5 |
| 528 | 5 | 5 | 5 | 5 | 5 |
| 529 | 5 | 5 | 5 | 5 | 5 |
| 530 | 5 | 5 | 5 | 5 | 5 |
| 531 | 5 | 5 | 5 | 5 | 5 |
| 533 | 5 | 5 | 5 | 5 | 5 |
| 534 | 4 | 5 | 5 | 4 | 5 |
| 539 | 5 | 5 | 5 | 5 | 5 |
| 540 | 3 | 5 | 5 | 5 | 3 |
| 541 | 5 | 5 | 5 | 5 | 5 |
| 543 | 5 | 5 | 5 | 5 | 5 |
| 544 | 5 | 5 | 5 | 5 | 5 |
| 546 | 5 | 5 | 5 | 5 | 5 |
| 547 | 5 | 5 | 5 | 5 | 5 |

TABLE 72

| Compound | Herbicidal effect | | | | |
|---|---|---|---|---|---|
| No. | Ec | Po | Am | Ch | Ci |
| 548 | 5 | 5 | 5 | 5 | 5 |
| 549 | 5 | 5 | 5 | 5 | 5 |
| 550 | 5 | 5 | 5 | 5 | 5 |
| 551 | 5 | 5 | 5 | 5 | 5 |
| 553 | 5 | 5 | 5 | 5 | 5 |
| 554 | 5 | 5 | 5 | 4 | 5 |
| 555 | 5 | 5 | 5 | 3 | 5 |
| 556 | 4 | 5 | 5 | 4 | 5 |
| 558 | 5 | 5 | 5 | 5 | 5 |
| 562 | 5 | 5 | 5 | 5 | 5 |
| 563 | 5 | 5 | 5 | 5 | 5 |
| 564 | 5 | 5 | 5 | 5 | 5 |
| 567 | 5 | 5 | 5 | 5 | 5 |
| 568 | 5 | 5 | 5 | 5 | 5 |
| 573 | 5 | 5 | 5 | 5 | 5 |
| 575 | 5 | 5 | 5 | 5 | 5 |
| 578 | 5 | 5 | 5 | 5 | 5 |
| 584 | 5 | 5 | 5 | 5 | 5 |
| 588 | 5 | 5 | 5 | 5 | 5 |
| 589 | 5 | 5 | 5 | 5 | 5 |
| 591 | 5 | 5 | 5 | 5 | 5 |
| 594 | 5 | 5 | 5 | 5 | 5 |
| 595 | 5 | 5 | 5 | 5 | 5 |
| 596 | 5 | 5 | 5 | 5 | 5 |
| 597 | 5 | 5 | 5 | 5 | 5 |
| 598 | 5 | 5 | 5 | 5 | 5 |
| 599 | 5 | 5 | 5 | 5 | 5 |
| 600 | 5 | 5 | 5 | 5 | 5 |
| 611 | 5 | 5 | 5 | 5 | 5 |
| 613 | 5 | 5 | 5 | 5 | 5 |
| 614 | 5 | 5 | 5 | 5 | 5 |

TABLE 72-continued

| Compound | Herbicidal effect | | | | |
|---|---|---|---|---|---|
| No. | Ec | Po | Am | Ch | Ci |
| 615 | 5 | 5 | 5 | 5 | 5 |
| 616 | 5 | 5 | 5 | 5 | 5 |
| 619 | 4 | 5 | 5 | 5 | 5 |

TABLE 73

| Compound | Herbicidal effect | | | | |
|---|---|---|---|---|---|
| No. | Ec | Po | Am | Ch | Ci |
| 622 | 4 | 5 | 5 | 5 | 4 |
| 627 | 5 | 5 | 5 | 5 | 5 |
| 628 | 5 | 5 | 5 | 5 | 4 |
| 665 | 5 | 5 | 5 | 5 | 5 |
| 667 | 5 | 5 | 5 | 5 | 5 |
| 671 | 5 | 5 | 5 | 5 | 5 |
| 681 | 5 | 5 | 5 | 5 | 3 |
| 691 | 5 | 5 | 5 | 5 | 5 |
| 693 | 5 | 5 | 5 | 5 | 5 |
| 714 | 5 | 5 | 5 | 5 | 5 |
| 738 | 5 | 3 | 5 | 4 | 5 |
| 740 | 5 | 5 | 5 | 5 | 5 |
| 760 | 3 | 5 | 5 | 4 | 5 |
| 770 | 5 | 5 | 5 | 5 | 5 |
| 772 | 5 | 5 | 5 | 5 | 5 |
| 787 | 5 | 5 | 5 | 5 | 5 |
| 789 | 5 | 5 | 5 | 5 | 5 |
| 797 | 5 | 5 | 5 | 5 | 5 |
| 813 | 5 | 5 | 5 | 5 | 5 |
| 815 | 5 | 5 | 5 | 5 | 5 |
| 827 | 4 | 5 | 5 | 5 | 3 |
| 829 | 5 | 5 | 5 | 5 | 4 |
| 831 | 5 | 5 | 5 | 5 | 5 |
| 852 | 3 | 5 | 5 | 4 | 3 |
| 854 | 5 | 5 | 5 | 3 | 4 |
| 885 | 5 | 5 | 5 | 5 | 5 |
| 887 | 4 | 5 | 5 | 5 | 5 |
| 891 | 5 | 5 | 5 | 5 | 5 |
| 892 | 5 | 5 | 5 | 5 | 5 |
| 897 | 5 | 5 | 5 | 3 | 5 |
| 929 | 5 | 5 | 5 | 5 | 5 |
| 931 | 5 | 5 | 5 | 5 | 5 |
| 933 | 5 | 5 | 5 | 5 | 5 |
| 952 | 5 | 5 | 5 | 5 | 5 |

TABLE 74

| Compound | Herbicidal effect | | | | |
|---|---|---|---|---|---|
| No. | Ec | Po | Am | Ch | Ci |
| 955 | 5 | 5 | 5 | 5 | 5 |
| 683 | 5 | 5 | 5 | 5 | 5 |
| 984 | 5 | 5 | 5 | 5 | 5 |
| 958 | 5 | 5 | 5 | 5 | 5 |
| Comparative compound A | 0 | 0 | 0 | 0 | 0 |
| Comparative compound B | 0 | 2 | 3 | 3 | 0 |
| Comparative compound C | 2 | 1 | 4 | 5 | 2 |
| Comparative compound D | 0 | 1 | 2 | 4 | 0 |
| Comparative compound E | 0 | 4 | 3 | 0 | 1 |
| Comparative compound F | 0 | 0 | 0 | 0 | 0 |

TEST EXAMPLE 4 (Test on crop plant selectivity by paddy field soil treatment)

In a 1/10,000a plastic pot, paddy field soil was filled, irrigated, paddled and leveled. Then, barnyardgrass (Eo), monochoria (Mo) and bulrush (Sc) were sown at a depth of 0.5 cm. Further, two seedlings of rice (Or) of 2.5 leaf stage was transplanted at a transplantation depth of 2 cm. Then, the pot was flooded to a water depth of 3 cm. Next day, a prescribed amount of the active ingredient ($g^{ai}$/10a) of a wettable powder prepared in accordance with Formulation Example 1 was diluted with water and applied dropwise to the water surface. The plants were then cultured in a green house, and the evaluation of the herbicidal effects and phytotoxicity was conducted on the 28th day after the application in accordance with the standards as identified in Table 60. Further, as comparative compounds, compounds identified in Table 61 were formulated and used in the same manner. The results are shown in Tables 75 to 77.

TABLE 75

| Compound | Dose | Herbicidal effect | | | Phyto-toxicity |
|---|---|---|---|---|---|
| No. | ($g^{ai}$/10a) | Eo | Mo | Sc | Or |
| 1 | 25 | 4 | 4 | 3 | 0 |
| 2 | 1.6 | 5 | 5 | 4 | 0 |
| 4 | 6.3 | 5 | 5 | 3 | 1 |
| 8 | 6.3 | 5 | 5 | 5 | 0 |
| 9 | 6.3 | 5 | 5 | 5 | 0 |
| 10 | 6.3 | 5 | 5 | 5 | 0 |
| 11 | 6.3 | 5 | 5 | 5 | 1 |
| 12 | 1.6 | 5 | 5 | 3 | 0 |
| 34 | 6.3 | 5 | 5 | 5 | 0 |
| 35 | 6.3 | 5 | 5 | 5 | 1 |
| 36 | 1.6 | 5 | 5 | 3 | 0 |
| 59 | 25 | 5 | 5 | 3 | 0 |
| 105 | 25 | 5 | 5 | 3 | 0 |
| 165 | 6.3 | 5 | 5 | 5 | 0 |
| 167 | 25 | 5 | 5 | 5 | 0 |
| 169 | 25 | 5 | 5 | 5 | 0 |
| 171 | 6.3 | 5 | 5 | 5 | 0 |
| 172 | 6.3 | 5 | 5 | 5 | 0 |
| 178 | 25 | 4 | 5 | 5 | 0 |
| 262 | 6.3 | 4 | 5 | 3 | 0 |
| 504 | 25 | 5 | 5 | 3 | 0 |
| 509 | 6.3 | 5 | 5 | 5 | 0 |
| 511 | 1.6 | 5 | 5 | 4 | 0 |
| 522 | 6.3 | 5 | 5 | 5 | 0 |
| 523 | 25 | 5 | 5 | 5 | 1 |
| 524 | 25 | 5 | 5 | 5 | 0 |
| 525 | 6.3 | 5 | 5 | 5 | 0 |
| 526 | 1.6 | 5 | 5 | 4 | 0 |
| 528 | 1.6 | 5 | 5 | 5 | 0 |
| 529 | 1.6 | 5 | 5 | 5 | 0 |
| 530 | 6.3 | 5 | 5 | 5 | 0 |
| 531 | 1.6 | 5 | 5 | 4 | 1 |
| 533 | 6.3 | 5 | 5 | 5 | 0 |

TABLE 76

| Compound | Dose | Herbicidal effect | | | Phyto-toxicity |
|---|---|---|---|---|---|
| No. | ($g^{ai}$/10a) | Eo | Mo | Sc | Or |
| 534 | 6.3 | 5 | 5 | 5 | 0 |
| 541 | 6.3 | 5 | 5 | 3 | 0 |
| 543 | 6.3 | 5 | 5 | 3 | 0 |
| 544 | 6.3 | 5 | 5 | 5 | 0 |
| 545 | 6.3 | 3 | 5 | 3 | 0 |
| 546 | 6.3 | 5 | 5 | 3 | 0 |
| 547 | 6.3 | 4 | 5 | 4 | 0 |
| 548 | 6.3 | 4 | 4 | 3 | 0 |
| 549 | 6.3 | 5 | 5 | 4 | 0 |
| 550 | 6.3 | 5 | 5 | 3 | 0 |

TABLE 76-continued

| Compound | Dose | Herbicidal effect | | | Phyto-toxicity |
|---|---|---|---|---|---|
| No. | ($g^{ai}$/10a) | Eo | Mo | Sc | Or |
| 551 | 6.3 | 5 | 5 | 5 | 0 |
| 553 | 6.3 | 5 | 5 | 5 | 1 |
| 554 | 6.3 | 5 | 5 | 5 | 0 |
| 555 | 25 | 5 | 5 | 5 | 0 |
| 556 | 25 | 5 | 5 | 5 | 0 |
| 562 | 6.3 | 5 | 5 | 5 | 1 |
| 563 | 25 | 5 | 5 | 5 | 0 |
| 568 | 25 | 3 | 5 | 5 | 0 |
| 572 | 25 | 4 | 5 | 4 | 0 |
| 573 | 25 | 5 | 5 | 5 | 0 |
| 578 | 25 | 5 | 5 | 5 | 1 |
| 600 | 25 | 4 | 5 | 3 | 1 |
| 611 | 6.3 | 5 | 5 | 3 | 1 |
| 613 | 6.3 | 5 | 5 | 4 | 0 |
| 614 | 6.3 | 4 | 5 | 3 | 0 |
| 616 | 6.3 | 5 | 5 | 5 | 0 |
| 623 | 6.3 | 4 | 5 | 5 | 0 |
| 681 | 25 | 5 | 5 | 4 | 1 |
| 797 | 6.3 | 4 | 5 | 3 | 0 |
| 831 | 6.3 | 5 | 5 | 5 | 0 |
| 929 | 6.3 | 5 | 5 | 5 | 0 |
| 931 | 25 | 5 | 5 | 5 | 0 |
| 933 | 25 | 4 | 5 | 5 | 1 |

TABLE 77

| Compound | Dose | Herbicidal effect | | | Phyto-toxicity |
|---|---|---|---|---|---|
| No. | ($g^{ai}$/10a) | Eo | Mo | Sc | Or |
| 955 | 25 | 4 | 5 | 5 | 1 |
| Comparative compound A | 25 | 0 | 0 | 0 | 0 |
| Comparative compound B | 25 | 2 | 0 | 0 | 0 |
| Comparative compound C | 25 | 3 | 4 | 3 | 4 |
| Comparative compound D | 25 | 2 | 3 | 1 | 3 |
| Comparative compound E | 100 | 0 | 0 | 0 | 0 |
| Comparative compound F | 100 | 0 | 0 | 0 | 0 |

TEST EXAMPLE 5 (Test on crop plant selectivity by upland field soil treatment)

In a plastic pot (surface area: 600 $cm^2$) filled with upland field soil, wheat (Tr), barnyardgrass (Ec),green foxtail (Se), Johnsongrass (So), Alopecurus myosuroides (Al), pale smartweed (Po), slender amaranth (Am) and common lambsquarters (Ch) were sown and covered with soil. Next day, a prescribed amount of the active ingredient ($g^{ai}$/10a) of a wettable powder prepared in accordance with Formulation Example 1 was diluted with water and applied uniformly to the soil surface by a small-sized sprayer in an amount of 100 l per 10 ares. The plants were then cultured in a green house, and the evaluation of the herbicidal effects was conducted on the 21st day after the application in accordance with the standards as identified in Table 60. Further, as comparative compounds, compounds identified in Table 61 were formulated and used in the same manner. The results are shown in Tables 78 to 79.

TABLE 78

| Compound No. | Dose ($g^{ai}$/10a) | Herbicidal effect Ec | Se | So | Al | Po | Am | Ch | Phyto-toxicity Tr |
|---|---|---|---|---|---|---|---|---|---|
| 2 | 25 | 5 | 5 | 5 | 5 | 5 | 5 | 5 | 1 |
| 4 | 25 | 5 | 5 | 5 | 5 | 5 | 5 | 5 | 1 |
| 9 | 25 | 5 | 5 | 5 | 5 | 5 | 5 | 5 | 1 |
| 10 | 25 | 5 | 5 | 5 | 5 | 5 | 5 | 5 | 1 |
| 11 | 25 | 5 | 4 | 5 | 5 | 5 | 5 | 5 | 0 |
| 12 | 25 | 5 | 5 | 5 | 5 | 5 | 5 | 5 | 1 |
| 13 | 25 | 4 | 3 | 5 | 5 | 5 | 5 | 5 | 0 |
| 24 | 25 | 5 | 4 | 5 | 5 | 5 | 5 | 5 | 0 |
| 26 | 25 | 5 | 4 | 5 | 5 | 5 | 5 | 5 | 0 |
| 40 | 25 | 4 | 5 | 5 | 3 | 5 | 5 | 5 | 0 |
| 42 | 25 | 3 | 1 | 4 | 3 | 5 | 5 | 5 | 0 |
| 61 | 25 | 5 | 5 | 5 | 5 | 5 | 5 | 3 | 0 |
| 62 | 6.3 | 5 | 4 | 5 | 5 | 5 | 5 | 3 | 0 |
| 507 | 25 | 5 | 5 | 5 | 5 | 5 | 5 | 5 | 0 |
| 511 | 25 | 5 | 3 | 5 | 5 | 5 | 5 | 3 | 0 |
| 512 | 6.3 | 5 | 3 | 5 | 5 | 5 | 5 | 5 | 0 |
| 523 | 25 | 5 | 3 | 4 | 4 | 5 | 5 | 5 | 1 |
| 525 | 6.3 | 5 | 3 | 5 | 5 | 5 | 5 | 5 | 0 |
| 526 | 6.3 | 5 | 5 | 5 | 5 | 5 | 5 | 5 | 1 |
| 527 | 6.3 | 5 | 5 | 5 | 5 | 5 | 5 | 5 | 0 |
| 529 | 25 | 5 | 5 | 5 | 5 | 5 | 5 | 5 | 0 |
| 531 | 25 | 5 | 5 | 5 | 5 | 5 | 5 | 5 | 0 |
| 536 | 6.3 | 5 | 3 | 5 | 5 | 5 | 5 | 5 | 0 |

TABLE 79

| Compound No. | Dose ($g^{ai}$/10a) | Herbicidal effect Ec | Se | So | Al | Po | Am | Ch | Phyto-toxicity Tr |
|---|---|---|---|---|---|---|---|---|---|
| 553 | 25 | 5 | 5 | 5 | 5 | 5 | 5 | 5 | 0 |
| 554 | 25 | 5 | 5 | 5 | 5 | 5 | 5 | 5 | 0 |
| 563 | 6.3 | 5 | 4 | 5 | 5 | 5 | 5 | 5 | 0 |
| 591 | 6.3 | 3 | 4 | 5 | 5 | 5 | 5 | 5 | 0 |
| 665 | 6.3 | 3 | 3 | 4 | 4 | 5 | 5 | 5 | 0 |
| 787 | 6.3 | 3 | 5 | 5 | 5 | 5 | 5 | 5 | 3 |
| 789 | 6.3 | 2 | 3 | 5 | 5 | 5 | 5 | 5 | 2 |
| Comparative compound A | 25 | 0 | 0 | 0 | 0 | 0 | 0 | 0 | 0 |
| Comparative compound B | 25 | 0 | 0 | 0 | 0 | 0 | 1 | 1 | 0 |
| Comparative compound C | 100 | 1 | 0 | 1 | 1 | 2 | 5 | 4 | 3 |
| Comparative compound D | 400 | 2 | 1 | 3 | 2 | 2 | 5 | 5 | 4 |
| Comparative compound E | 25 | 0 | 0 | 0 | 0 | 0 | 0 | 0 | 0 |
| Comparative compound F | 25 | 0 | 0 | 0 | 0 | 0 | 0 | 0 | 0 |

TEST EXAMPLE 6 (Test on crop plant selectivity by upland field foliage treatment)

In a plastic pot (surface area: 600 $cm^2$) filled with upland field soil, rice (Or), wheat (Tr), barnyardgrass (Ec), Johnsongrass (So), Alopecurus myosucroides (Al), pale smartweed (Po), slender amaranth (Am) and common lambsquarters (Ch) were sown and cultured in a green house for 2 weeks. Then, a prescribed amount of the active ingredient ($g^{ai}$/10a) of a wettable powder prepared in accordance with Formulation Example 1 was diluted with water and applied onto the entire foliages of the plants from above by a small-sized sprayer in an amount of 100 l per 10 ares. The plants were then cultured in a green house, and the evaluation of the herbicidal effects was conducted on the 14th day after the treatment in accordance with the standards as identified in Table 60. Further, as comparative compounds, compounds identified in Table 61 were formulated and used in the same manner. The results are shown in Tables 80 and 81.

TABLE 80

| Compound No. | Dose ($g^{ai}$/10a) | Herbicidal effect Ec | So | Al | Po | Am | Ch | Phyto-toxicity Or | Tr |
|---|---|---|---|---|---|---|---|---|---|
| 2 | 25 | 5 | 5 | 5 | 5 | 5 | 5 | 1 | 1 |
| 4 | 25 | 5 | 5 | 5 | 5 | 5 | 5 | 0 | 0 |
| 8 | 25 | 5 | 4 | 5 | 5 | 5 | 5 | 1 | 0 |
| 9 | 25 | 5 | 5 | 5 | 5 | 5 | 5 | 0 | 0 |
| 24 | 25 | 5 | 5 | 5 | 5 | 5 | 5 | 2 | 0 |
| 26 | 25 | 5 | 5 | 5 | 5 | 5 | 5 | 1 | 0 |
| 34 | 25 | 5 | 5 | 5 | 5 | 5 | 5 | 0 | 0 |
| 35 | 25 | 5 | 5 | 5 | 5 | 5 | 5 | 0 | 0 |
| 40 | 25 | 3 | 4 | 3 | 5 | 5 | 4 | 1 | 0 |
| 42 | 25 | 3 | 3 | 3 | 4 | 4 | 4 | 1 | 0 |
| 61 | 1.6 | 5 | 5 | 5 | 5 | 5 | 3 | 1 | 0 |
| 62 | 25 | 5 | 5 | 5 | 5 | 5 | 5 | 0 | 0 |
| 171 | 25 | 5 | 5 | 5 | 5 | 5 | 5 | 1 | 0 |
| 262 | 25 | 5 | 5 | 4 | 4 | 5 | 3 | 0 | 0 |
| 506 | 6.3 | 5 | 5 | 5 | 5 | 5 | 4 | 1 | 0 |
| 507 | 6.3 | 5 | 5 | 5 | 5 | 5 | 3 | 1 | 0 |
| 509 | 6.3 | 5 | 5 | 5 | 5 | 5 | 5 | 1 | 0 |
| 511 | 25 | 5 | 5 | 5 | 5 | 5 | 5 | 2 | 0 |
| 512 | 25 | 5 | 5 | 5 | 5 | 5 | 5 | 2 | 0 |
| 522 | 25 | 5 | 5 | 5 | 5 | 5 | 5 | 2 | 0 |
| 526 | 25 | 5 | 5 | 5 | 5 | 5 | 5 | 1 | 1 |
| 527 | 6.3 | 5 | 5 | 5 | 5 | 5 | 5 | 1 | 0 |
| 528 | 25 | 5 | 5 | 5 | 5 | 5 | 5 | 2 | 0 |
| 529 | 6.3 | 5 | 5 | 5 | 5 | 5 | 5 | 1 | 0 |
| 530 | 6.3 | 5 | 5 | 5 | 5 | 5 | 5 | 2 | 1 |
| 531 | 1.6 | 5 | 5 | 5 | 5 | 5 | 5 | 1 | 0 |
| 543 | 25 | 5 | 4 | 5 | 5 | 5 | 4 | 1 | 0 |
| 547 | 6.3 | 5 | 5 | 5 | 5 | 5 | 4 | 2 | 0 |
| 548 | 6.3 | 5 | 5 | 5 | 4 | 5 | 4 | 2 | 1 |
| 549 | 6.3 | 5 | 5 | 5 | 5 | 5 | 5 | 0 | 0 |
| 550 | 6.3 | 5 | 5 | 5 | 5 | 5 | 5 | 0 | 0 |
| 551 | 6.3 | 5 | 5 | 5 | 5 | 5 | 5 | 2 | 0 |
| 562 | 6.3 | 5 | 5 | 5 | 5 | 5 | 5 | 0 | 0 |

TABLE 81

| Compound No. | Dose (gai/10a) | Herbicidal effect Ec | So | Al | Po | Am | Ch | Phyto-toxicity Or | Tr |
|---|---|---|---|---|---|---|---|---|---|
| 563 | 25 | 5 | 5 | 5 | 5 | 5 | 5 | 0 | 0 |
| 567 | 25 | 5 | 5 | 5 | 5 | 5 | 4 | 1 | 0 |
| 568 | 25 | 5 | 5 | 5 | 5 | 5 | 5 | 0 | 0 |
| 578 | 6.3 | 5 | 5 | 5 | 5 | 5 | 4 | 1 | 1 |
| 597 | 1.6 | 4 | 3 | 5 | 5 | 5 | 5 | 1 | 1 |
| 848 | 25 | 2 | 3 | 5 | 5 | 5 | 5 | 1 | 0 |
| 929 | 25 | 5 | 5 | 5 | 5 | 5 | 5 | 1 | 0 |
| Comparative compound A | 25 | 0 | 0 | 0 | 0 | 0 | 0 | 0 | 0 |
| Comparative compound B | 25 | 0 | 0 | 0 | 1 | 2 | 1 | 1 | 0 |
| Comparative compound C | 100 | 2 | 2 | 1 | 1 | 4 | 5 | 4 | 2 |
| Comparative compound D | 400 | 0 | 0 | 0 | 5 | 4 | 5 | 3 | 3 |
| Comparative compound E | 100 | 0 | 0 | 0 | 0 | 0 | 0 | 0 | 0 |
| Comparative compound F | 100 | 0 | 0 | 0 | 0 | 0 | 0 | 0 | 0 |

We claim:

1. A pyrimidine of the formula (I):

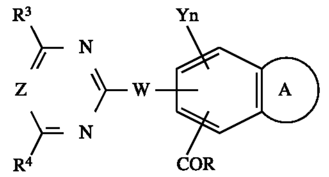

wherein

A is a heterocyclic ring of the formula:

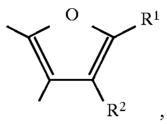

(A-1)

,

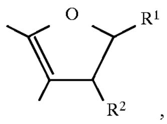

(A-2)

,

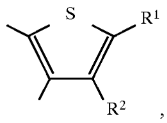

(A-3)

, or

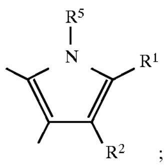

(A-4)

;

R is a hydrogen atom; a hydroxyl group; an alkoxy group which may be substituted with pentanoyloxy, butanoyloxy, hexanoyloxy, ethoxycarbonyl, ethoxy, ethylmalonyl, benzoyloxy, (2'-trimethylsilyl)ethyl, methoxy, trimethylsilyl or (2'-methoxy)ethoxy; a benzyloxy group which may be substituted with methoxy; a phenyloxy group; a $C_1$–$C_2$-alkylthio group; a benzylthio group; a phenylthio group; a $C_3$-alkenyloxy group which may be substituted with Br, a $C_3$-alkynyloxy group; a $C_3$-alkenylthio group; a $C_3$-alkynylthio group; a $C_3$-alkylideneaminoxy group; $O^-[N(CH_2CH_2CH_2CH_4)_4]^+$; $O^-(CH_3)_2CHNH_3^+$;$O^-CH_3CH_2CH_2NH_3^+$; O—$Na^+$; or a group of the formula —$NR^6R^7$, wherein:

each of $R^6$ and $R^7$, which may be the same or different, is a hydrogen atom, a $C_1$–$C_4$-alkyl group, a benzyl group, a phenyl group, a methylsulfonyl group or a phenylsulfonyl group; or $R^6$ and $R^7$ may, together with the nitrogen atom, form a 1,3-imidazole ring, pyrrolidine ring, piperidine ring or morpholine ring;

each of $R^1$ and $R^2$, which may be the same or different, is a hydrogen atom; a formyl group; a $C_1$–$C_8$-alkylcarbonyl group which may be substituted with fluorine; a cyclopentylcarbonyl group; a benzoyl group which may be substituted with chlorine; a pyridylcarbonyl group which may be substituted with methylsulfonyl; a carboxyl group; a group of the formula —$CONR^6R^7$; a $C_1$–$C_8$ alkylthiocarbonyl group which may be substituted with diethylamino; a $C_3$–$C_8$-cycloalkylthiocarbonyl group; a phenyloxycarbonyl group which may be substituted with chlorine or methoxy; a $C_1$–$C_8$-alkoxycarbonyl group which may be substituted with fluorine, chlorine, bromine, 2-furyl, 2-thienyl, cyano, ethoxycarbonyl hydroxy, dimethylamino, cyclopropyl, methoxy, ethoxy or methylthio; a $C_3$-cycloalkyl group; a $C_1$–$C_8$ alkyl group which may be substituted with fluorine, chlorine, methoxy, nitro, cyano, methoxycarbonyl, dimethylamino or hydroxy; a $C_2$–$C_3$ alkenyl group which may be substituted with CN or nitro; a $C_3$ alkynyl group; an ethoxy group; a methoxy group; a phenyl group which may be substituted with chlorine; a halogen atom; a benzyloxycarbonyl group which may be substituted with methoxy; a benzylthiocarbonyl group; a $C_3$–$C_8$ cycloalkoxycarbonyl group; a phenylthiocarbonyl group; a $C_3$–$C_6$ alkenyloxycarbonyl group which may be substituted with chlorine; a $C_3$–$C_6$ alkynyloxycarbonyl group; a $C_3$–$C_6$ alkenylthiocarbonyl group; a $C_3$–$C_6$ alkynylthiocarbonyl group; an isopropylideneaminoxycarbonyl group; a nitro group; a cyano group; a halogenated carbonyl group; a group of the formula $CR^8$═N—$R^9$; a group of the formula $NR^{10}R^{11}$ or a group of the formula N═$CR^{12}R^{13}$, wherein:

$R^6$ and $R^7$ are as defined above;

$R^8$ is a hydrogen atom, a phenyl group, or a methyl group;

$R^9$ is a hydroxyl group, a propyl group, a phenyl group, a benzyl group, a benzyloxy group, a methoxy group, a propoxy group, a propenyloxy group, a propynyloxy group; a phenoxy group, a methylamino group, a dimethylamino group, a phenylamino group or a phenylsulfonylamino group which may be substituted with methyl;

each of $R^{10}$ and $R^{11}$, which may be the same or different, is a hydrogen atom, a methyl group, a phenyl group, a benzyl group, a formyl group, an acetyl group, a benzoyl group, a pyridylcarbonyl group, an ethoxycarbonyl group, a methylsulfonyl group, a phenylsulfonyl group, a carbamoyl group, an ethylthiocarbonyl group or a phenylthiocarbonyl group which may be substituted with chlorine, or $R^{10}$ and $R^{11}$ may, together with the nitrogen atom, form a morpholine ring; and each of $R^{12}$ and $R^{13}$, which may be the same or different, is a hydrogen atom, a methyl group or a phenyl group, or $R^{12}$ and $R^{13}$ may, together with the carbon atom to which they are bound, form a cyclopentylidene group;

each of $R^3$ and $R^4$, which may be the same or different, is a hydrogen atom; a methoxy group which may be substituted with fluorine; a halogen atom; a methylamino group; a dimethylamino group or a $C_1$–$C_6$ alkyl group;

$R^5$ is a hydrogen atom; a methyl group which may be substituted with methoxycarbonyl, ethoxycarbonyl, t-butylcarbonyloxy or methoxy; a formyl group; a $C_1$–$C_8$ alkylcarbonyl group; a benzoyl group which may be substituted with chlorine; a pyridylcarbonyl group; a carbomoyl group; a $C_2$–$C_4$ alkoxycarbonyl group; a phenyloxycarbonyl group; a benzyloxycarbonyl group; a methylthiocarbonyl group; a phenylthiocarbonyl group; a methylsulfonyl group; a p-tolylsulfonyl group; a tri-$C_1$–$C_4$-alkylsilyl group; a propenyl group; a propynyl group; a 4,6-dimethoxypyridin-2-yl group or a trichloromethylthio group;

Y is a halogen atom, a methyl group, a methoxy group, a phenyl group, a nitro group, a methylamino group or a dimethylamino group, n is an integer of from 0 to 2, provided that when n is 2, it may represent a combination of different groups, W is an oxygen atom, a sulfur atom, an N-formyl group, a methylene group, a carbonyl group or a cyanomethylene group, and Z is a nitrogen atom; or a salt thereof.

2. A pyrimidine of the formula (I):

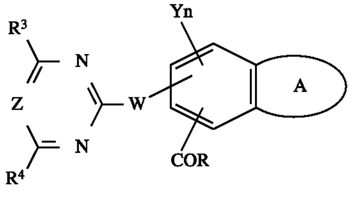

wherein

A is a heterocyclic ring of the formula:

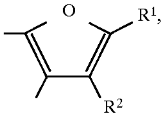

(A-1)

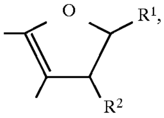

(A-2)

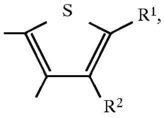

(A-3)

or

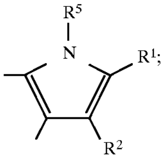

(A-4)

R is a hydrogen atom; a hydroxyl group; an alkoxy group which may be substituted with pentanoyloxy, butanoyloxy, hexanoyloxy, ethoxycarbonyl, ethoxy, ethylmalonyl, benzoyloxy, (2'-trimethylsilyl)ethyl, methoxy, trimethylsilyl or (2'-methoxy)ethoxy; a benzyloxy group which may be substituted with methoxy; a phenyloxy group; a $C_1$–$C_2$-alkylthio group; a benzylthio group; a phenylthio group; a $C_3$-alkenyloxy group which may be substituted with Br, a $C_3$-alkynyloxy group; a $C_3$-alkenylthio group; a $C_3$-alkynylthio group; a $C_3$-alkylideneaminoxy group; $O\_[N(CH_2CH_2CH_2CH_4)_4]^+$; $O^-(CH_3)_2CHNH_3^+$; $O^-CH_3CH_2CH_2NH_3^+$; O—$Na^+$; or a group of the formula —$NR^6R^7$, wherein:

each of $R^6$ and $R^7$, which may be the same or different, is a hydrogen atom, a $C_1$–$C_4$-alkyl group, a benzyl group, a phenyl group, a methylsulfonyl group or a phenylsulfonyl group; or $R^6$ and $R^7$ may, together with the nitrogen atom, form a 1,3-imidazole ring, pyrrolidine ring, piperidine ring or morpholine ring;

each of $R^1$ and $R^2$, which may be the same or different, is a hydrogen atom; a formyl group; a $C_1$–$C_8$-alkylcarbonyl group which may be substituted with fluorine; a cyclopentylcarbonyl group; a benzoyl group which may be substituted with chlorine; a pyridylcarbonyl group which may be substituted with methylsulfonyl; a carboxyl group; a group of the formula —$CONR^6R^7$; a $C_1$–$C_8$ alkylthiocarbonyl group which may be substituted with diethylamino; a $C_3$–$C_8$-cycloalkylthiocarbonyl group; a phenyloxycarbonyl group which may be substituted with chlorine or methoxy; a $C_1$–$C_8$-alkoxycarbonyl group which may be substituted with fluorine, chlorine, bromine, 2-furyl, 2-thienyl, cyano, ethoxycarbonyl hydroxy, dimethylamino, cyclopropyl, methoxy, ethoxy or methylthio; a $C_3$-cycloalkyl group; a $C_1$–$C_8$ alkyl group which may be substituted with fluorine, chlorine, methoxy, nitro, cyano, methoxycarbonyl, dimethylamino or hydroxy; a $C_2$–$C_3$ alkenyl group which may be substituted with CN or nitro; a $C_3$ alkynyl group; an ethoxy group; a methoxy group; a phenyl group which may be substituted with chlorine; a halogen atom; a benzyloxycarbonyl group which may be substituted with methoxy; a benzylthiocarbonyl group; a $C_3$–$C_8$ cycloalkoxycarbonyl group; a phenylthiocarbonyl group; a $C_3$–$C_6$ alkenyloxycarbonyl group which may be substituted with chlorine; a $C_3$–$C_6$ alkynyloxycarbonyl group; a $C_3$–$C_6$ alkenylthiocarbonyl group; a $C_3$–$C_6$ alkynylthiocarbonyl group; an isopropylideneaminoxycarbonyl group; a nitro group; a cyano group; a halogenated carbonyl group; a group of the formula $CR^8$═N—$R^9$; a group of the formula $NR^{10}R^{11}$ or a group of the formula N═$CR^{12}R^{13}$, wherein:

$R^6$ and $R^7$ are as defined above;

$R^8$ is a hydrogen atom, a phenyl group, or a methyl group;

$R^9$ is a hydroxyl group, a propyl group, a phenyl group, a benzyl group, a benzyloxy group, a methoxy group, a propoxy group, a propenyloxy group, a propynyloxy group; a phenoxy group, a methylamino group, a dimethylamino group, a phenylamino group or a phenylsulfonylamino group which may be substituted with methyl;

each of $R^{10}$ and $R^{11}$, which may be the same or different, is a hydrogen atom, a methyl group, a phenyl group, a benzyl group, a formyl group, an acetyl group, a benzoyl group, a pyridylcarbonyl group, an ethoxycarbonyl group, a methylsulfonyl group, a phenylsulfonyl group, a carbamoyl group, an ethylthiocarbonyl group or a phenylthiocarbonyl group which may be substituted with chlorine, or $R^{10}$ and $R^{11}$ may, together with the nitrogen atom, form a morpholine ring; and each of $R^{12}$ and $R^{13}$, which may be the same or different, is a hydrogen atom, a methyl group or a phenyl group, or $R^{12}$ and $R^{13}$ may, together with the carbon atom to which they are bound, form a cyclopentylidene group;

provided that when A is of the formula (A-1), either $R^1$ or $R^2$ is a formyl group, a $C_1$–$C_8$-alkylcarbonyl group which may be substituted with fluorine; a cyclopentylcarbonyl group; a benzoyl group which may be substituted with chlorine; a pyridylcarbonyl group which may be substituted with methylsulfonyl; a carbonyl group; a group of the formula —$CONR^6R^7$ wherein $R^6$ and $R^7$ are as defined above; a $C_1$–$C_8$ alkylthiocarbonyl group which may be substituted with diethylamino; a $C_3$–$C_8$-cycloalkylthiocarbonyl group; a phenyloxycarbonyl group which may be substituted with chlorine or methoxy; a $C_1$–$C_8$-alkoxycarbonyl group which may be substituted with fluorine, chlorine, bromine, 2-furyl, 2-thienyl, cyano, ethoxycarbonyl hydroxy, dimethylamino, cyclopropyl, methoxy, ethoxy or methylthio; a $C_2$–$C_3$ alkenyl group which may be substituted with CN or nitro; a $C_3$ alkynyl group; a phenyl group which may be substituted with chlorine; a halogen atom; a benzyloxycarbonyl group which may be substituted with methoxy; a benzylthiocarbonyl group; a phenylthiocarbonyl group; a $C_3$–$C_6$ alkenyloxycarbonyl group which may be substituted with chlorine; a $C_3$–$C_6$ alkynyloxycarbonyl group; a $C_3$–$C_6$ alkenylthiocarbonyl group; a $C_3$–$C_6$ alkynylthiocarbonyl group; an isopropylideneaminoxycarbonyl group; a nitro group; a cyano group; or a halogenated carbonyl group;

each of $R^3$ and $R^4$, which may be the same or different, is a hydrogen atom; a methoxy group which may be substituted with fluorine; a halogen atom; a methylamino group; a dimethylamino group or a $C_1$–$C_6$ alkyl group;

$R^5$ is a hydrogen atom; a methyl group which may be substituted with methoxycarbonyl, ethoxycarbonyl, t-butylcarbonyloxy or methoxy; a formyl group; a $C_1$–$C_8$ alkylcarbonyl group; a benzoyl group which may be substituted with chlorine; a pyridylcarbonyl group; a carbomoyl group; a $C_2$–$C_4$ alkoxycarbonyl group; a phenyloxycarbonyl group; a benzyloxycarbonyl group; a methylthiocarbonyl group; a phenylthiocarbonyl group; a methylsulfonyl group; a p-tolylsulfonyl group; a tri-$C_1$–$C_4$-alkylsilyl group; a propenyl group; a propynyl group; a 4,6-dimethoxypyridin-2-yl group or a trichloromethylthio group;

Y is a halogen atom, a methyl group, a methoxy group, a phenyl group, a nitro group, a methylamino group or a dimethylamino group, n is an integer of from 0 to 2, provided that when n is 2, it may represent a combination of different groups, W is an oxygen atom, a sulfur atom, an N-formyl group, a methylene group, a carbonyl group or a cyanomethylene group, and Z is a nitrogen atom; or a salt thereof.

3. A triazine derivative or a salt thereof according to claim 1, wherein A in the formula (I) is (A-1), (A-2), (A-3) or (A-4), W is an oxygen atom or a sulfur atom, and each of $R^3$ and $R^4$ is an alkoxy group.

4. An herbicidal composition containing an herbicidally effective amount of the triazine of claim 1 and a carrier therefor.

5. An herbicidal composition containing an herbicidally effective amount of the triazine of claim 2 and a carrier therefor.

6. An herbicidal composition containing an herbicidally effective amount of the triazine of claim 3 and a carrier therefor.

* * * * *